(12) United States Patent
Narayan et al.

(10) Patent No.: US 10,856,760 B2
(45) Date of Patent: Dec. 8, 2020

(54) METHOD AND SYSTEM FOR DETECTION OF BIOLOGICAL RHYTHM DISORDERS

(71) Applicants: THE REGENTS OF THE UNIVERSITY OF CALIFORNIA, Oakland, CA (US); TOPERA, INC., Menlo Park, CA (US)

(72) Inventors: Sanjiv M. Narayan, Palo Alto, CA (US); Ruchir Sehra, Scottsdale, AZ (US)

(73) Assignees: The Regents of the University of California, Oakland, CA (US); Topera, Inc., Menlo Park, CA (US); The United States of America as Represented by the Department of Veterans Affairs, Washington, DC (US)

( * ) Notice: Subject to any disclaimer, the term of this patent is extended or adjusted under 35 U.S.C. 154(b) by 547 days.

(21) Appl. No.: 15/649,494

(22) Filed: Jul. 13, 2017

(65) Prior Publication Data
US 2017/0311835 A1 Nov. 2, 2017

Related U.S. Application Data

(63) Continuation of application No. 14/473,112, filed on Aug. 29, 2014, now Pat. No. 9,717,436, which is a
(Continued)

(51) Int. Cl.
*A61B 5/04* (2006.01)
*A61B 5/0452* (2006.01)
(Continued)

(52) U.S. Cl.
CPC .......... *A61B 5/0452* (2013.01); *A61B 5/0255* (2013.01); *A61B 5/044* (2013.01);
(Continued)

(58) Field of Classification Search
CPC ..... A61B 5/0452; A61B 5/044; A61B 5/0432; A61B 5/04011; A61B 5/7278;
(Continued)

(56) References Cited

U.S. PATENT DOCUMENTS 4,421,114 A 12/1983 Berkovits et al.
4,630,204 A 12/1986 Mortara
(Continued)

FOREIGN PATENT DOCUMENTS

CN 101461711 A 6/2009
EP 2269691 A2 1/2011
(Continued)

OTHER PUBLICATIONS

Ciaccop, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.
(Continued)

*Primary Examiner* — Amanda K Hulbert
*Assistant Examiner* — Natasha Patel
(74) *Attorney, Agent, or Firm* — Eleanor Musick; Musick Davison LLP

(57) ABSTRACT

A system for processing cardiac activation information associated with a complex rhythm disorder identifies a location of the heart rhythm disorder by determining activations within cardiac signals obtained at neighboring locations of the heart and arranging the activations to identify an activation trail. The activation trail may define a rotational pattern or radially emanating pattern corresponding to an approximate core of the heart rhythm disorder.

27 Claims, 25 Drawing Sheets
(6 of 25 Drawing Sheet(s) Filed in Color)

Related U.S. Application Data continuation of application No. 14/137,929, filed on Dec. 20, 2013, now Pat. No. 8,868,169, which is a continuation of application No. 13/081,411, filed on Apr. 6, 2011, now Pat. No. 8,700,140.

(60) Provisional application No. 61/342,016, filed on Apr. 8, 2010.

(51) Int. Cl.

| | |
|---|---|
| *A61B 5/0456* | (2006.01) |
| *A61B 5/042* | (2006.01) |
| *A61B 5/0472* | (2006.01) |
| *A61B 5/046* | (2006.01) |
| *A61B 5/0464* | (2006.01) |
| *A61B 5/00* | (2006.01) |
| *A61B 5/0255* | (2006.01) |
| *A61B 5/0432* | (2006.01) |
| *A61B 5/044* | (2006.01) |

(52) U.S. Cl.
CPC .......... *A61B 5/046* (2013.01); *A61B 5/04011* (2013.01); *A61B 5/04012* (2013.01); *A61B 5/0422* (2013.01); *A61B 5/0432* (2013.01); *A61B 5/0456* (2013.01); *A61B 5/0464* (2013.01); *A61B 5/0472* (2013.01); *A61B 5/4857* (2013.01); *A61B 5/6852* (2013.01); *A61B 5/7221* (2013.01); *A61B 5/7264* (2013.01); *A61B 5/7278* (2013.01); *A61B 5/726* (2013.01)

(58) Field of Classification Search
CPC ... A61B 5/7264; A61B 5/6852; A61B 5/4857; A61B 5/0255; A61B 5/7221; A61B 5/04012; A61B 5/0456; A61B 5/0464; A61B 5/046; A61B 5/0472; A61B 5/0422; A61B 5/726
See application file for complete search history.

(56) References Cited

U.S. PATENT DOCUMENTS

| | | | |
|---|---|---|---|
| 4,754,763 A | 7/1988 | Doemland | |
| 4,905,707 A | 3/1990 | Davies et al. | |
| 4,905,708 A | 3/1990 | Davies | |
| 5,029,082 A | 7/1991 | Shen et al. | |
| 5,092,341 A | 3/1992 | Kelen | |
| 5,121,750 A | 6/1992 | Katims | |
| 5,172,699 A | 12/1992 | Svenson et al. | |
| 5,178,154 A | 1/1993 | Ackmann et al. | |
| 5,366,487 A | 11/1994 | Adams et al. | |
| 5,427,112 A | 6/1995 | Noren et al. | |
| 5,433,198 A | 7/1995 | Desai | |
| 5,439,483 A | 8/1995 | Duong-Van | |
| 5,450,846 A | 9/1995 | Goldreyer | |
| 5,458,621 A | 10/1995 | White et al. | |
| 5,480,422 A | 1/1996 | Ben-Haim | |
| 5,487,391 A | 1/1996 | Panescu | |
| 5,554,177 A * | 9/1996 | Kieval .............. | A61N 1/36514 607/17 |
| 5,582,173 A | 12/1996 | Li | |
| 5,645,070 A | 7/1997 | Turcott | |
| 5,657,755 A | 8/1997 | Desai | |
| 5,662,108 A | 9/1997 | Budd et al. | |
| 5,687,737 A | 11/1997 | Branham et al. | |
| 5,718,241 A | 2/1998 | Ben-Haim et al. | |
| 5,795,303 A | 8/1998 | Swanson et al. | |
| 5,810,740 A | 9/1998 | Paisner | |
| 5,817,134 A | 10/1998 | Greenhut et al. | |
| 5,819,740 A | 10/1998 | Muhlenberg | |
| 5,836,889 A | 11/1998 | Wyborny et al. | |
| 5,840,025 A | 11/1998 | Ben-Haim | |
| 5,848,972 A | 12/1998 | Triedman et al. |
| 5,868,680 A | 2/1999 | Steiner et al. |
| 5,954,661 A | 9/1999 | Greenspon et al. |
| 5,954,665 A | 9/1999 | Ben-Haim |
| 6,052,618 A | 4/2000 | Dahlke et al. |
| 6,066,094 A | 5/2000 | Ben-Haim |
| 6,097,983 A | 8/2000 | Strandberg |
| 6,112,117 A | 8/2000 | KenKnight et al. |
| 6,115,628 A | 9/2000 | Stadler et al. |
| 6,188,924 B1 | 2/2001 | Swanson et al. |
| 6,208,888 B1 | 3/2001 | Yonce |
| 6,236,883 B1 | 5/2001 | Ciaccio et al. |
| 6,251,125 B1 | 6/2001 | Kenknight et al. |
| 6,256,540 B1 | 7/2001 | Panescu et al. |
| 6,301,496 B1 | 10/2001 | Reisfeld |
| 6,324,421 B1 | 11/2001 | Stadler et al. |
| 6,360,121 B1 | 3/2002 | Shoda et al. |
| 6,397,100 B2 | 5/2002 | Stadler et al. |
| 6,438,406 B2 | 8/2002 | Yonce |
| 6,438,409 B1 | 8/2002 | Malik et al. |
| 6,449,503 B1 | 9/2002 | Hsu |
| 6,510,339 B2 | 1/2003 | Kovtun et al. |
| 6,522,905 B2 | 2/2003 | Desai |
| 6,539,256 B1 | 3/2003 | Kenknight et al. |
| 6,542,773 B2 | 4/2003 | Dupree et al. |
| 6,553,251 B1 | 4/2003 | Landesmaki |
| 6,584,345 B2 | 6/2003 | Govari |
| 6,725,085 B2 | 4/2004 | Schwartzman et al. |
| 6,738,655 B1 | 5/2004 | Sen et al. |
| 6,788,969 B2 | 9/2004 | Dupree et al. |
| 6,847,839 B2 | 1/2005 | Ciaccio et al. |
| 6,856,830 B2 | 2/2005 | He |
| 6,889,081 B2 | 5/2005 | Hsu |
| 6,892,091 B1 | 5/2005 | Ben-Haim et al. |
| 6,920,350 B2 | 7/2005 | Xue et al. |
| 6,941,166 B2 | 9/2005 | MacAdam et al. |
| 6,950,696 B2 | 9/2005 | Bjorling et al. |
| 6,950,702 B2 | 9/2005 | Sweeney |
| 6,959,212 B2 | 10/2005 | Hsu et al. |
| 6,975,900 B2 | 12/2005 | Rudy et al. |
| 6,978,168 B2 | 12/2005 | Beatty et al. |
| 6,985,768 B2 | 1/2006 | Hemming et al. |
| 7,016,719 B2 | 3/2006 | Rudy et al. |
| 7,043,292 B2 | 5/2006 | Tarjan et al. |
| 7,076,288 B2 | 7/2006 | Skinner |
| 7,117,030 B2 | 10/2006 | Berenfeld et al. |
| 7,123,954 B2 | 10/2006 | Narayan et al. |
| 7,206,630 B1 | 4/2007 | Tarler |
| 7,215,993 B2 | 5/2007 | Lin |
| 7,245,962 B2 | 7/2007 | Ciaccio et al. |
| 7,263,397 B2 | 8/2007 | Hauck et al. |
| 7,283,865 B2 | 10/2007 | Noren |
| 7,289,843 B2 | 10/2007 | Beatty et al. |
| 7,289,845 B2 | 10/2007 | Sweeney et al. |
| 7,328,063 B2 | 2/2008 | Zhang et al. |
| 7,369,890 B2 | 5/2008 | Lovett |
| 7,457,664 B2 | 11/2008 | Zhang et al. |
| 7,505,810 B2 | 3/2009 | Harlev et al. |
| 7,509,170 B2 | 3/2009 | Zhang et al. |
| 7,515,954 B2 | 4/2009 | Harlev et al. |
| 7,567,835 B2 | 7/2009 | Gunderson et al. |
| 7,580,744 B2 | 8/2009 | Hsu |
| 7,620,446 B2 | 11/2009 | Ferek-Petric |
| 7,657,307 B2 | 2/2010 | Dam et al. |
| 7,729,753 B2 | 6/2010 | Kremliovsky et al. |
| 7,734,333 B2 | 6/2010 | Ghanem et al. |
| 7,734,336 B2 | 6/2010 | Ghanem et al. |
| 7,738,948 B2 | 6/2010 | Rouw et al. |
| 7,742,812 B2 | 6/2010 | Ghanem et al. |
| 7,751,882 B1 | 7/2010 | Helland |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,801,594 B1 | 9/2010 | Higham |
| 7,907,993 B2 | 3/2011 | Ghanem et al. |
| 7,907,994 B2 | 3/2011 | Stolarski et al. |
| 7,930,018 B2 | 4/2011 | Harley et al. |
| 7,930,020 B2 | 4/2011 | Zhang et al. |
| 7,953,475 B2 | 5/2011 | Harlev et al. |

(56) References Cited

U.S. PATENT DOCUMENTS

| | | |
|---|---|---|
| 7,962,202 B2 | 6/2011 | Bhunia |
| 8,050,732 B2 | 11/2011 | Desai |
| 8,050,751 B2 | 11/2011 | Zhang et al. |
| 8,050,757 B2 | 11/2011 | Hsu |
| 8,095,205 B2 | 1/2012 | Bhunia |
| 8,095,206 B2 | 1/2012 | Ghanem et al. |
| 8,160,684 B2 | 4/2012 | Ghanem et al. |
| 8,165,666 B1 | 4/2012 | Briggs et al. |
| 8,165,671 B2 | 4/2012 | Freeman et al. |
| 8,175,702 B2 | 5/2012 | Efimov et al. |
| 8,306,618 B2 | 11/2012 | Ghanem et al. |
| 8,315,697 B2 | 11/2012 | Hsu |
| 8,340,766 B2 | 12/2012 | Ryu et al. |
| 8,386,024 B2 | 2/2013 | Gunderson et al. |
| 8,435,185 B2 | 5/2013 | Ghanem et al. |
| 8,489,171 B2 | 7/2013 | Hauck et al. |
| 8,521,266 B2 | 8/2013 | Narayan et al. |
| 8,588,885 B2 | 11/2013 | Hall et al. |
| 8,594,777 B2 | 11/2013 | Briggs et al. |
| 8,639,325 B2 | 1/2014 | Efimov et al. |
| 8,676,303 B2 | 3/2014 | Narayan |
| 8,715,199 B1 | 5/2014 | Macneil et al. |
| 8,812,074 B2 | 8/2014 | Kordis et al. |
| 8,838,222 B2 | 9/2014 | Narayan et al. |
| 8,838,223 B2 | 9/2014 | Narayan et al. |
| 9,031,642 B2 | 5/2015 | Ghosh |
| 9,050,006 B2 | 6/2015 | Narayan et al. |
| 9,055,876 B2 | 6/2015 | Narayan et al. |
| 9,055,877 B2 | 6/2015 | Narayan et al. |
| 9,055,878 B2 | 6/2015 | Narayan et al. |
| 9,089,269 B2 | 7/2015 | Narayan et al. |
| 9,107,600 B2 | 8/2015 | Narayan et al. |
| 9,220,427 B2 | 12/2015 | Narayan et al. |
| 9,241,667 B2 | 1/2016 | Narayan et al. |
| 9,282,910 B2 | 3/2016 | Narayan et al. |
| 9,332,915 B2 | 5/2016 | Narayan et al. |
| 9,375,156 B2 | 6/2016 | Narayan et al. |
| 9,380,950 B2 | 7/2016 | Narayan et al. |
| 9,392,948 B2 | 7/2016 | Briggs et al. |
| 9,393,425 B2 | 7/2016 | Narayan |
| 9,398,860 B2 | 7/2016 | Macneil et al. |
| 9,398,883 B2 | 7/2016 | Narayan et al. |
| 9,408,536 B2 | 8/2016 | Narayan et al. |
| 9,439,573 B2 | 9/2016 | Narayan et al. |
| 9,468,387 B2 | 10/2016 | Narayan et al. |
| 9,549,684 B2 | 1/2017 | Narayan et al. |
| 9,655,535 B2 | 5/2017 | Narayan et al. |
| 2002/0045810 A1* | 4/2002 | Ben-Haim ............ A61B 5/0215 600/374 |
| 2003/0018277 A1 | 1/2003 | He |
| 2003/0083587 A1 | 5/2003 | Ferek-Petric |
| 2003/0130586 A1 | 7/2003 | Starobin |
| 2004/0093035 A1 | 5/2004 | Schwartz et al. |
| 2004/0243012 A1* | 12/2004 | Ciaccio ............ A61B 5/04011 600/509 |
| 2004/0243014 A1 | 12/2004 | Lee et al. |
| 2005/0137638 A1 | 6/2005 | Yonce et al. |
| 2005/0203502 A1 | 9/2005 | Boveja et al. |
| 2006/0161069 A1 | 7/2006 | Li |
| 2007/0016261 A1 | 1/2007 | Dong et al. |
| 2007/0055167 A1 | 3/2007 | Bullinga |
| 2007/0197929 A1* | 8/2007 | Porath ................ A61B 5/0422 600/523 |
| 2007/0208260 A1 | 9/2007 | Afonso |
| 2007/0208263 A1 | 9/2007 | John et al. |
| 2007/0232948 A1 | 10/2007 | Stadler et al. |
| 2007/0299351 A1 | 12/2007 | Harlev et al. |
| 2008/0097539 A1 | 4/2008 | Belalcazar |
| 2008/0109041 A1 | 5/2008 | de Voir |
| 2008/0114258 A1 | 5/2008 | Zhang et al. |
| 2008/0208012 A1 | 8/2008 | Ali |
| 2008/0319332 A1 | 12/2008 | Sommo et al. |
| 2009/0069704 A1 | 3/2009 | MacAdam et al. |
| 2009/0099468 A1 | 4/2009 | Thiagalingam et al. |
| 2009/0099618 A1 | 4/2009 | Rousso et al. |
| 2009/0112106 A1 | 4/2009 | Zhang |
| 2009/0112110 A1 | 4/2009 | Zhang |
| 2009/0112199 A1 | 4/2009 | Zhang et al. |
| 2009/0131760 A1 | 5/2009 | Ali et al. |
| 2009/0163968 A1 | 6/2009 | Donofrio |
| 2009/0259266 A1 | 10/2009 | Zhang et al. |
| 2009/0299203 A1 | 12/2009 | de Voir et al. |
| 2010/0026543 A1 | 2/2010 | Tsai et al. |
| 2010/0204592 A1 | 8/2010 | Hatib et al. |
| 2010/0217143 A1 | 8/2010 | Whittington et al. |
| 2010/0249627 A1 | 9/2010 | Zhang et al. |
| 2010/0298729 A1 | 11/2010 | Zhang et al. |
| 2010/0305456 A1 | 12/2010 | Brainard, II |
| 2010/0324435 A1 | 12/2010 | Higham |
| 2011/0077540 A1 | 3/2011 | Belalcazar |
| 2011/0087121 A1 | 4/2011 | Zhang et al. |
| 2011/0112425 A1 | 5/2011 | Muhlsteff et al. |
| 2011/0118803 A1 | 5/2011 | Hou et al. |
| 2011/0130801 A1 | 6/2011 | Maskara et al. |
| 2011/0196249 A1 | 8/2011 | Staeuber et al. |
| 2011/0257547 A1 | 10/2011 | Zhang |
| 2011/0282227 A1 | 11/2011 | Zhang |
| 2012/0184858 A1 | 7/2012 | Harlev et al. |
| 2012/0184863 A1 | 7/2012 | Harley et al. |
| 2012/0232417 A1 | 9/2012 | Zhang |
| 2013/0245474 A1 | 9/2013 | Nicolson et al. |
| 2013/0324871 A1 | 12/2013 | Dubois et al. |
| 2013/0345577 A1 | 12/2013 | Thakur et al. |
| 2014/0005562 A1 | 1/2014 | Bunch et al. |
| 2014/0336520 A1 | 11/2014 | Zeng et al. |
| 2014/0371609 A1 | 12/2014 | Narayan et al. |
| 2015/0366476 A1 | 12/2015 | Laughner et al. |
| 2016/0015283 A1 | 1/2016 | Narayan et al. |
| 2016/0022163 A1 | 1/2016 | Narayan et al. |
| 2016/0262643 A1 | 9/2016 | Ng et al. |
| 2016/0278657 A1 | 9/2016 | Narayan et al. |
| 2016/0302734 A1 | 10/2016 | Narayan |
| 2016/0360983 A1 | 12/2016 | Narayan et al. |
| 2016/0374571 A1 | 12/2016 | Narayan et al. |
| 2017/0007176 A1 | 1/2017 | Narayan et al. |
| 2017/0232263 A1 | 8/2017 | Narayan |
| 2017/0245774 A1 | 8/2017 | Narayan et al. |
| 2017/0340229 A1 | 11/2017 | Narayan et al. |
| 2019/0038157 A1 | 2/2019 | Narayan et al. |

FOREIGN PATENT DOCUMENTS

| | | |
|---|---|---|
| EP | 1808124 B1 | 4/2011 |
| EP | 2638854 A1 | 9/2013 |
| JP | H05502816 A | 5/1993 |
| JP | H09215667 | 8/1997 |
| WO | 1991019452 A1 | 12/1991 |
| WO | 1994021168 A1 | 9/1994 |
| WO | 1996025096 A1 | 8/1996 |
| WO | 2005035046 A2 | 4/2005 |
| WO | 2005115232 A1 | 12/2005 |
| WO | 2007078421 A2 | 7/2007 |
| WO | 2007106829 A2 | 9/2007 |
| WO | 2008035070 A2 | 3/2008 |
| WO | 2013150740 A1 | 10/2013 |

OTHER PUBLICATIONS

Eckman, et al. "Recurrence plots of dynamical systems," Europhys. Lett., 4 (3), Nov. 1, 1987 pp. 973-977.
English-language translation of Chinese patent publication No. CN 101461711A, published Jun. 24, 2009.
EP09819953 Supplementary European Search Report & European Search Opinion dated Feb. 7, 2012, 12 pages.
EP12711553 Supplementary European Search Report & European Search Opinion, dated Sep. 11, 2013, 7 pages.
EP12779506.0 Supplementary European Search Report & European Search Opinion dated Nov. 18, 2014, 8 pages.
EP12855266.8: Supplementary European Search Report & European Search Opinion, dated Jun. 2, 2015, 9 pages.
EP12855738.6: Supplementary European Search Report & European Search Opinion, dated Jun. 5, 2015, 9 pages.

(56) References Cited

OTHER PUBLICATIONS

EP14763969.4 Supplementary European Search Report & European Search Opinion dated Oct. 21, 2016, 7 pages.
EP147665096.4 Supplementary European Search Report & European Search Opinion, dated Oct. 21, 2016, 6 pages.
EP15192804.1 Supplementary European Search Report, dated Feb. 18, 2016, 7 pages.
Holm, M. et al., "A New Method for Analysis of Atrial Activation During Chronic Atrial Fibrillation in Man", IEEE Transactions on Biomedical Engineering, vol. 43, No. 2, Feb. 1, 1996, pp. 198-210.
Houben, R.P.M., et al, "Automatic mapping of human atrial fibrillation by template matching", Heart Rhythm, vol. 3, No. 10, Oct. 1, 2006, pp. 1221-1228.
Houben, R.P.M., et al., "Processing of Intracardiac Electrograms in Atrial Fibrillation", IEEE Engineering in Medicine and Biology Magazine, Nov./Dec. 2006, pp. 40-51.
Jung, TP et al, Removing Electroencephalographic Artifacts by Blind Source Separation, Psychophysiology, 37.02 (2000): 163-178.
Kadish, A., et al., "Characterization of fibrillatory rhythms by ensemble vector directional analysis", Am J Physiol,—Heart Circ. Physiol., vol. 285, Oct. 2003, pp. H1705-H1719.
Kalifa, J, et al. "Mechanisms of wave fractionation at boundaries of high-frequency excitation in the posterior left atrium of the isolated sheep heart during atrial fibrillation," Circulation, vol. 113, No. 5, Feb. 7, 2006, pp. 626-633.
Lin, Y-J, et al., "Electrophyiological Characteristics and Catheter Ablation in Patients With Paroxysmal Right Atrial Fibrillation", Circulation, Sep. 20, 2005; 112(12): 1692-1700, EPub Sep. 12, 2005.
Masse, S., et al., "Wave similarity of human ventricular fibrillation from bipolar electrograms", Eurospace (2007) vol. 9, pp. 10-19.
Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.
Narayan, S.M., et al., "Dynamics factors preceding the initiation of atrial fibrillation in humans", Heart Rhythm, vol. 5, No. 6, Jun. 1, 2008, pp. S22-S25.
PCT/US2009/060178 International Preliminary Report on Patentability and Written Opinion, dated Apr. 12, 2011, 10 pages.
PCT/US2011/031468 International Preliminary Report on Patentability and Written Opinion, dated Oct. 9, 2012, 8 pages.
PCT/US2011/031470 International Preliminary Report on Patentability and Written Opinion, dated Oct. 9, 2012, 7 pages.
PCT/US2012/029935 International Search Report and Written Opinion, dated Nov. 8, 2012, 9 pages.
PCT/US2012/036157 International Preliminary Report on Patentability and Written Opinion, dated Aug. 14, 2012, 8 pages.
PCT/US2012/068639 International Preliminary Report on Patentability and Written Opinion, dated Jun. 10, 2013; 6 pages.
PCT/US2012/068640 International Preliminary Report on Patentability and Written Opinion, dated Jun. 10, 2013; 5 pages.
PCT/US2014/029616 International Search Report and Written Opinion, dated Sep. 18, 2014; 9 pages.
PCT/US2014/029645 International Search Report and Written Opinion, dated Aug. 18, 2014, 17 pages.
PCT/US2015/023929, International Search Report and Written Opinion, dated Jul. 9, 2015, 8 pages.
PCT/US2015/046742 International Search Report and Written Opinion; dated Dec. 1, 2015, 5 pages.
PCT/US2017/030683, International Search Report and Written Opinion dated Aug. 1, 2017, 6 pages.
Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.
Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No. 12, Dec. 2003, pp. 1537-1549.
Sun, Yan, et al., "Characteristic wave detection in Ecg signal using morphological transform", BMC Cardiovascular Disorders, vol. 5, No. 28, 2005, 7 pages.
Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.
Ulphani, J.S., et al., "Frequency gradients during two different forms of fibrillation in canine atria", Heart Rhythm, vol. 4, No. 10, Oct. 2007, pp. 1315-1323.
Umapathy, K, et al. "Spatiotemporal Frequency Analysis of Ventricular Fibrillation in Explanted Human Hearts," IEEE Transactions in Biomedical Engineering, IEEE Service Center, Piscataway, NJ USA, vol. 56, No. 2, Feb. 1, 2009, pp. 238-335.
Yenn-Jiang L, et al. "Electrophysiological Mechanisms and Catheter Ablation of Complex Atrial Arrhythmias from Crista Terminalis: Insight from Three-Dimentional Noncontact Mapping," Pacing and Clinical Electrophysiology, vol. 27, No. 9, Sep. 1, 2004, pp. 1231-1239.
Botteron, G.W. et al., A technique for measurement of the extent of spatial organization of atrial activation during atrial fibrillation ii the intact human ar, IEEE Transactions on Biomedical Engineering, Jun. 1995, pp. 579-586, vol. 42, No. 6.
Censi, F. et al., "Recurrent Patterns of Atrial Depolarization During Atrial Fibrillation Assessed by Recurrence Plot Quantification", Annals of Biomedical Engineering, 2000, pp. 61-70; vol. 28.
EP15774130.7 Supplementary European Search Report & European Search Opinion, dated Nov. 15, 2017, 9 pages.
EP15836641 Supplementary European Search Report & European Search Opinion, dated Mar. 8, 2018, 8 pages.
Xiao, Yuping et al., Parameter estimation of spiral waves from atrial electrograms:, Proceedings of International Conference on Acoustics, Speech and Signal Processing (ICASSP '03) Apr. 6-10, 2003, Hong Kong, China, IEEE, 2003 IEEE International Conference, vol. 5, Apr. 6, 2003, pp. V_245-V_248.

* cited by examiner

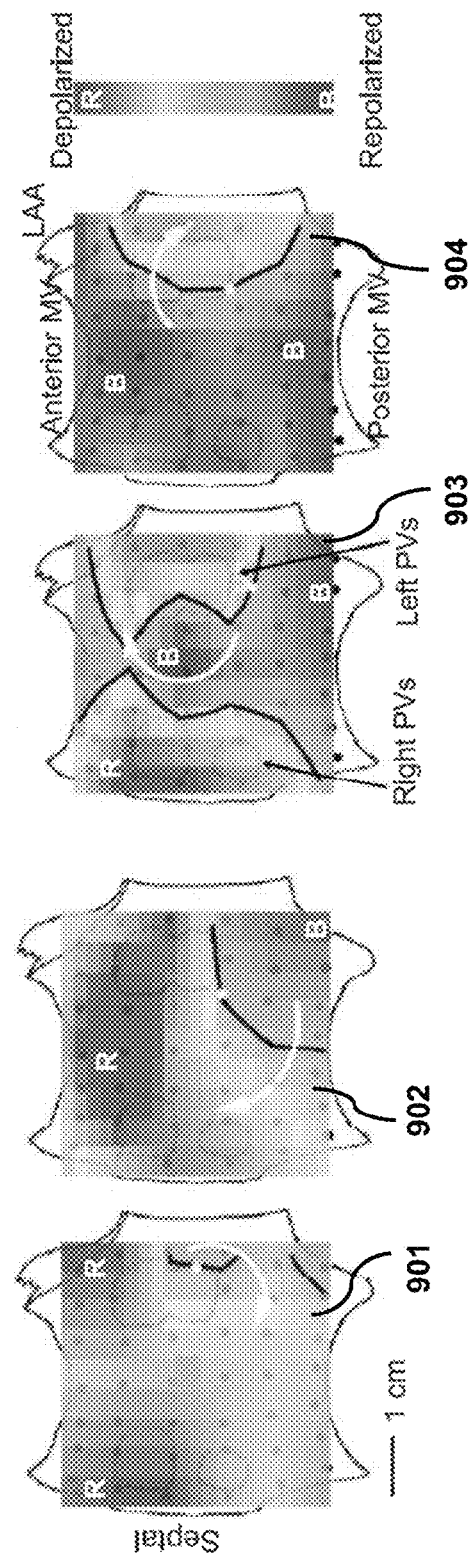
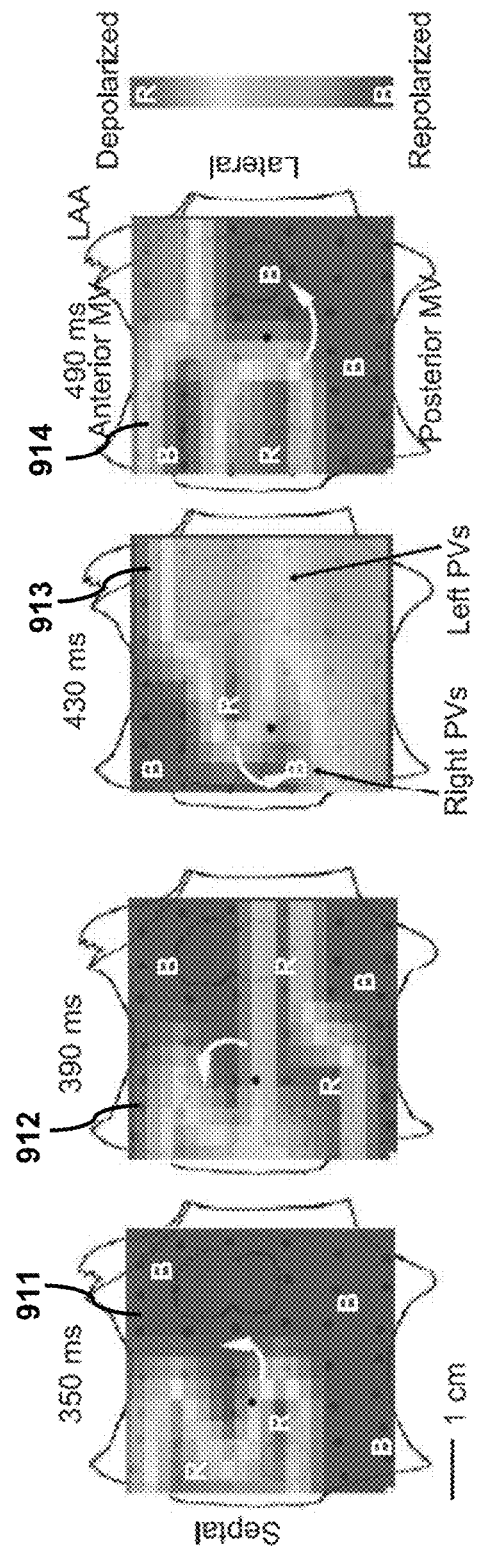
FIG. 15A
FIG. 15B

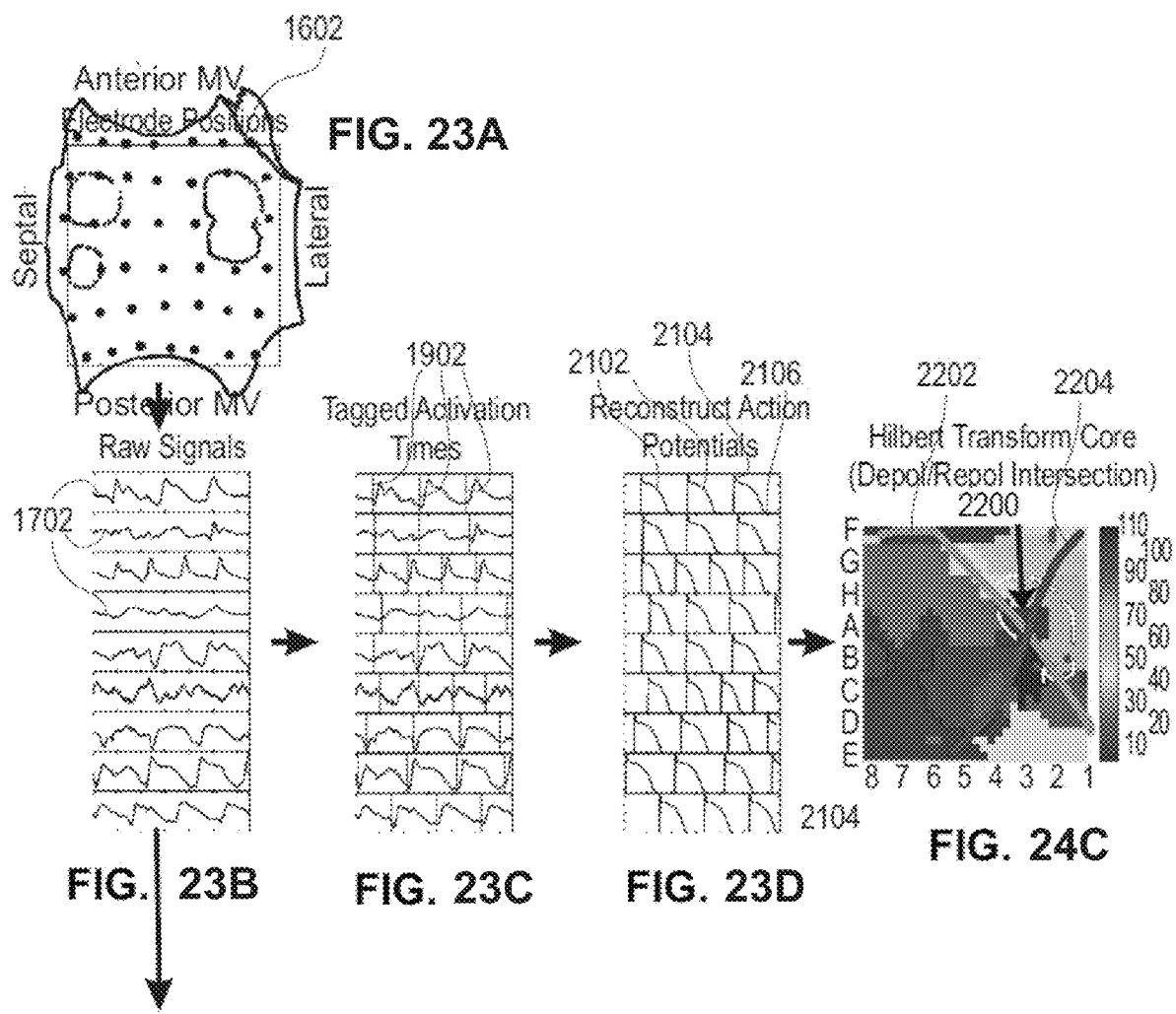
FIG. 23A
FIG. 23B
FIG. 23C
FIG. 23D
FIG. 24C
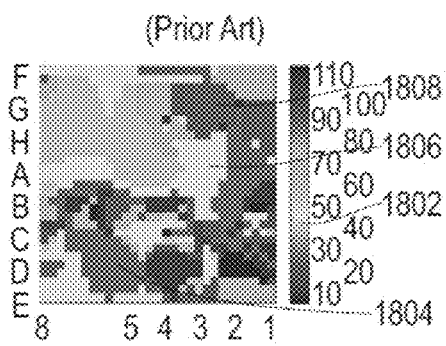
FIG. 24A
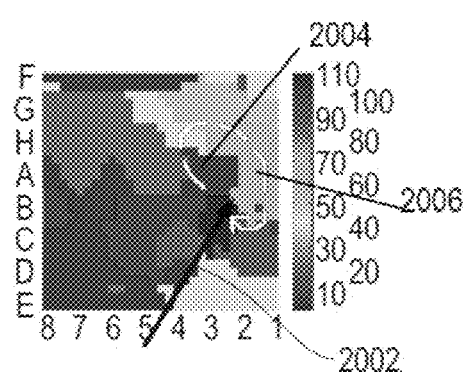
FIG. 24B

METHOD AND SYSTEM FOR DETECTION OF BIOLOGICAL RHYTHM DISORDERS

RELATED APPLICATIONS

This application is a continuation of application Ser. No. 14/473,112, filed Aug. 29, 2014, which is a continuation of application Ser. No. 14/137,929, filed Dec. 20, 2013, issued as U.S. Pat. No. 8,868,169, which is a continuation of Ser. No. 13/081,411, filed Apr. 6, 2011, issued as U.S. Pat. No. 8,700,140, which claims priority to Provisional Application No. 61/342,016, filed Apr. 8, 2010, each of which is incorporated herein by reference in its entirety.

GOVERNMENT RIGHTS

This invention was made with government support under Grants HL070529 and HL083359 awarded by the National Institutes of Health. The government has certain rights in the invention.

BACKGROUND

Field

This invention relates generally to the field of medicine and more specifically to a method, system and machine for diagnosing, finding the source for and treating irregularities and other disorders of biological rhythms. In particular, the present invention can be applied to minimally-invasive techniques or surgical techniques to detect, diagnose and treat the disorder. One embodiment directs this invention to disorders of heart rhythm, another to electrical disorders of the brain and nervous system and others to electrical or contractile disorders of the smooth muscle of the gastrointestinal and genitourinary systems.

Brief Description of the Related Art

Heart rhythm disorders are very common in the United States, and are significant causes of morbidity, lost days from work, and death. Heart rhythm disorders exist in many forms, of which the most complex and difficult to treat are atrial fibrillation (AF), ventricular tachycardia (VT) and ventricular fibrillation (VF). Other rhythms are easier to treat, but may also be clinically significant including atrial tachycardia (AT), supraventricular tachycardia (SVT), atrial flutter (AFL), premature atrial complexes/beats (SVE) and premature ventricular complexes/beats (PVC). Under certain conditions, rapid activation of the normal sinus node can cause the heart rhythm disorder of inappropriate sinus tachycardia or sinus node reentry.

Treatment of heart rhythm disorders, particularly the complex ones of AF, VF and VT, can be very difficult. Pharmacologic therapy is particularly suboptimal for AF (Singh, Singh et al. 2005) and VT or VF (Bardy, Lee et al. 2005) and, as a result, there is considerable interest in non-pharmacologic therapy. Ablation is a promising and increasingly used therapy to eliminate heart rhythm disorders by maneuvering a sensor/probe to the heart through the blood vessels, or directly at surgery, then delivering energy to the cause(s) for the heart rhythm disorder to terminate it. Ablation was initially used for 'simple' disorders such as SVT, AFL, PVC, PAC, but is increasingly used for AF (Cappato, Calkins et al. 2005), VT (Reddy, Reynolds et al. 2007) and, to a lesser extent, VF (Knecht, Sacher et al. 2009).

However, ablation is often difficult because tools to identify and locate the cause of the heart rhythm disorder are poor, hindering attempts to deliver energy to the correct region to terminate and eliminate the disorder. In persistent AF, a highly prevalent form of AF, ablation has a one procedure success rate of only 50-60% (Cheema, Vasamreddy et al. 2006; Calkins, Brugada et al. 2007) despite lengthy 4-5 hour procedures and a 5-10% rate of serious complications (Ellis, Culler et al. 2009) including death (Cappato, Calkins et al. 2009). Even for 'simple' disorders such as atrial tachycardia, tools do not exist to make the diagnosis and suggest a likely successful ablation location.

Even the most sophisticated known systems display data that the practitioner must interpret, without directly identifying and locating the cause of the disorder to enable the practitioner to detect, diagnose and treat it. This includes currently used methods, described in U.S. Pat. Nos. 5,662,108, 5,662,108, 6,978,168, 7,289,843 and others by Beatty and coworkers, U.S. Pat. No. 7,263,397 by Hauck and Schultz, U.S. Pat. No. 7,043,292 by Tarjan and coworkers, U.S. Pat. No. 6,892,091 and other patents by Ben-Haim and coworkers and U.S. Pat. No. 6,920,350 by Xue and coworkers. These methods and instruments detect, analyze and display electrical potentials, often in sophisticated 3-dimensional anatomic representations, but still fail to identify and locate the cause of heart rhythm disorders, particularly for complex disorders such as AF. This is also true for patents by Rudy and coworkers (U.S. Pat. Nos. 6,975,900 and 7,016,719, among others) that use signals from the body surface to 'project' potentials on the heart.

Certain known methods for identifying and locating causes for heart rhythm disorders may work in simple rhythm disorders, but there are no known methods that have been successful with respect to identifying causes for complex disorders such as AF, VF or polymorphic VT. Activation mapping (tracing activation back to the earliest site) is useful only for simple tachycardias, works poorly for AFL (a continuous rhythm without a clear 'start'), and not at all for AF with variable activation paths. Entrainment mapping uses pacing to identify sites where the stimulating electrode is at the cause of a rhythm, yet pacing cannot be applied in AF and even some 'simple' rhythms such as atrial tachycardias due to automatic mechanisms. Stereotypical locations are known for the cause(s) of atrioventricular node reentry, typical AFL and patients with early (paroxysmal) AF, but not for the vast majority of patients with persistent AF (Calkins, Brugada et al. 2007), VF and other complex disorders. Thus, no methods yet exist to identify and locate the cause of complex heart rhythm disorders such as AF (Calkins, Brugada et al. 2007).

As an example of systems for 'simple' rhythms with consistent activation from beat to beat is given by U.S. Pat. No. 5,172,699 by Svenson and King. This system is based upon finding diastolic intervals, which can be defined in 'simple rhythms' but no complex rhythms such as atrial fibrillation (AF) or ventricular fibrillation (VF) (Calkins, Brugada et al. 2007; Waldo and Feld 2008). Moreover, this system does not identify or locate a cause, since it examines diastolic intervals (between activations) rather than activation itself. In addition, it is focused on ventricular tachycardia rather than AF or VF, since it analyzes periods of time between QRS complexes on the ECG.

Another example is U.S. Pat. No. 6,236,883 by Ciaccio and Wit. This invention uses a concentric array of electrodes to identify and localize reentrant circuits. Accordingly, this will not find non-reentrant causes such as focal beats. Moreover, this method of using feature and detection localization algorithms will not work for complex rhythms such as AF and VF, where activation within the heart changes from beat to beat. It identifies 'slow conduction within an isthmus of the reentry circuit', that are features of 'simple' arrhythmias such as ventricular tachycardia, but are not defined for AF and VF.

In a subsequent U.S. Pat. No. 6,847,839, Ciaccio and coworkers describe an invention to identify and localize a reentry circuit in normal (sinus) rhythm. Again, this will not find causes for an arrhythmia that are not reentrant but focal, from where activation emanates radially. Second, this patent is based on the presence in sinus rhythm of an "isthmus" for reentry, which is accepted for 'simple' rhythms with consistent activation between beats such as VT (see (Reddy, Reynolds et al. 2007)). However, this is not accepted for complex rhythms with varying activation paths such as AF or VF.

U.S. Pat. No. 6,522,905 by Desai is an invention that uses the principle of finding the earliest site of activation, and determining this to be the cause of an arrhythmia. This approach will not work for simple arrhythmias due to reentry, in which there is no "earliest" site in reentry because activation is a continuous 'circle'. This approach will also not work for complex arrhythmias in which activation varies from beat to beat, such as AF or VF.

However, even in simple heart rhythm disorders, it is often difficult to apply known methods to identify causes. For instance, ablation success for atrial tachycardias (a 'simple' disorder) may be as low as 70%. When surgeons perform heart rhythm disorder procedures (Cox 2004; Abreu Filho, 2005) it is ideal for them to be assisted by an expert in heart rhythm disorders (cardiac electrophysiologist). Thus, ablating the cause of a heart rhythm disorder can be challenging, and even experienced practitioners may require hours to ablate certain 'simple' rhythm disorders (with consistent beat-to-beat activation patterns) such as atrial tachycardia or atypical (left atrial) AFL. The situation is more difficult still for complex heart rhythm disorders such as AF and VF where activation sequences alter from beat-to-beat.

The prior art for diagnosing rhythm disturbances often measures times of activation at a sensor. However, such prior art has been applied to signals that, at each recording site, are quite consistent from beat to beat in shape and often timing. These prior art solutions are extremely difficult to apply to complex rhythms such as AF or VF where signals for each beat at any site ('cycle') may transition between one, several, and multiple deflections over a short period of time. When a signal, for instance in AF, comprises 5, 7, 11 or more deflections, it is difficult to identify which deflections is at the sensor ('local') versus a nearby site ('far-field'), as noted in studies to analyze AF rate (Ng and coworkers, Heart Rhythm 2006). In another recent report, signals in rhythms, such as AF, require 'interactive methods' to identify local from far-field activations (Elvan et al. Circulation: Arrhythmias and Electrophysiology 2010).

In the absence of methods to identify and locate causes for human AF, physicians have often turned to the animal literature. In animal models, localized causes for complex and irregular AF (induced by artificial means) have been identified and located in the form of localized 'electrical rotors' or repetitive focal beats (Skanes, Mandapati et al. 1998; Warren, Guha et al. 2003). In animals, rotors are indicated by signals that show a high spectral dominant frequency (DF) (a fast rate) and a narrow DF (indicating regularity) (Kalifa, Tanaka et al. 2006). Such uses of spectral dominant frequencies are described in U.S. Pat. No. 7,117,030 issued to Berenfeld and coworkers.

Unfortunately, these animal data have not translated into effective human therapy. Animal models of AF and VF likely differ from human disease. For instance, animal AF is rarely spontaneous, it rarely initiates from pulmonary vein triggers (that are common in human paroxysmal AF). Both AF and VF are typically studied in young animals without the multiple co-existing pathology (Wijffels, Kirchhof et al. 1995; Gaspo, Bosch et al. 1997; Allessie, Ausma et al. 2002) seen in older humans who typically experience these conditions.

In AF patients, sites where rate is high (or, sites of high spectral dominant frequency, DF) have not been useful targets for ablation. A recent study by Sanders and coworkers showed that AF rarely terminated with ablation at sites of high DF (Sanders, Berenfeld et al. 2005a). Other studies show that sites of high DF are common in the atrium, and ablation at these sites does not acutely terminate AF (as would be expected if high DF sites were causes) (Calkins, Brugada et al. 2007). In part, this may be because the DF method that is effective in animals may be inaccurate in human AF for many reasons, as shown by many workers (Ng, Kadish et al. 2006; Narayan, Krummen et al. 2006d; Ng, Kadish et al. 2007). Nademanee and coworkers have suggested that signals of low amplitude with high-frequency components (complex fractionated atrial electrograms, CFAE) may indicate AF causes (Nademanee, McKenzie et al. 2004a). This diagnostic method has been incorporated into commercial systems by Johnson and Johnson/Biosense. However, this method has also been questioned. Oral and coworkers showed that ablation of CFAE does not terminate AF or prevent AF recurrence alone (Oral, Chugh et al. 2007) or when added to existing ablation (Oral, Chugh et al. 2009).

Several inventions in the prior art acknowledge what was felt true until now—that AF is a "cardiac arrhythmia with no detectable anatomical targets, i.e., no fixed aberrant pathways," such as U.S. Pat. No. 5,718,241 by Ben-Haim and Zachman. This patent, as a result, does not identify and locate the cause for a heart rhythm disorder. Instead, it focuses treatment on heart geometry by delivering lines of ablation to "interrupt each possible geometric shape." This patent creates maps of various parameters of the heart.

Many inventions use surrogates for the actual cause for a cardiac arrhythmia, without identifying and locating said cause. For instance, U.S. Pat. No. 5,868,680 by Steiner and Lesh uses measures of organization within the heart, that are constructed by comparing the activation sequence for one activation event (beat) to the activation sequence for subsequent beats, to determine if "any spatiotemporal order change has occurred". However, that invention assumes that organization is greatest near a critical site for AF and is lower at other sites. However, this assumption may not be correct. In animal studies, indexes of organization fall with distance from an AF source, then actually increase again as activation re-organizes at more distant sites (Kalifa, Tanaka et al. 2006). Moreover, U.S. Pat. No. 5,868,680 requires more than one beat. As a result, methods such as U.S. Pat. No. 5,868,680 identify many sites, most of which most are not causes of AF. This lack of identifying and locating a cause for AF may explain why methods based on organization have not yet translated into improved treatment to acutely terminate AF. Similarly, U.S. Pat. No. 6,301,496 by Reisfeld is based on the surrogate of mapping physiologic properties created from a local activation time and vector function. This is used to map conduction velocity, or another gradient function of a physiologic property, on a physical image of the heart. However, this patent does not identify or locate a cause of a heart rhythm disorder. For instance, multiple activation paths in AF mean that the conduction path and thus conduction velocity is not known between the points used for triangulation. In addition, in the case of a rotor, activation sequences revolving around, or emanating symmetrically from, a core region may produce a net velocity of zero.

For these reasons, experts have stated that "no direct evidence of electrical rotors has been obtained in the human atria" in AF (Vaquero, Calvo et al. 2008). Thus, while it would be desirable to identify (and then locate) localized causes for human AF, this is not currently possible.

For human AF, particularly persistent AF, the absence of identified and located causes means that ablation is empiric and often involves damage to approximately 30-40% of the atrium that could theoretically be avoided if the cause(s) were identified and located for minimally invasive ablation and/or surgical therapy (Cox 2005).

Human VT or VF are significant causes of death that are poorly treated by medications (Myerburg and Castellanos 2006). Treatment currently involves placing an implantable cardioverter defibrillator (ICD) in patients at risk, yet there is increasing interest in using ablation to prevent repeated ICD shocks from VT/VF (Reddy, Reynolds et al. 2007). Identifying and locating causes for VT may be difficult and ablation is performed at specialized centers. In VF, animal data suggest that causes of VF lie at fixed regions near His-Purkinje tissue (Tabereaux, Walcott et al. 2007), but again this is very poorly understood in humans. The only prior descriptions of identifying and locating causes for VF required surgical exposure (Nash, Mourad et al. 2006) or were performed in hearts removed from the body after heart transplant (Masse, Downar et al. 2007)). Thus, minimally invasive ablation for VF focuses on identifying its triggers in rare cases (Knecht, Sacher et al. 2009) but cannot yet be performed in a wider population.

Existing sensing tools are also suboptimal for identifying and locating cause(s) for complex disorders such as AF, including single or multi-sensor designs exist (such as U.S. Pat. No. 5,848,972 by Triedman et al.). However, such tools typically have a limited field of view that is inadequate to identify causes for AF, that may lie anywhere in either atria and vary (Waldo and Feld 2008). Alternatively, they may require so many amplifiers for wide-area sampling that they are impractical for human use. Wide area sampling is advantageous and, in animals, is achieved by exposing the heart surgically (Ryu, Shroff et al. 2005) or removing it from the body (Skanes, Mandapati et al. 1998; Warren, Guha et al. 2003). In humans, even surgical studies only examine partial regions at any one time (for instance (Sahadevan, Ryu et al. 2004)), and introduce problems by exposing the heart to air, anesthesia and other agents that may alter the rhythm disorder from the form that occurs clinically.

Thus, prior methods have largely focused on mapping of the anatomy to identify whether a patient has a heart disorder, rather than determining the cause or source of the disorder. Thus, there is an urgent need for methods and tools to directly identify and locate causes for heart rhythm disorders in individual patients to enable curative therapy. This is particularly critical for AF and other complex rhythm disorders for which, ideally, a system would detect localized causes for ablation by minimally invasive, surgical or other methods.

SUMMARY

The present invention discloses systems, assemblies and methods to facilitate reconstruction of cardiac information representing a complex rhythm disorder associated with patient's heart to indicate a source of the heart rhythm disorder. The complex rhythm disorder can be treated by application of energy to modify the source of the rhythm disorder.

This invention is a significant advance over the prior art. For example, unlike U.S. Pat. No. 5,718,241, our invention identifies and locates causes (targets) for AF and other rhythm disorders that may stay at approximately the same location within the heart for hours (see our example in a 47-year-old man). Unlike U.S. Pat. No. 6,847,839, the present invention is able to identify sources that transiently appear or may move (they are "functional"), which may explain the variations in AF. Unlike U.S. Pat. No. 5,868,680, our invention directly identifies and locates cause(s) for a heart rhythm disorder, using as little as one activation event (beat) as shown in our examples. Unlike U.S. Pat. No. 6,301,496, our invention directly identifies and locates electrical rotors, in which activation revolves around a core region, or focal beats with activation radiating radially therefrom.

In one aspect of the invention there is provided a system to reconstruct cardiac information representing a complex rhythm disorder associated with a patient's heart to indicate a source of the complex rhythm disorder, the system including: at least one computing device configured to: receive cardiac information signals from the patient's heart during the complex rhythm disorder; classify the cardiac information signals into high and low confidence signals, wherein the high and low confidence signals are separated by a confidence threshold; determine activation onsets associated with the low confidence signals within an acceptance window; order the activation onsets associated with the low confidence signals and activation onsets associated with the high confidence signals; and output the activation onsets associated with the high and low confidence signals to indicate a source of the complex cardiac rhythm disorder.

In another aspect of the invention there is provided an assembly to facilitate reconstruction of cardiac information representing a complex rhythm disorder associated with a patient's heart to indicate a source of the complex rhythm disorder, the assembly including: a catheter comprising a plurality of sensors configured to provide cardiac information signals; and a computer-readable medium operatively couplable to the sensors, the computer-readable medium comprising instructions, which when executed by a computing device, cause the computing device to reconstruct cardiac information representing a complex rhythm disorder associated with a patient's heart to indicate a source of the complex rhythm disorder by: receiving cardiac information signals from a plurality of sensors during the complex rhythm disorder; classifying the cardiac information signals into high and low confidence signals, wherein the high and low confidence signals are separated by a confidence threshold; determining activation onsets associated with the low confidence signals within an acceptance window; ordering the activation onsets associated with the low confidence signals and activation onsets associated with the high confidence signals; and outputting the activation onsets associated with the high and low confidence signals to indicate a source of the complex cardiac rhythm disorder.

In yet another aspect of the invention there is included a method of reconstructing cardiac information representing a complex rhythm disorder associated with a patient's heart to indicate a source of the complex rhythm disorder, the method including: receiving cardiac information signals from a plurality of sensors during the complex rhythm disorder; classifying, by a computing device, the cardiac information signals into high and low confidence signals, wherein the high and low confidence signals are separated by a confidence threshold; determining, by the computing device, activation onsets associated with the low confidence signals within an acceptance window; ordering, by the computing device, the activation onsets associated with the low confidence signals and activation onsets associated with the high confidence signals; and outputting, by the computing device, the activation onsets associated with the high and low confidence signals to indicate a source of the complex cardiac rhythm disorder.

In another aspect of the invention there is provided a system to reconstruct cardiac signals associated with a complex rhythm disorder received over a plurality of channels from a patient's heart, the system including: at least one computing device configured to: identify a plurality of discernible beats on high-confidence channels that are adjacent to a low-confidence channel, the discernible beats on the high-confidence channels corresponding to a non-discernible beat on the low-confidence channel; compute a vector between at least two activation onsets of the identified discernible beats on the adjacent channels through the non-discernible beat on the low-confidence channel; define a time interval associated with the non-discernible beat about a region where the wave path crosses the non-discernible beat, the time interval indicating how early the non-discernible beat can activate based on a previous beat on the low-confidence channel that has a selected or determined activation onset and how late the non-discernible beat can terminate based on at least one predetermined property; and select a possible activation onset during the defined time interval that is closest to the computed wave path for the non-discernible beat In another aspect of the invention there is provided an assembly to reconstruct cardiac signals associated with a complex rhythm disorder received over a plurality of channels from a patient's heart, the assembly including: a catheter comprising a plurality of sensors to receive the cardiac signals; and a computer-readable medium operatively couplable to the sensors, the computer-readable medium comprising instructions, which when executed by a computing device, cause the computing device to: identify a plurality of discernible beats on high-confidence channels that are adjacent to a low-confidence channel, the discernible beats on the high-confidence channels corresponding to a non-discernible beat on the low-confidence channel; compute a vector between at least two activation onsets of the identified discernible beats on the adjacent channels through the non-discernible beat on the low-confidence channel; define a time interval associated with the non-discernible beat about a region where the defined vector crosses the non-discernible beat, the defined time interval indicating how early the non-discernible beat can activate based on a previous beat on the low-confidence channel that has a selected or determined activation onset and how late the non-discernible beat can terminate based on at least one predetermined property; and select a possible activation onset during the defined time interval that is closest to the computed vector for the non-discernible beat.

In yet another aspect of the invention there is included a method a method of reconstructing cardiac signals associated with a complex rhythm disorder received over a plurality of channels from a patient's heart, the method including: identifying a plurality of discernible beats on high-confidence channels that are adjacent to a low-confidence channel, the discernible beats on the high-confidence channels corresponding to a non-discernible beat on the low-confidence channel; computing a vector between at least two activation onsets of the identified discernible beats on the adjacent channels through the non-discernible beat on the low-confidence channel; defining a time interval associated with the non-discernible beat about a region where the vector crosses the non-discernible beat, the time interval indicating how early the non-discernible beat can activate based on a previous beat on the low-confidence channel that has a selected or determined activation onset and how late the non-discernible beat can terminate based on at least one predetermined property; and selecting a possible activation onset during the defined time interval that is closest to the computed vector for the non-discernible beat.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIGS. 15A and 15B show other patient examples of localized causes of human AF detected with this invention. Electrical rotors are shown in two patients in the left atrium.

FIG. 16A shows a focal beat cause in the left atrium. FIG. 16B illustrates the activation trail with activation emanating radially therefrom.

FIG. 23A shows a two-dimensional representation of a matrix of sensors, where the sensors are shown as points or electrode positions superimposed on a cardiac atrial surface.

FIG. 23B shows time-varying cardiac signals obtained from nine (9) of the cardiac electrodes or sensors shown in FIG. 23A.

FIG. 23C shows the result of tagging activation onsets for beats in each of the raw signals shown in FIG. 23B in accordance with the systems and methods described herein.

FIG. 23D shows a reconstruction of the activation potential duration (APD), which starts at the activation onsets determined in FIG. 23C and extends for a specified time or decay thereafter.

FIG. 24A shows an example display obtained from the raw signals shown in FIG. 23B using conventional methods known in the art.

FIG. 24B shows an example display derived from the tagging of activation onsets in FIG. 23C, in which a rotor is shown.

FIG. 24C shows a display in which the tagged activation times determined in FIG. 23C and the reconstructed APD's determined in FIG. 23D are used to define the intersection between a depolarization line and a repolarization line. This intersection is the core of the rotor, where therapy can be delivered to treat the rhythm disorder.

DETAILED DESCRIPTION

Definitions

For purposes of this invention, the following definitions shall apply:

"Detecting/Diagnosing": The terms detecting and diagnosing a rhythm disorder are used interchangeably in this application.

"Activation time" means the time of activation onset for a given heart signal.

Figure 3:
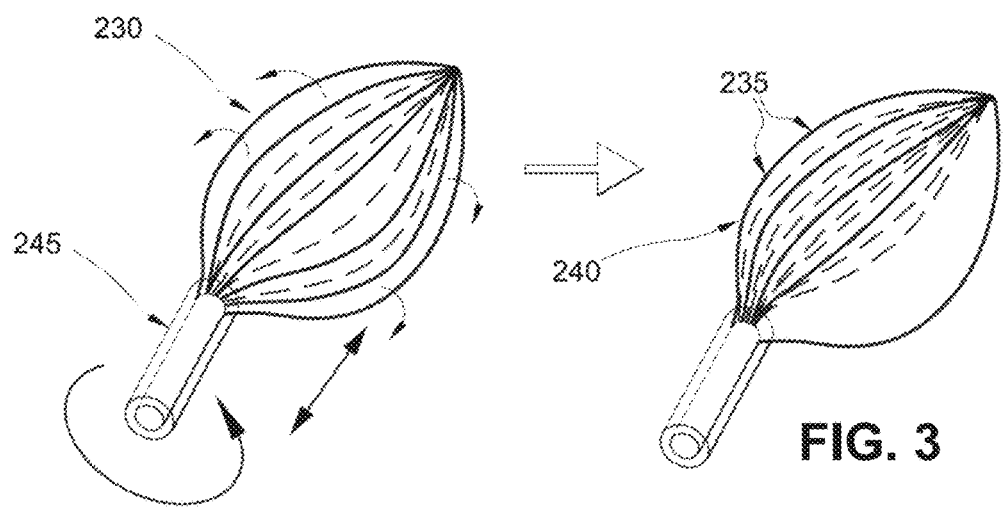
FIG. 3 shows another sensor apparatus design of the present invention that detects biosignals for a wide area of the heart chamber at low resolution, then for a narrower area at higher resolution.

"Activation time duration" means the time period and the signal waveform between the times of activation onset and offset for the signal of a given heart beat. Diastolic interval is the time period from activation offset of the prior beat to activation onset of the present beat (FIG. 3).

"Activation trail" means the ordering of the activation time onset at the sensor locations to create a discernible signature pattern, for example, including without limitation a rotational pattern around a core region indicative of a rotor, a radially emanating pattern from a core region, indicative of a focal beat cause, or a dispersed pattern, requiring further signal sampling and repeating of above analysis steps.

"Identify and locate" means the process of discerning the presence of a localized or dispersed cause of the heart rhythm disorder, then locating said cause relative to sensor locations or relative to known anatomic positions in the heart.

"Heart rhythm disorder" means an abnormal rhythm, often requiring treatment. These include without limitation, rapid rhythms of the top chambers of the heart (atria) such as rapid and abnormal activation of the normal sinus node (inappropriate sinus tachycardia or sinus node reentry), atrial tachycardia (AT), supraventricular tachycardia (SVT), atrial flutter (AFL), premature atrial complexes/beats (PAC) and the complex rhythms of atrial fibrillation (AF) and certain forms of atypical atrial flutter. Rapid rhythms can also occur in the bottom chambers of the heart (ventricles), including such as ventricular tachycardia (VT), ventricular fibrillation (VF), torsades de pointes and premature ventricular complexes/beats (PVC). Heart rhythm disorders can also be slow, including sinus bradycardia, ectopic atrial bradycardia junctional bradycardia, atrioventricular block and idioventricular rhythm.

"Cause of biological or heart rhythm disorder", which is used interchangeably with "source of the biological or heart rhythm disorder" in this application, refers to, without limitation, a rotational pattern of activation sequence around a core region indicative of a rotor, a radially emanating pattern from a core region indicative of a focal beat cause, or a dispersed pattern. In this invention, when a dispersed cause is found, signal sampling is extended to additional multiple locations and the detection and analysis steps of the invention are repeated. These causes are directly responsible for the perpetuation of the heart rhythm disorder.

"Sensor", which is used interchangeably with "electrode", refers to an apparatus for detecting and transmitting signals from the heart or to the heart.

Prior to the discovery of the present invention, the causes of human biological rhythm disorders, and particularly heart rhythm disorders, had not been identified. The present invention represents the first known instance where a method of detecting, diagnosing and subsequently effectively treating, in an accurate and minimally invasive manner, the cause(s) that sustain, perpetuate, or 'drive' human biological disorders has been described. This method enables the physician to target these sources for modification or elimination to abolish the disorder. Although one preferred embodiment is for minimally invasive procedures for heart rhythm disorders, the invention can also be applied to surgical therapy, and for disorders of electrical impulse generation or propagation in organs such as the brain, central nervous system (where it may locate causes of epilepsy or seizure), peripheral nervous system (where it may detect tumors), skeletal muscle and smooth muscle such as the gastrointestinal tract, bladder and uterus.

In accordance with an embodiment of the invention, there is disclosed an apparatus to sample signals, for example a sensor device such as an electrode catheter from multiple locations within a human organ, such as the human heart, at varying spatial resolutions and fields of view and with apparatus to alter the number of sensing channels accordingly.

In accordance with an embodiment of the invention, there is disclosed a method to identify and localize electrical rotors, focal beats and other localized causes for heart rhythms, including complex rhythms such as AF, VF and polymorphic VT.

Embodiments of the invention may use processes and software methods such as ordering the activation sequence to create an activation trail, processes such as the Hilbert transform, other phase delay methods, spatial coherence analysis and other methods.

In one embodiment of the invention, data collected from sensors and analyzed is stored as data in a database that is automatically updated. This database is used to assist the physician in the diagnosis/detection of localized causes, or to classify a pattern of causes of rhythm disorders. This may take the form of a probability distribution map of causes in patients with specific characteristics.

In accordance with another embodiment of the invention, there is provided an apparatus to display causes for the biological rhythm in a format that can assist the physician in treatment. For example, a visual display screen may be connected to a processor to allow for viewing of the activation trail and to allow for visual location of the core of a rotor, focal source or other cause of the disorder. Audio formats may also be used alone or in combination with the visual format. For example, in addition to or instead of the visual depiction of the source such that the core can be visually identified, the coordinates of the source and its core can be provided to the user by audio indications as to the location and cause of the disorder. Visual depiction is particularly desirable because it provides the practitioner with a clear representation of the cause and provides a reference for identifying the core of the cause, which greatly facilitates the selection of treatments. For example, a visual representation of the actual rotor or focal beat allows the practitioner to accurately determine where to direct the ablation catheter or other treatment.

In accordance with another embodiment of the invention, once the cause of the disorder is identified, use of a treatment device or method, to modify or destroy the site of an identified and localized source may be employed to treat or eliminate the rhythm disorder. Non-limiting examples of treatment devices and methods include the use of destructive energy (ablation) such as by ablation catheters, surgical ablation methods, surgical removal or using devices inside the heart such as implanted leads or other physical device, stimulating energy (pacing), direct delivery of pharmacologic agents, cellular therapy or other intervention techniques. In one embodiment, a catheter capable of sensing signals from the body, and particularly from the heart, may also include a means of treatment, such as the ability to delivery ablation energy, stimulation energy, drug therapy, cellular therapy such as stem cells or gene therapy, or other treatment means. Thus, such a catheter may be employed both in the detection and in the treatment of the disorder.

The present invention is particularly suited for the detection, diagnosis and treatment of complex heart rhythm disorders such as, for example, VF, polymorphic VT, torsade de pointes and AF, where once the localized cause is accurately identified and pinpointed, accurate and targeted ablation of the localized cause may be implemented. As discussed above, identification and physical location of the cause was previously not possible, and hence extraordinarily difficult even for experienced practitioners to treat successfully, much less substantially ameliorate or eliminate.

In addition to finding the cause of and subsequently treating complex heart rhythm disorders, the present invention may also be applied to help diagnose and treat 'simple' rhythms that emanate from a single site by accelerating and simplifying analysis for the practitioner. For heart rhythm disorders, such simple disorders include focal atrial tachycardias, multifocal atrial tachycardias (MAT), sinus nodal reentry or inappropriate sinus tachycardia, ventricular tachycardia (VT), premature atrial complexes (PACs) and premature ventricular complexes (PVCs).

Included in the invention are a process and system to collect data, including sensing devices and recording systems. The collected data includes at least the location of each sensor which transmitted one or more signals and the onset time at which each activation signal or activation time duration occurred. The processor receives this information and sequentially orders the activation onset times. The result of this computation is the creation of an activation trail which creates a signature pattern for the disorder and indicates both the location and the type of the cause to the disorder, i.e., whether it is a rotor, focal source or a dispersed pattern, i.e., no localized source, hence requiring further data to be collected from a different area of the heart or other body region. The data once ordered in this manner creates an activation trail which can visually be depicted on a visual display to show, in the case of a rotor source, the actual rotational pattern of the rotor such that the core of the rotor is visually apparent and can easily be identified and hence treated. The same hold true for the depiction of a radially emanating source, such as a focal beat. The sequential ordering of the activation onset times at each sensor permits the location of focal rhythm disorders, such that the focal core can be easily located on the visual display for targeted and accurate treatment. Desirably, the rhythm sources or causes are displayed over a period of time to allow the practitioner to fully observe the causal point or area and to make a comfortable assessment as to the appropriate treatment at the causal location. In one embodiment, the data and/or the visual displays of the processed data (i.e., a "movie" of the activation trail) elucidates the signature pattern of the cause of the rhythm disorder. Such stored information allows for the practitioner to consult previous patterns to aid in improving the identification, localization and treatment of similar causes. In some instances, such stored information allows for extrapolation of measured real-time data to provide predictive models or to clarify certain measured patterns using similar known patterns.

A further embodiment of the invention provides a process and system for the treatment of such causes, often by modification or destruction of tissue where causes reside. Sixth, a preferred embodiment enables the invention to be used in an 'offline', non-real-time review mode, rather than directly during a procedure to treat a patient.

The process and system of the invention may be employed to localize sources (i.e., find the physical location of the cause) for abnormal electrical impulse generation or propagation in the brain or central nervous system using the electroencephalogram or other index to guide invasive therapy (surgery) or external beam irradiation to identify and treat seizure or epileptic foci, or focal tumors (malignant or otherwise). The invention may also be used to identify sources for abnormal impulse propagation in striated muscle (such as injury in skeletal muscle), the gastrointestinal system (such as esophageal spasm), and the urogenital and respiratory systems. The invention may also be used to detect tumors (malignant or otherwise) in any body system. The invention also has applications outside of medicine, such as for locating the source of a seismic event or for locating energy sources in tandem with methods such as radar or sonar.

The invention has several aspects to its process and system for carrying out the process. By way of example and not of limitation, in one aspect of the invention, signals are detected from multiple locations in an organ in the rhythm disorder, altering the spacing between sensors to optimize clarity of said sensing. A particularly desirable embodiment also records these signals from a heart, or other body part, during a rhythm disorder and stores them in a data base. The location of each sensor associated with a particular signal, as well as the activation onset times at each sensor are transmitted to a processor for analysis including sequential ordering to form the activation trail identifying the cause of the disorder and its specific location in the body. Creating a database of causes, which may be manually or automatically updated allows for accessing the data base to assist in the identification and localization of disorder causes. This is used when data collection in the current patient is of limited quality, to compare the pattern in a patient to prior recorded rhythms in the patient to determine if the rhythm is the same or different, or to compare the pattern in a patient to that from another patient, such as one with similar clinical characteristics. Previously stored data from a previous case may be used to help identify, localize and display causes for the rhythm disorder in a present case.

Visually displaying the sources of the disorder is extremely useful to the practitioner because it serves as a visual guide to the existence and location of the cause, and permits subsequent targeted and accurate treatment to ameliorate or eliminate the rhythm disorder.

In other aspects of the invention, previously stored data from another case may be used to identify, localize and display causes for the rhythm disorder in a present case. This can then be used to plan the use of this invention in a future procedure.

Description of Useful Components, Modules, and Devices

Figure 1:
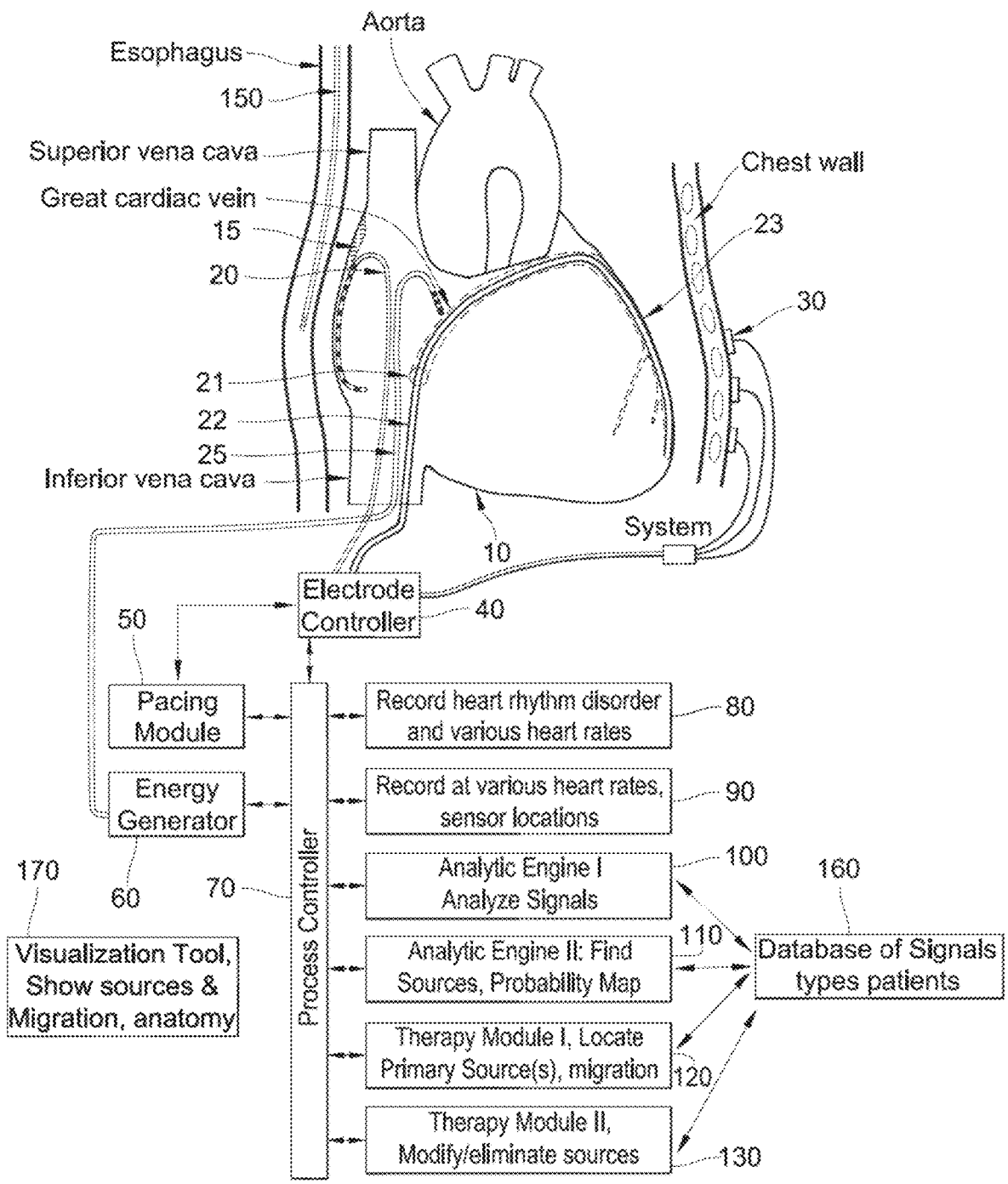
FIG. 1 is a depiction of the heart showing the use of sensors, ablation catheter and the electronic processing components of the present invention which processes signals from the heart and orders them in accordance with the invention.

FIG. 1 shows a schematic of various useful components (modules) that may be used in the process and system of the invention. The modules may be separate from each other and cooperatively interfaced to provide their function, or one or more of them may be integrated with each other or contained in the processor, such that the system has fewer separate hardware units. FIG. 1 depicts an embodiment that allows a cause of the disorder to be localized during a minimally invasive percutaneous procedure, or other procedures such as using surface ECG, a magnetocardiogram, echocardiographic and/or Doppler measurements from ultrasound, electromagnetic radiation, sound waves, microwaves, or electrical impedance changes.

In FIG. 1, electrical events in the heart 10 are recorded with sensing electrodes. These electrodes may be catheters 20 placed within the chambers or vasculature of the heart, including custom-designed recording catheters exemplified in FIGS. 2-4. The electrodes may also be extensions of leads from an implanted pacemaker or cardioverter-defibrillator, or catheters used to record monophasic action potentials or other signals, that typically arrive via the vena cavae or coronary sinus 22. Thus, although particularly useful in the invention, the process and system of the invention need not employ the specialized catheters of FIGS. 2-4, as any catheters or sensing devices used inside or outside of the body that are capable of accurately transmitting the activation times and location of their occurrence may be employed.

Electrodes 23 may record from the epicardial or pericardial surface of the heart, accessed via electrodes 21 in the coronary sinus, via the electrodes 23 in the pericardial space or other routes. Electrodes may be located in proximity to the nerves supplying the heart 15, which may be located in the left atrium and ventricles. Electrodes may be virtual (computed) electrodes from a computerized mapping system, routine or high-resolution ECG mapping electrodes 30, electrodes implanted under or on the skin, or derived from methods to non-invasively detect signals without directly contacting the heart or body. Electrode information may also be derived from stored electrograms in a database 160.

An electrode 25 placed near the heart may be used to modify or destroy regions that are near or at the cause(s) for a rhythm disorder. If the electrode is an ablation catheter, it interfaces to an energy generator 60. Other electrodes may interface with a controller 40, and a pacing module 50, and all desirably communicate with a process controller 70. Ablation or pacing can be directed to nerves supplying the heart 15, which are located at many locations of the heart. Internal ablation electrodes may be replaced with an external ablation system, such as external probes during surgery, or as in external focused irradiation or photon beam as for cancer therapy. In addition, modification of sources, i.e., treatment of the causes of the disorder, may be achieved by delivering appropriate pharmaceutical compositions, gene therapy, cell therapy, or by excluding tissue (at surgery or by using specialized devices).

The process controller 70 may include various components or modules. On such component or module includes a sampling module 80 which is capable of recording signals during the rhythm disorder, recording at various rates not in the rhythm disorder (by pacing), and/or recording during rates that simulate the heart rhythm disorder (by pacing or other methods). Signal amplifiers (not shown) may be used to enhance the signal clarity and strength, and the process controller may also intelligently assign the fewest number of recording amplifiers to sense from a sufficient number of locations to identify and localize the cause. For instance, the system may use only 50-60 physical amplifier channels to record from 128 sensors (for example, from two commercially available multipolar catheters), by recording those 128 sensors on a 'time-share' basis by time-slicing, or by activating individual/multiple sensors close to a rhythm cause while deactivating others. This 'switching' functionality may be performed by a switching component that connects the sensor device with the electronic control system, and that may be embodied in one or more other components. Switching may be manual or automatic, determined for instance on where causes of the heart rhythm disorder lie. Module 90 interfaces with the pacing module to provide additional heart rates for sensing the biosignal. This is particularly useful for the non-real time mode (mode 6), described herein, because it can study the heart at different heart rates even when not in the particular heart rhythm disorder being diagnosed and treated.

The inventive method and system processes the collected data using analytical methods, which may be performed by analytic modules. For example, in FIG. 1, Module 100 is part I of an "Analytic Engine." This portion of the Analytic engine determines the onset and offset for the biologic signal over time, at each sensed location. This is implemented by creating a series of activation times (onset timing) and recovery times (offset timing) during the rhythm over time (illustrated in FIG. 6). The signal is typically represented as voltage over time (that is, as a voltage-time series). Activation time can be processed in many ways. The simplest includes manual assignment at each location. Automated or calculated assignment can be achieved by using zero of the first derivative to define maxima or minima, zero of the second derivative to indicate maximum upstroke or downstroke, or similar methods. Activation onset and offset times can also be assigned when the voltage time-series crosses a threshold. Another possible method to assign activation times is using pattern-matching. For instance, a pattern selected to represent the activation duration can be correlated to the signal at multiple timepoints over time. The time when said correlation values are high indicate recurrences of said template, and thus are considered activation times. The template used for this analysis can also be obtained from stored data in a database, or computed from a rate estimate for the rhythm at that location. Simultaneous recordings from multiple sensors can help in analyzing activation, particularly for complex rhythms such as AF or VF when signal quality may be noisy, of poor quality or show multiple components at different times. From simultaneous recordings, a reference signal is selected, preferably at a nearby location to the channel being analyzed. Signals on the reference channel are used to select signal or signal components on the channel being analyzed. This can be done by using components that retain a similar timing over time, using pattern matching or correlation functions, vectorial analysis or other methods. If many methods are required, heuristics, pattern recognition methods and so-called 'fuzzy logic' approaches can be applied, constrained by known pathophysiology of the atrium.

Module 110 is part II of the Analytic Engine that actually computes and localizes, i.e., determines the existence and location of sources (causes) for the heart rhythm disorder.

Some embodiments of the invention include a "Therapy Engine," which may contain one of more modules designed to cooperatively perform different functions in the system and process. For example, module 120 in FIG. 1 may be responsible for determining the location and migration pattern of sources for the rhythm disorder within the heart. This may be a first module of the Therapy Engine, and is used to compute the location and spatial region which is required to be modified in order to treat or eliminate the rhythm disorder. Treatment may be by delivery of ablation energy or other means as discussed herein, and is not simply one point or region if the source migrates during ablation. Module 130 is representative of another module of the Therapy Engine, and desirably directly interfaces with the energy generator to ablate (destroy), modify (ablate or pace) or stimulate (pace) tissue at sites likely to represent sources. Alternatively, the Module 130 may be used to modify tissue without destructive energy, for example by delivering pharmaceutical agents, or gene or cellular therapies.

Module 170 of the system shown in FIG. 1 is representative of a tool to display the identification or location of causes visually or in auditory fashion, to assist the physician in treating or eliminating the rhythm disorder. For example, this module may include a display screen which permits the textual, graphic and/or auditory visualization on the screen of the rotor, focal or other cause of the disorder to be clearly seen by the practitioner. In some embodiments, a "movie" clip of the disorder found will be presented on the screen. This clip is a real-time presentation of the actual cause and location of the disorder. For example, once the analysis of the data has been performed in accordance with the process of the invention, i.e., the location of the signals and their activation onset times have been sequentially ordered, the result of this analysis and computation will be shown on the screen in the form of an activation trail. If the pattern of the activation trail signifies a series of activations revolving around a central core, then a rotor has been found and is in fact a cause of the disorder. Similarly, if the pattern of the activation trail signifies a series of activations which emanate radially from a central core region, then a focal beat has been found and is in fact a cause of the disorder. Thus, the inventive process permits the direct finding of the cause of the disorder and the convenient visualization of the existence, type and location of the disorder for the practitioner. In the event that no discernible pattern is found, i.e., the activation trail is not localized, then additional signal sampling by moving the sensor locations and/or turning-on already placed sensors may be appropriate. The additional signal samples may then be processed in accordance with the invention and shown on the screen. If a cause is found via the additional sampling and processing of the data, then a decision as to the appropriate treatment may be made. In the event that a dispersed activation trail and pattern is found, further additional sampling may be advisable until such time as the practitioner feels is sufficient. In some instances, the result of the process will render a finding of the existence and location of a rotor or a radially emanating focus. In other instances, where a dispersed pattern remains even after repeated sampling and processing, a diagnosis may be made ruling out a rotor or focal beats as the cause. Thus, the finding of a rotor or a focal point (beat) will be essentially a detection and diagnosis concurrently, whereas the lack of such a finding will be a diagnosis which may rule out the presence of either of these causes of the disorder.

Mode 1. Signal Sampling (FIG. 1, Reference 80)

Signal sampling can be done in real time, during a procedure to ablate or treat the rhythm disorder, beforehand to plan for a procedure, or afterwards to review the disorder. As stated above, signals are collected at one or more locations from the organ using a variety of sensor types. Contact sensors should maintain as good a contact with the tissue as possible. In the preferred mode, electrodes should record at multiple sites simultaneously or nearly simultaneously. The fastest heart rhythm disorders such as AF have cycle lengths >100 ms, so that signal acquisition for substantially less than this time is considered 'nearly simultaneous'. An alternative mode of operation allows moving a sensor to sequential sites. The invention may be used with any existing sensor apparatus.

Figure 2:
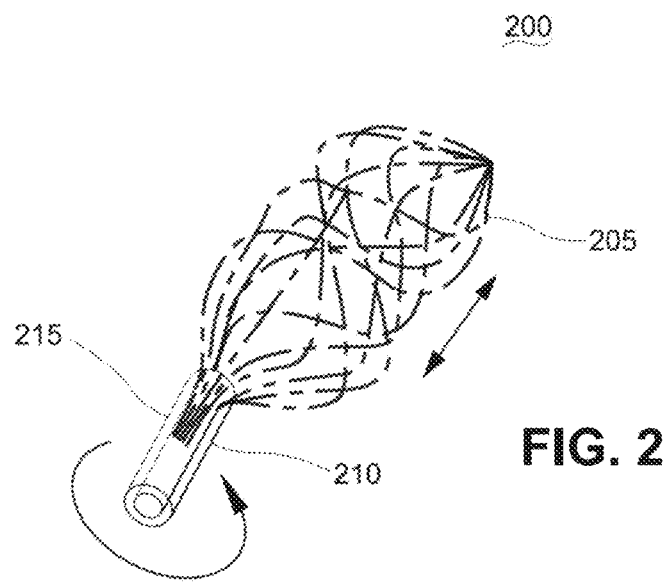
FIG. 2 shows a sensor apparatus design of the present invention that detects biosignals for a wide area of the heart chamber at low resolution, then for a narrower area at higher resolution.
Figure 4:
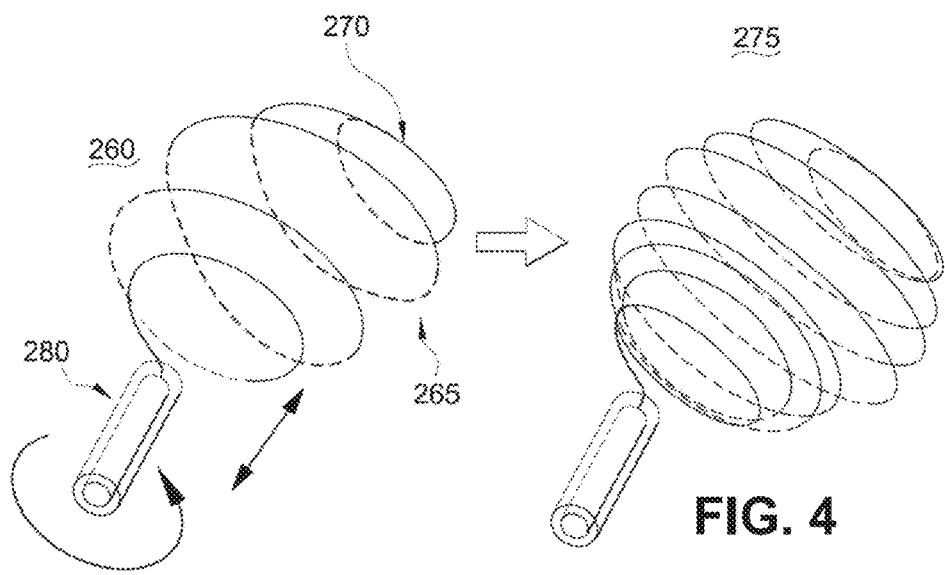
FIG. 4 shows another sensor apparatus design of the present invention that detects biosignals for a wide area of the heart chamber at low resolution, then for a narrower area at higher resolution.

Although a variety of commercially available electrode devices may be used to obtain signal sampling, particularly useful device embodiments for signal sampling are shown in FIGS. 2-4. These apparatuses use multiple sensors that may be individually activated or deactivated, or moved relative to one another. This enables adaptive spatial resolution, in that sensor spacing can be increased or decreased as desired. Widely-spaced sensors provide a wide field of view to 'survey' the rhythm for a large portion of the organ (e.g., left atrium of the heart). Once the source location is approximated, the configuration is desirably altered to reduce sensor spacing for higher spatial resolution over a narrow field of view. A tightly spaced sensor configuration is preferred for applying energy to a focused region to treat a source.

Adaptive spatial resolution is an important advantage of various embodiments of the present invention. This can be achieved by physically moving sensors. FIG. 2 shows concentric helices (element 200), with multiple sensing elements (electrodes or probes) for sensing signals and in some instances delivering energy or other treatment therapy (element 205). The helices are widely spaced when parts of the catheter remain non-deployed (element 210) inside the shaft (element 215). Rotating and advancing the assembly introduces more probes in the chamber, and reduces their spacing. FIG. 3 another embodiment of an inventive sensor catheter in the form of an adjustable fan catheter, with multiple meridians (element 230) each containing multiple sensing elements (electrodes or probes) (elements 240), also for sensing and in some instances for delivering energy or other treatment therapy. By a combination of twisting or torsional motion along the shaft axis (element 245), as depicted in the figures, the meridians may be more widely spaced (element 230) or more closely spaced (element 235), i.e., spatially adjusted. FIG. 4 shows another embodiment of an inventive sensor catheter in the form of an adjustable corkscrew design, with a small number of spiral meridians (element 260) ending on a blunt non-traumatic end (element 270). As with the design structures of FIGS. 2 and 3, the meridians of FIG. 4 may include multiple elements (electrodes or probes) (elements 265). The corkscrew can be advanced or retracted into the sheath by manipulating the shaft (element 280), to increase or decrease the corkscrew size and/or probe spacing. These designs can be made larger or smaller to fit a larger or smaller organ (e.g., atria of varying sizes), or substructures including pulmonary veins or the superior vena cava that may be sources for rhythms such as AF. Physical movement can be achieved manually by the physician or automatically by using machines. Given the observed properties of sources for heart rhythm disorders, it is desirable that the sensors sense from at least about 25% of the surface area of each one or more chambers of the heart. These designs are illustrative only, and are not intended to limit the actual physical design or application of this invention.

Optimal contact for each sensor can be monitored by the process controller 70 for adequacy in various ways. For example, the process controller 70 can verify contact via stability in the amplitude of sensed signals. Alternatively, the process controller 70 can condition the pacing module 50 to emit signals through electrodes 20-30, and use the amplitude of evoked responses to verify contact. As a third alternative, the process controller 70 can determine contact by confirming stable tissue impedance (in AF, for instance, where pacing is not possible). As other alternatives, catheters designed to examine mild injury patterns, or designed to directly measure contact force, can be used. In addition, catheter manipulation can be controlled robotically in semi-automated or automated fashion, as well as manually.

Adaptive spatial resolution can also be achieved electronically. Sensors in this adjustable sensor device are connected to an electronic control system that may activate or deactivate individual sensors. This may be performed manually, such as if the physician wishes only to focus on one region of the organ, or automatically by the process controller in FIG. 1 to focus on a region determined to be where the heart rhythm source lies. An electronic switching apparatus controls independent switching of connections between the sensors and electronic control system, in order to maximize use of a practical number of amplifier channels. These electronic components may be embodied by various combinations of traditional (wired) electrodes, fiber optics, etched-wafer circuit designs, biologic sensors, chemical sensors, pharmaceutical sensors, piezoelectric sensors, infrared sensors, patient-compliant optical imaging, optrodes, remote sensors and other designs.

Electronic switching may also be achieved by time-slicing. A large number of locations may need to be sensed, but the number of sensing channels may be limited. Signal time-slicing can record a larger number of sensing channels from a smaller number of channels. For instance, signals are often sampled every 1 ms (at 1 kHz) although data acquired every 10 milliseconds (ms) or so is often sufficient for AF or VF source analysis. Thus, the system can sense at location 1 for 3 ms, locations 2 and 3 for 3 ms each, then return to sensor 1 to repeat the cycle at the 10 ms timepoint. In this way, 90 locations can be sensed using 30 channels. Any appropriate configuration can be used, depending on the switching time in hardware or software, and allowing for noise factors when switching between channels. Many other methods can be used to increase the effective number of channels, including sending multiplexed signals along a fiber optic or other device, or storing signals in random access memory, then using off-line analysis to amplify and analyze each in turn.

Numbers of sensed locations can also be increased using a combination of sensors lying in contact with different heart planes. For instance, electrodes on the endocardial (inner) surface of the heart may be complemented by electrodes on the epicardial (outer) surface and possibly those in the heart muscle itself (via implanted electrodes) to increase overall spatial resolution. This is of particular value in the atrium, whose wall is thin and where epicardial and endocardial electrodes may target similar regions. In the ventricle, or in thick walled regions of the atrium, different planes may provide different information.

In certain preferred embodiments, sensing can be performed using one or more sensors (probes) moved sequentially within the organ during the heart rhythm disorder.

When a single probe is used, signals from each location are aligned relative to a timing signal fiducial. This method is easy to apply when a rhythm is relatively regular within the heart, such as the 'simple' disorders of focal atrial tachycardia or atrial flutter. However, this method can also be used as an approximate guide if the rhythm is irregular within the heart, such as the complex rhythms of AF or VF. This has the advantage of requiring fewer sensors, and will work if sources show some stability in space. For instance, while AF is irregular, activation may be regular at localized sources, for example at certain locations such as near the pulmonary veins.

One particularly useful embodiment for using sequential sensing at multiple locations is now illustrated for a moving probe with two sensors (such as the two bipoles of a clinical quadripolar catheter), although more sensors may be applied if available. At each location, one sensor is considered the reference and the onset times for successive cycles (beats) are fiducials. The difference in activation time at the second sensor is used to indicate relative timing. The probe is now moved so that one sensor overlies the previously sensed location. The second sensor now senses a fresh location and can record relative timing onsets for multiple beats here. The process is repeated for the entire region of interest. Because this process introduces stability in relative timing between locations, variability can be reintroduced stochastically using observed beat-to-beat timing variations at each location.

An alternative approach is to use gradients in rate and/or organization within the chamber, compared to stored data from a database for that rhythm (including AF or VF). After sensing sequential locations, the activation rate in both chambers is compared to stored patterns that describe this relationship at various sources (rotors or focal beats) and surrounding sites. An error-minimization approach (such as least-square-errors) may be used to estimate the source location. Estimates may be refined adaptively, based on similarity to subsets of stored patterns and using algorithmic, heuristic, fuzzy logic or other pattern recognition scheme. This process is repeated iteratively. For a spatially consistent source, second and subsequent iterations will add precision to the original estimate, and may be focused at locations closest to the estimated source.

Delivery of treatment therapy may be another feature of the sensor device, that will be described in detail later herein.

Mode 2. Computing Causes of Heart Rhythm Disorders

Figure 5:
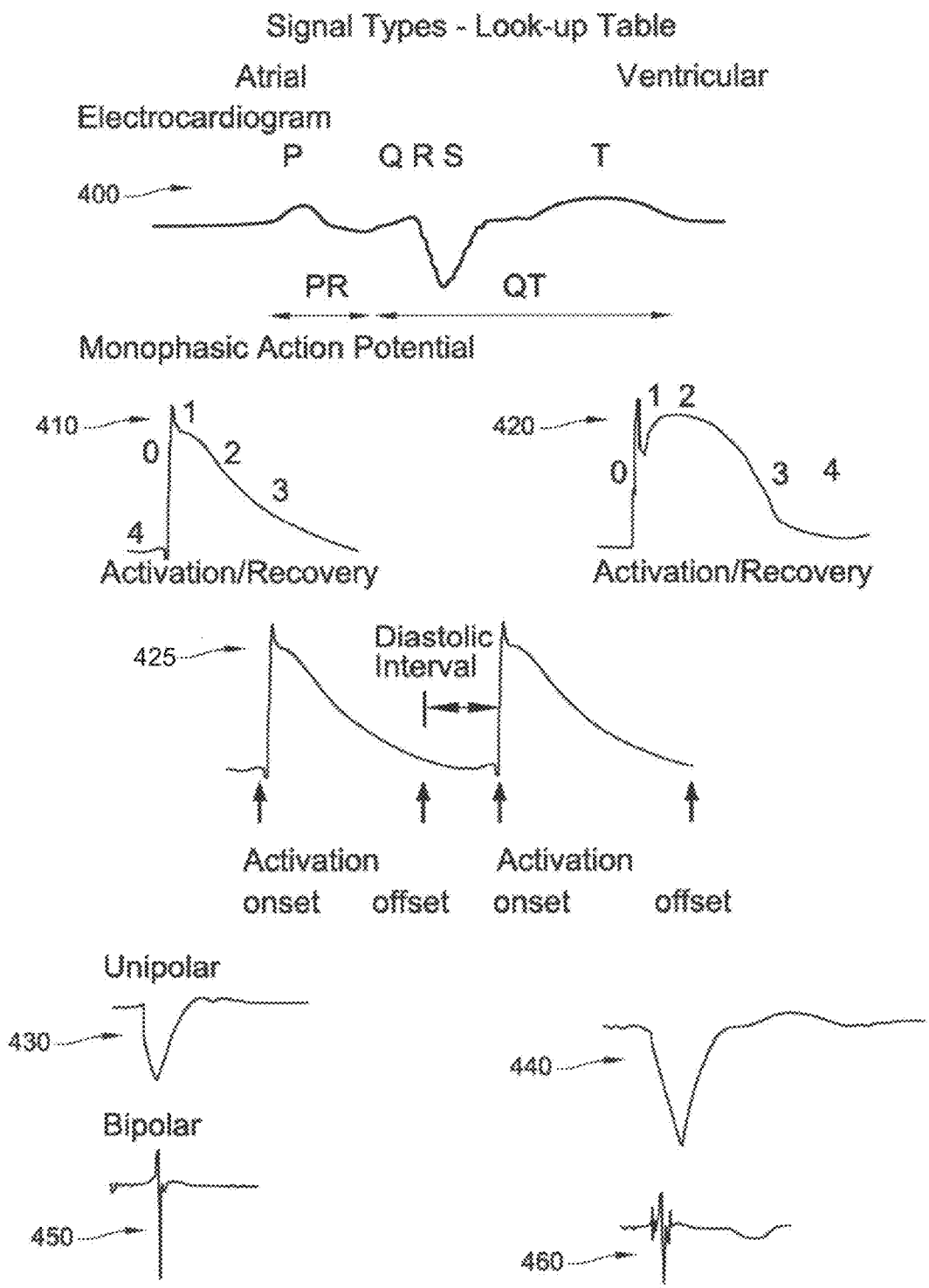
FIG. 5 illustrates some signal types from the heart to be analyzed by the invention, and defines some selected terms including activation onset, activation offset and diastolic interval.

The first step in analysis is to determine the signal type, using a lookup table as illustrated in FIG. 5, reference numerals 400-460. This step determines if the signal arises from the heart (cardiac), brain, respiratory system, gastrointestinal tract, urogenital system, and so on. If cardiac, the signal may be a surface ECG, intracardiac, echocardiographic or other signal. If intracardiac, the signal is further classified as an action potential (monophasic action potential), bipolar electrogram, unipolar electrogram or other. Some of these signals provide high quality information (e.g., monophasic action potential recordings in the heart), while others do not. Lower quality signals are more likely to require pre-processing, filtering, averaging, comparison against stored signals in a database, in that patient at different times and other computational steps to allow source localization.

Figure 6:
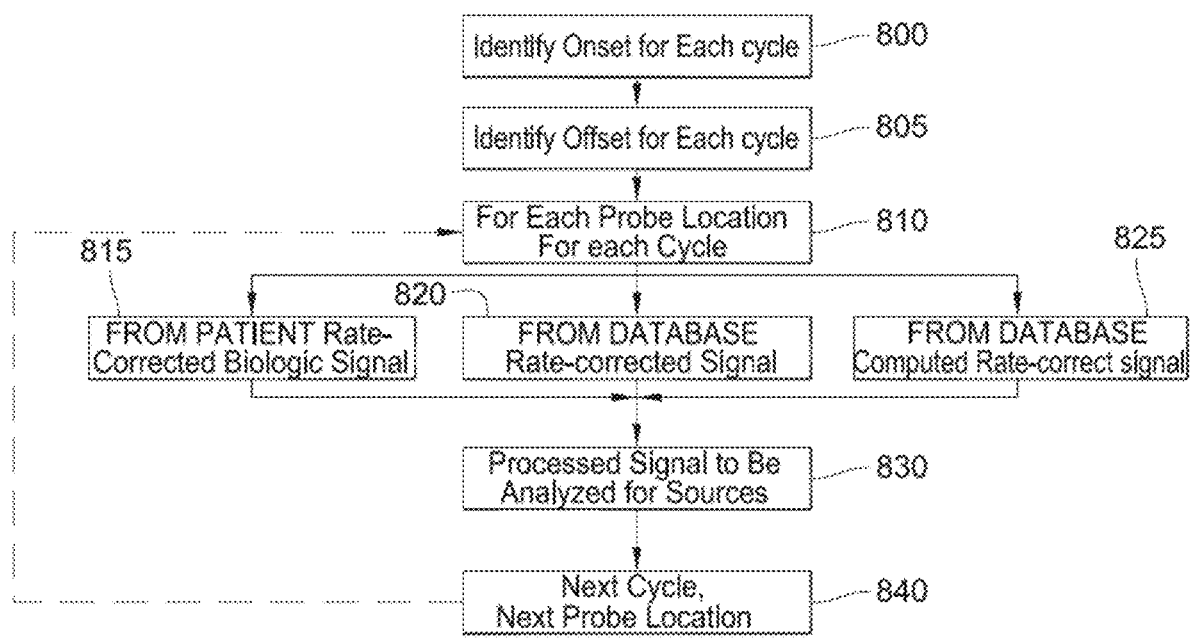
FIG. 6 is a flowchart showing analysis of signals at multiple locations to identify and locate causes for biological rhythm disorders in accordance with the present invention.

In FIG. 6, the signal is parsed between steps 800-840 to identify its type in the lookup table (from FIG. 5). This includes assigning activation onset and offset, and the interval between beats (diastolic interval) that depends upon the signal type illustrated in the lookup table in FIG. 5. The lookup table can be a comprehensive biosignal inventory, with data on the distinct physiological role of each component for computational purposes. Components may vary with rate and may fluctuate from beat to beat. Each signal component may reflect a distinct aspect of normal or abnormal physiology and thus indicate likelihood that the rhythm disorder may arise. Examples are not intended to limit the scope of the lookup table, which may include signals from other muscles (e.g., skeletal muscle, bladder and gastrointestinal tract), the brain and the nervous system.

The next step in analysis is to define, for each sensed location, the physiological signal to be analyzed. The goal is that the resulting signal best represents actual physiological activation and recovery occurring in the heart rhythm disorder at each location. When the recorded signal is 'clean' (has a high signal-to-noise ratio), this will be the physiological signal. If signals are noisy, then filtering, noise reduction and other schemes may be needed to reveal the physiological signal. Said noise schemes may require recording while the patient holds his/her breath for several seconds. For analysis of atrial rhythm disorders, the physiological signal is best recorded between ventricular activations (in the R-R interval), that may be facilitated if the heart beat is reduced (R-R interval is prolonged) using agents to slow ventricular rate or by reducing pacemaker rate in patients with such devices.

Figure 7A:
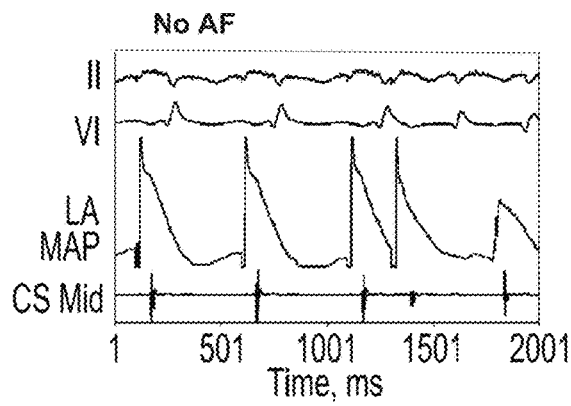
FIGS. 7A-7G illustrate computation of rate-behavior (restitution) curves for human signals, with insertion of physiological patterns in some cases.
Figure 7B:
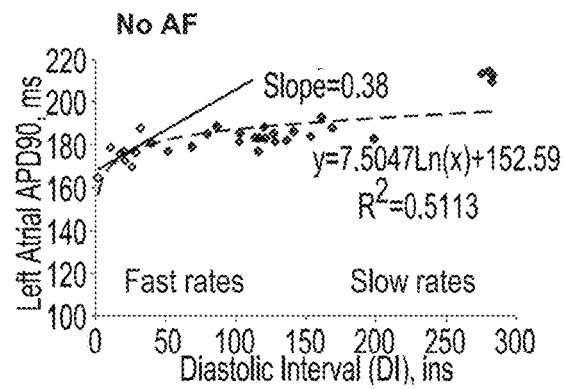
Figure 7C:
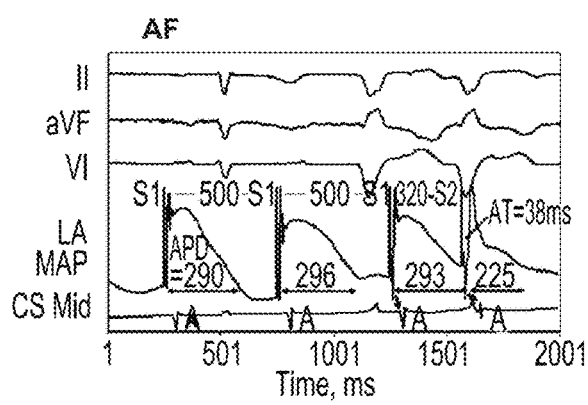
Figure 7D:
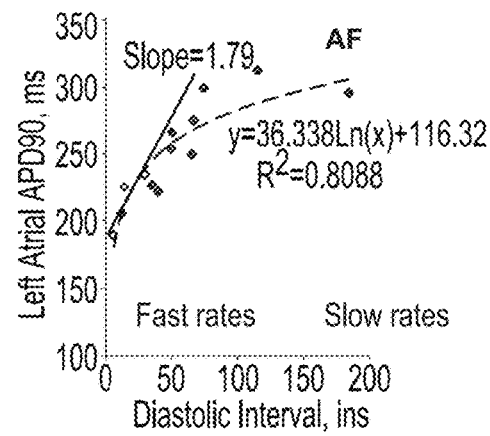
Figure 7E:
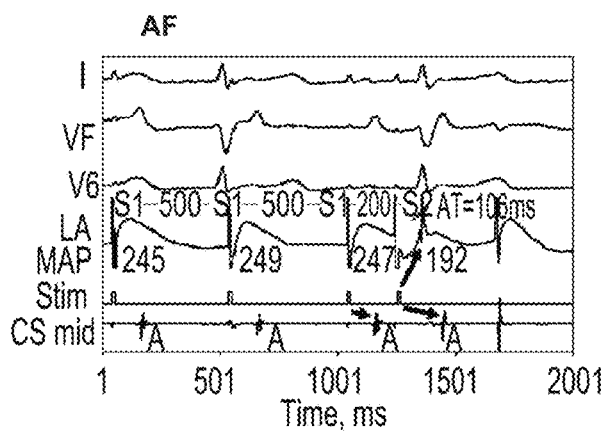
Figure 7F:
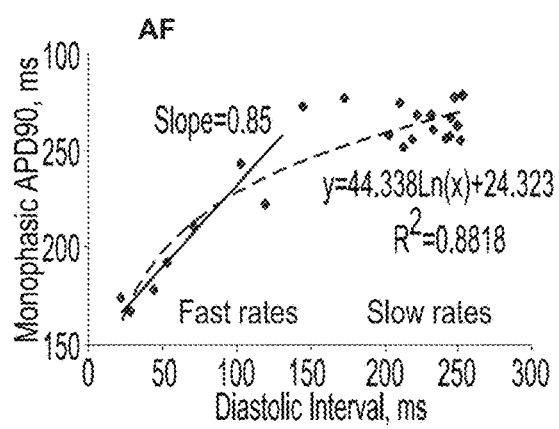

FIGS. 7A-7G illustrate a particularly useful embodiment for constructing physiological signals using computational methods to compensate for limitations due to noisy or low quality data. First, the response to rate of each signal type (monophasic action potentials, MAP, illustrated in FIGS. 7A (patient without AF), 7C (AF patient) and 7E (AF patient)) is determined. This is performed by sensing signals at varying rates when in the rhythm disorder, or when not in the rhythm disorder (such as by pacing, see mode 6, discussed below). The response of the signal duration (illustrated for MAP) to varying rate is shown in FIGS. 7B, 7D and 7F. FIG. 7B (no AF) shows no shortening with rate, while, with AF, FIGS. 7D and 7F show that MAP shortens at increasing rate (that is, when diastolic interval shortens). It is to be noted that the response to the same set of rates may vary when the patient is and is not in the heart rhythm disorder. FIGS. 8A-8E show this. Pacing with delivery of a single extra beat in FIG. 8A results in the restitution plot shown in FIG. 8B as soon as AF begins. However, after several minutes, the restitution curve changes as shown in FIGS. 8C-8E.

Figure 7G:
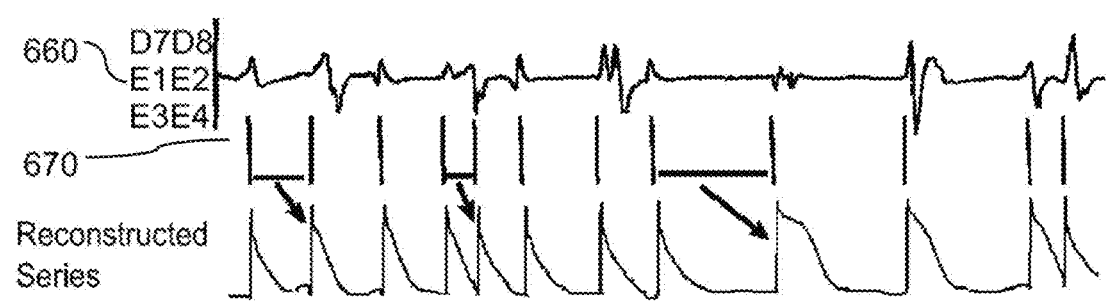
Figure 8A:
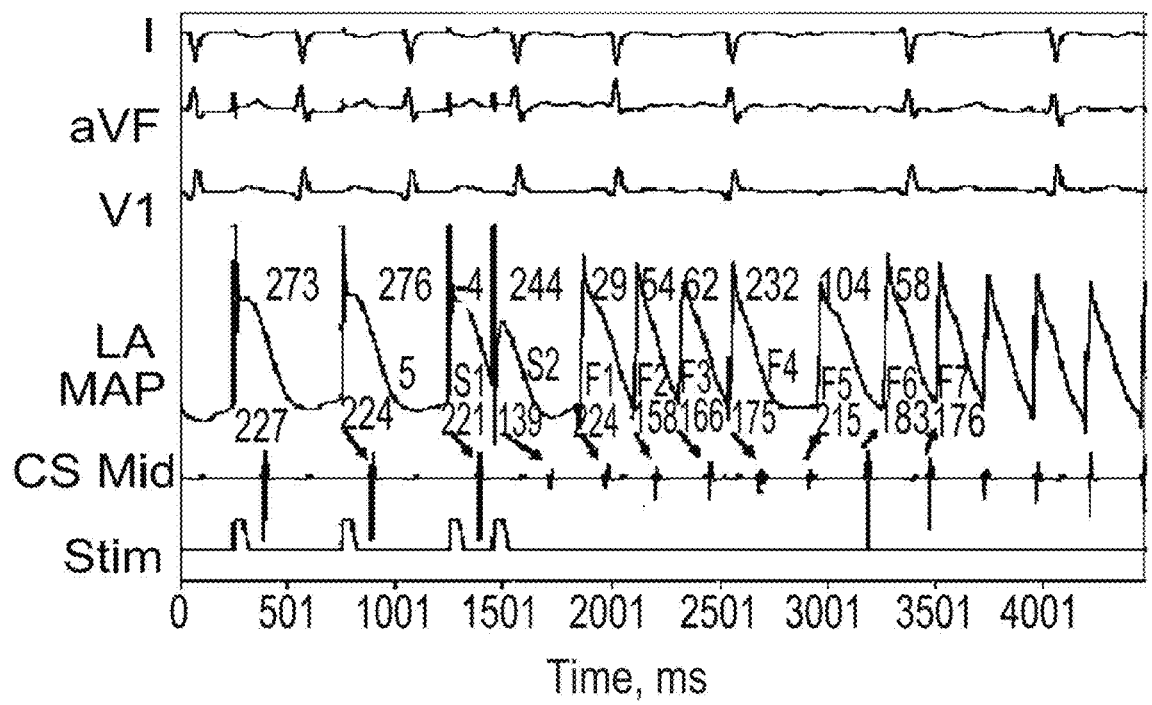
FIGS. 8A-8E illustrate that rate-response (restitution) of human monophasic action potential duration may differ when measured between paced rhythms and AF.
Figure 8B:
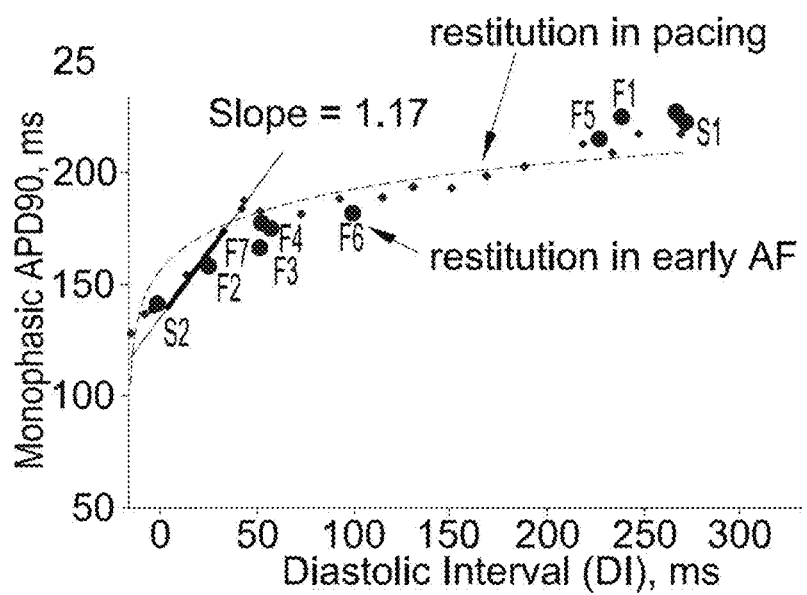
Figure 8C:
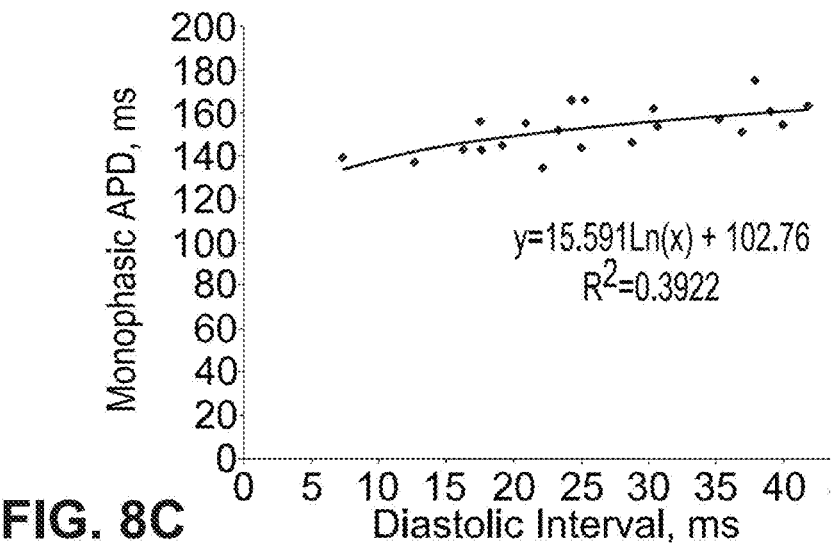
Figure 8D:
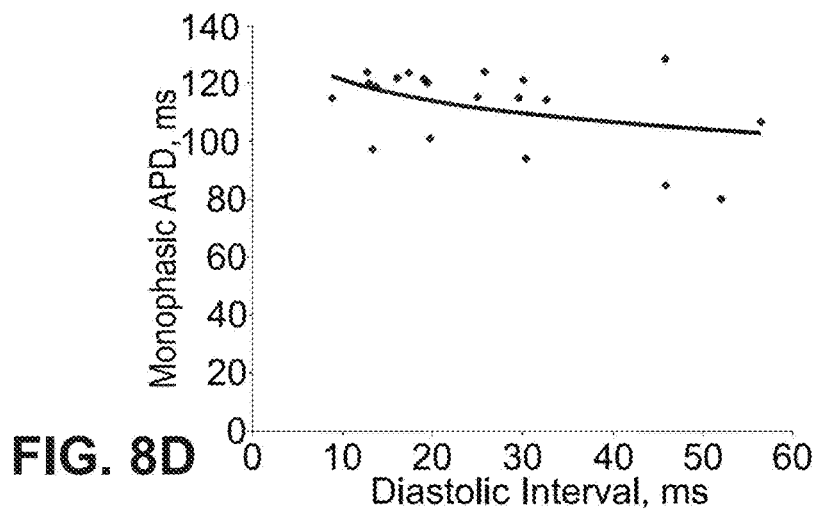
Figure 8E:
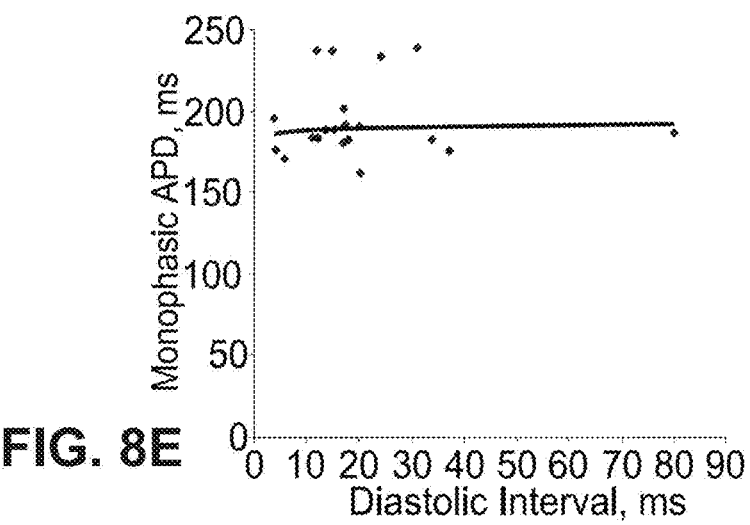

One approach embodied in the present invention is to create a 'hybrid' signal by inserting a physiological pattern at the time of each activation time onset (waveforms 660-670 in FIG. 7G). The physiological pattern may be obtained by averaging recorded signals over time (algebraically, from the median beat average or other method), averaging signals at neighboring locations (spatial averaging), from monophasic action potentials at various locations (waveforms 660-670), by filtering existing unipolar or bipolar signals in the frequency or time-frequency domain, or by using stored patterns from a database (FIG. 1, database 160). When stored signals are used, properties including duration of these physiological patterns may be adjusted for rate using rate-response (restitution) behavior. Stored signals may be obtained from this patient, another patient with similar characteristics or another stored relationship. These processes may be applied to individual activations, or to the entire signal.

This method results in a physiological representation of activity at each location over time that may otherwise be difficult to obtain in the beating heart of patients during minimally invasive procedures. It has applications outside of heart rhythm disorders. For instance, said physiological pattern may be a model of cellular ion function. This enables the function of these ion currents at each sensor to be modeled cells timed to each observed activation, for the study of dynamics of calcium fluxes, potassium currents or other processes within the beating heart of this patient. By way of a further example, this physiological pattern may be a model of a pharmacological ligand, allowing study on the behavior of the beating heart to specific pharmacologic agents. In the gastrointestinal tract, cellular hormone release models may be studied for each peristaltic 'beat'. In the brain, known kinetics of neurotransmitter or endorphin release for discrete brain waves (non-invasive, via the scalp electroencephalogram or invasive, as surgery) may help to understand and treat various conditions. Treatment of conditions of epilepsy, for example, using the present invention is one embodiment of the invention. This invention also includes a method for determining the effect of a pharmacological or bioeffective agent on the body by correlating the behavior of the beating heart or rhythm of another body part with the release, binding capacity or rate, or other action of the agent on the body.

An activation trail is then determined from sequences of activation in the physiological signal at multiple locations. The simplest form of this analysis is to order activation at each location sequentially in time. In other embodiments, analysis may identify and locate causes for a rhythm disorder using frequency domain methods, time-domain methods or spatial-phase methods. Frequency domain methods include the Hilbert transform or wavelet transform or phase delay methods. Spatial phase methods involve analyzing the spatial inter-relationships between sites showing activation at a certain location, in order to define the activation trail.

Pertaining to phase-space methods, a well-known technique assigns a phase $\phi$ to the signal at every electrode and at every time point. The phase at the exact location of the tip of the rotor is undefined and summing up the phase of neighboring electrodes results in a "phase jump" of $2\pi$. Thus, a rotor location corresponds to a phase singularity. Mathematically, these phase singularities can be found by evaluating a line integral over a closed curve as $\oint \vec{\nabla}\phi \cdot d\vec{l} = \pm 2\pi$ where the line integral is taken over a path l surrounding the phase singularity. Since the signal from the electrode is a single observable, the determination of the phase requires special attention. We will employ several different methods depending on the quality of the electrode signal.

The first phase-space method will be utilized if the signal from the electrodes is noisy and/or has a small amplitude. In this case, activation times for each electrode will be determined, followed by a novel analysis of wave front dynamics. As a first step, the spatial resolution of the probes and their activation times may be increased using a bi-linear interpolation scheme that interpolates activation using a fine regular grid created across the surface. In high quality physiological signals that contain activation, recovery and diastolic interval information, this results in a time trace V(t) for each point of the refined grid.

Figure 9A:
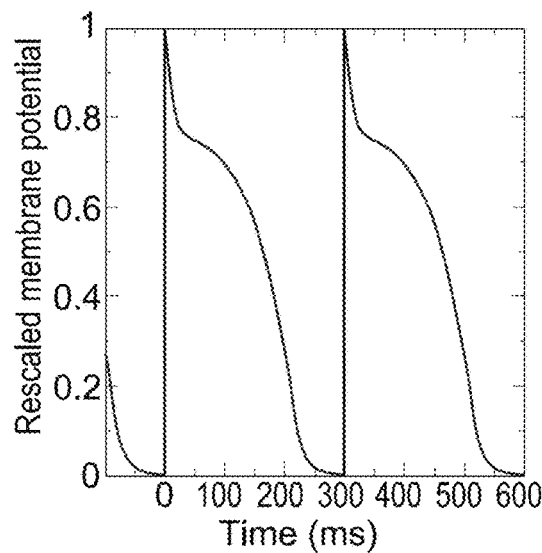
FIGS. 9A-9C show examples of direct assignment of phase.
Figure 9B:
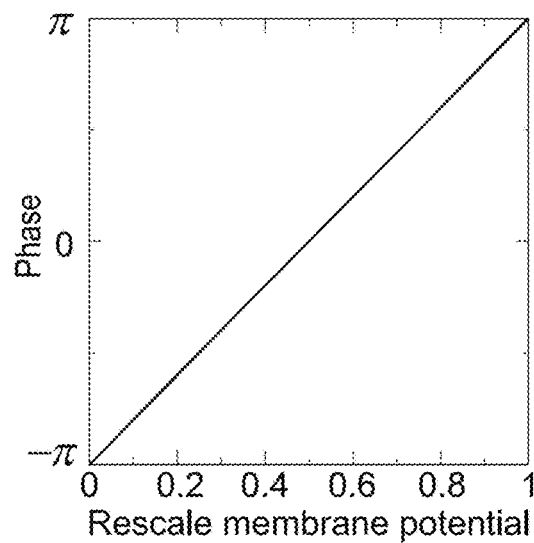
Figure 9C:
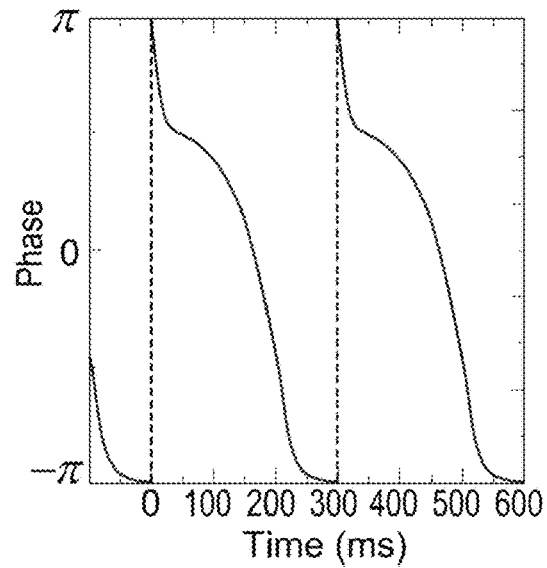

Since the shape of the action potential may be stable between beats, the method next defines a mapping from the membrane potential V to the phase $\phi$. This map assigns a unique value of $\phi$ to each value of V such that the maximum and minimum of the phase variable differs by $2\pi$. The detailed form of this map is arbitrary and the phase is computed using $\phi=2\pi(V-0.5)$. The corresponding time trace of the phase variable results in construction of the signal and its phase instantaneously as in FIGS. 9A-9C.

Once the phase map is constructed the method will calculate, for each time, the sum of the phase for all four points of the fine regular grid separated by a grid spacing that form a square (topological charge method). A result not equal to zero indicates the existence of a phase singularity and a rotor. The analysis will be further aided by the tracking of wave fronts. The location of these fronts will be computed using the regular fine grid by determining where and when V crosses a threshold value with a positive derivative dV/dt. Performing this calculation along the x and y direction of the fine regular grid and using linear interpolation between the grid points, will result in a set of points that lie on the wave front.

The wave front is then constructed by connecting these points. A similar analysis will be performed for phase, where isophase lines are tracked. A two-dimensional visual representation is then constructed that plots for each time point the value of the membrane potential using a grayscale or color scale, lines representing the wave fronts, lines representing similar phase (isophase lines), and symbols locating the phase singularities. This visual aid will greatly benefit the practitioner in interpreting the results of the inventive process and system. Note that the crossings of the lines representing the wave fronts and the isophase lines represent the phase singularity. Phase singularities indicate core regions, and thus can be used to localize the rotors.

The phase transform is able to demonstrate focal beats in AF—typically as centrifugal sources emanating from a localized area. A focal beat is characterized by a location that fulfills three criteria: 1) its activation time is earlier than at surrounding locations; 2) this region was previously inactive (in diastole) for a specified period of time; 3) the subsequent spread of activation emanates radially from the core region. Recognizing these 3 criteria, the invention finds these sources automatically. This algorithm will first determine locations that exhibit activation times ahead of their four nearest and four next-nearest neighbors and mark these as potential focal sources. Next, it determines the activation times at locations surrounding a potential focal source. If the activation times of these locations are earlier than their surrounding electrodes, the potential focal source is confirmed and is marked accordingly. These sites are plotted using our plotting technique as described above, greatly aiding the practitioner in localizing and interpreting these sources.

Alternatively, frequency domain methods may be used. On the physiological signal during the heart rhythm disorder, that may be the recorded signal or a signal derived after filtering, noise reduction and other strategies described above, one may employ several methods.

Figure 12A:
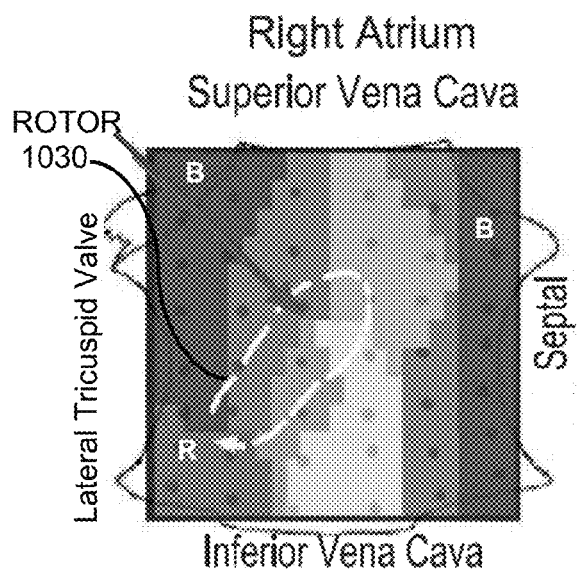
FIGS. 12A-12C show the results of using the method and system of the invention to identify an electrical rotor in the right atrium.
Figure 12B:
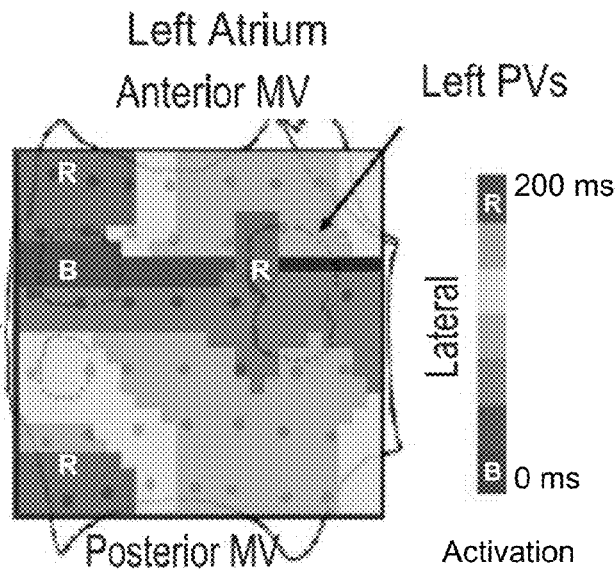
Figure 12C:
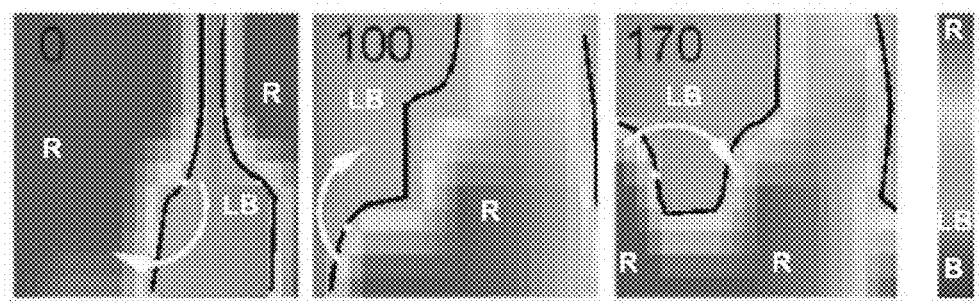

One such method is the Hilbert transform. The Hilbert transform shifts the phase of the negative frequencies of a signal by $\pi/2$ and the phase of the positive frequencies by $-\pi/2$. In this approach, determination of the phase $\phi$ of the signal is achieved by plotting voltage against the Hilbert transform of the voltage. The particularly useful embodiment applies a detrending algorithm to set the voltages at the activation times (maximum dV/dt) to zero. The Hilbert transform is used to construct the phase plane of detrended signals. The Hilbert transform at all locations is interpolated across the fine regular grid created across the biological surface. Phase is then calculated from the state-space plot of voltage versus its Hilbert transform. Again, the spatial distributions of phase will be analyzed with the topological charge technique described above to locate phase singularities associated with phase singularities (the ends of wavefronts) such as at the tip of a reentrant wave. Activation wavefronts are constructed using the same technique as described above while isolines of zero phase will also be tracked. An example of our methods in the human atria is shown in FIGS. 12A and 12C, which show rotors in the left atrium computed using frequency-domain methods.

Another useful method employs a time delay embedding technique to determine the phase of the signal. This technique consists of plotting V(t+τ)–V* vs. V(t)–V* for a fixed time delay τ and offset V*, resulting in a value of the phase φ for each time point and each location. In practice, the time delay and offset will be determined by the practitioner after examining these plots for several locations using different values for τ and V*. Optimal values lead to trajectories that do not cross (that would lead to a non-unique value for the phase) and that encircle the origin (ensuring that the minimum and maximum phase differs by 2π). Both the signal and the phase are interpolated across a fine regular grid created across the biological surface. The resulting phase map will then be examined for phase singularities and wave fronts will be tracked as described above.

Yet another useful method used to determine the phase of the signal is a wavelet transform. The exact form of this wavelet is variable, and an example includes the Haar wavelet. The wavelet transform will be computed for each location. The wavelet allows us to view the signal in multiple frequency resolutions. This will enable us to filter unwanted noise at specific frequencies (or frequency bands). In this approach, the phase transformation is achieved by plotting voltage against the phase shifted wavelet transform of the voltage. Once the phase φ has been calculated, we will precede as before, including refining the grid through bi-linear interpolation, finding phase singularity and tracking wave fronts.

Other information, such as locations within the organ of sites of rapid rate during the rhythm disorder, the presence of very regular sites surrounded by less regular sites, the presence of stable beat-to-beat configuration (shape) for successive signals as opposed to varying signal configurations, proximity to anatomic features known to be associated with particular rhythm disorders (such as pulmonary veins in AF, His-Purkinje system in VF), or a combination thereof may also assist in identifying and locating sources.

Several types of activation trails may result, producing corresponding discernible signature patterns for various types of causes for a rhythm disorder. An activation trail in which sequences of activation revolve around a central 'core' region is termed a rotor. An activation trail that emanates radially from a core region is termed a focal beat (or a site of repetitive focal activations or beats). Another activation trail type is a dispersed pattern, in which a localized source is not clearly identified. In particularly useful embodiment, in such cases, signal sensing is repeated at additional locations or for additional periods of time. Localization of a cause for a heart rhythm disorder is based on the location of the core region and additional activation from this region. Some embodiments identify the core region directly. For instance, the Hilbert Transform and direct phase assignment methods identify the core region as the site where real and imaginary parts of the analysis intersect. In contrast, the direct sequential ordering method of the present invention indicates a core region either visually or analytically.

Figure 10:
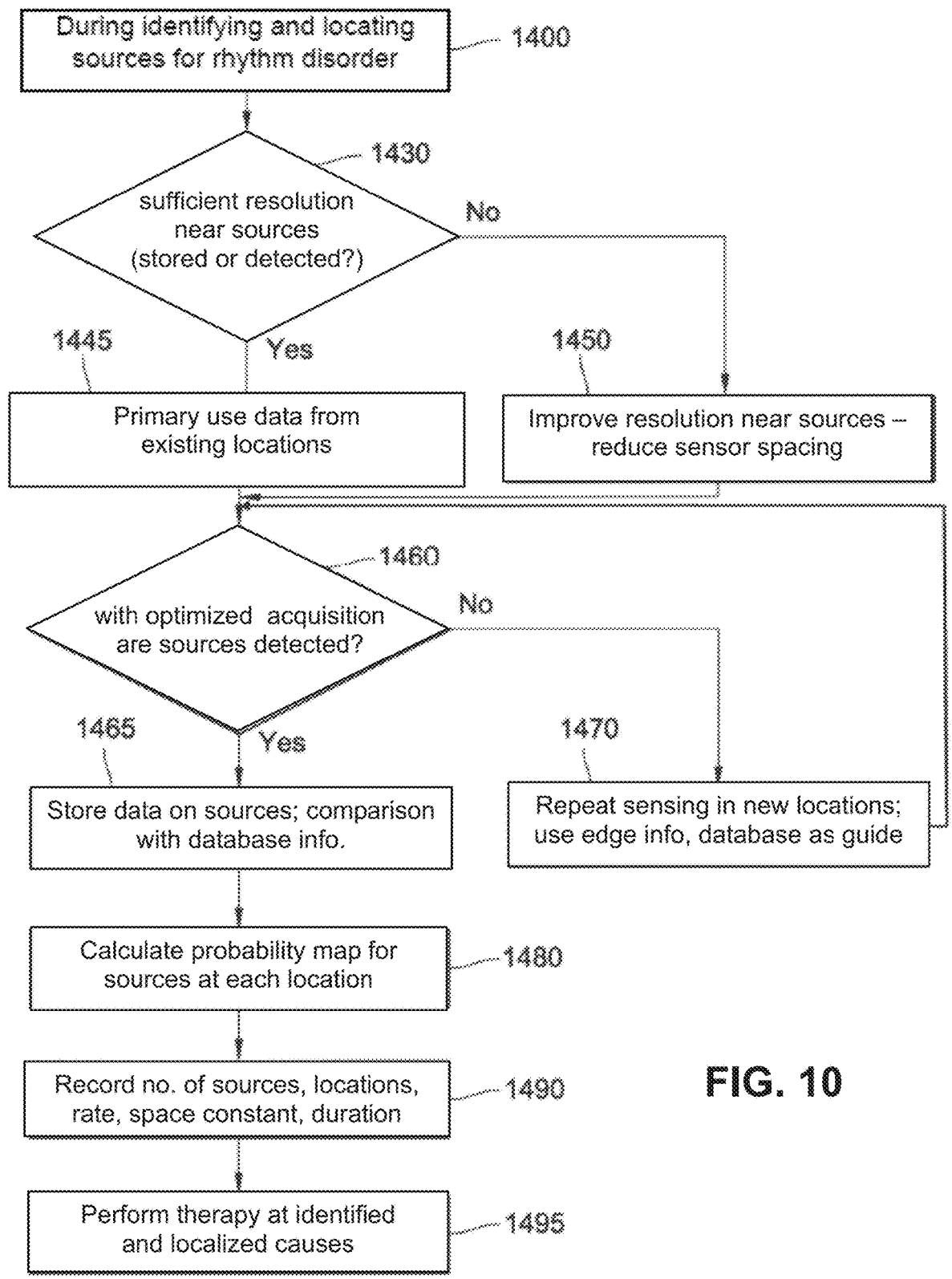
FIG. 10 is a flowchart of an embodiment, showing how sensed signals and stored data in a database can be used to create and use a probability map to improve clarity for identifying and localizing causes for a biological rhythm disorder.

FIG. 10, operations 1400-1495 describe the process of optimally identifying, locating and selecting cause(s) that are most likely to indicate primary causes of the rhythm disorder. In one particularly desirable embodiment, a probability map 1480 for sources of the disorder is constructed. This indicates a likelihood that each sensed location harbors a cause of the rhythm disorder, relative to other sensed locations. A higher relative likelihood is assigned for sites where core regions sustain for longer periods of time (or, for more rotations or beats), where the rate of activation is faster, where the rate of activation is more organized, that activate surrounding tissue in a 1:1 fashion (thus, there is electrogram linking) and activate larger regions of tissue in phase (and thus have a large space constant), when fewer concurrent sources are identified, for sources that lie near known regions of high likelihood for rhythm disorders such as the pulmonary veins in human AF, for sources with less migration over time, and for rotor versus focal beat types of source. In one particularly useful embodiment, probabilities are assigned after comparison with stored examples in a database; the comparison may take the form of a stepwise multivariate comparison. In the limited case of a spatially fixed source that is a solitary electrical rotor that directly activates the entire organ is by definition a primary cause of that heart rhythm disorder.

Surrogates for the activation trail also exist. These are data that approximate the identification and localization provided by the invention using data from fewer locations, less lengthy or detailed recordings, or using information from other resources such as the ECG rather than from within the heart. Thus, surrogates enable approximation of the activation trail using a reduced number of sensor locations compared to an analysis that directly measures the activation trail. These surrogates, used independently or in combinations, include sites of rapid rate during the rhythm disorder, the presence of very regular sites surrounded by less regular sites, the presence of stable beat-to-beat configuration (shape) for successive signals as opposed to varying signal configurations, signals where amplitude is particularly low, signals that are very prolonged for each activation is very prolonged, proximity to anatomic features known to be associated with particular rhythm disorders (such as pulmonary veins in AF, His-Purkinje system in VF), or a combination thereof may also assist in identifying and locating sources.

Surrogates may be detected from the ECG, and thus be used to plan a procedure or guide therapy in a patient. Vectorial analyses of the ECG for regions of regularity and high rate, particularly if surrounded by regions of lower regularity and rate, indicate locations within the heart where sources lie.

FIG. 10, operations 1400-1495 summarize the approach to identify and locate sources. Operations 1400-1450 determine if sufficient sensor resolution is present to identify a cause. Criteria for sufficiency include the absence of discontinuities in the wave front calculation, and absence of jumps in the location of core regions, and an absolute sensor spacing that should not exceed approximately 1 cm. This is based upon computations that the minimum circumference of a reentry wave is >2 cm in the human atrium and larger in the human ventricle. Operations 1460-1490 then use a combination of optimized sensed data and stored data to compute sources, which are then treated at operation 1495. The present invention includes the wide use of filtered or unfiltered clinical data, data from a database including this and other patients, or computational estimates to represent the signal to be analyzed as well as the results of analysis. In addition, the hybrid use of existing patient-acquired data, signal processing methods, numerical methods and stored signals from a database are major advantages of the inventive process and system, particularly because high-resolution physiological data from human atria or ventricles may be extremely difficult, if not impossible, to obtain at clinical electrophysiologic study without open heart surgery.

All of the above approaches may be applied to any complex rhythm, including VF. Of course, these approaches may also be applied to "simple rhythms" such as reentry around an anatomical obstacle or rotors anchored at scar tissue (such as atrial flutter).

These inventive processes may be implemented in software, operated very quickly and are suitable for real-time, as well as off-line analysis, using small scale components such as those found in implantable devices, portable ambulatory machines, wristwatch-sized devices, as well as larger scale computers found in electrophysiology laboratories.

Mode 3. Storing Data on Heart Rhythm Sources in Database

Data on sources for rhythm disorders desirably may be stored in a database 160. This may be useful to classify sources in different patients, to help identify sources in a single patient, or to determine if a patient has returned with the same or a different source. Data in the database will thus include the characteristics described above, including the number of concurrent sources, rate, variability in rate over time, duration, size of biological organ whose activation is directly caused by the source (the space constant), location, whether this location migrates over time, rate within multiple regions of the heart at the time that the source was detected (such as left and right atrial rate during AF), and the response of each source to ablation.

Additional information to be stored in the database include one or more clinical factors from a group comprising gender (male/female), age, weight, height, presence of diabetes mellitus, blood pressure, atrial size, ventricular size, regions of atrial or ventricular scar, the left ventricular ejection fraction.

In a particularly useful embodiment, the database of AF Sources 160 will be continuously updated, based upon new source localization from additional cases. This will be used to help source localization for practitioners studying new patients, by way of a software expert system that will match the new patient to already stored patterns.

Source data to be stored will be analyzed for consistency with existing data, matched by the above variables. Only raw data that meets rigorous standards for data integrity will be incorporated, others will be rejected. After ensuring data integrity, data will be added to the database to improve localization for future patients.

The invention and database interface may include an expert system that compares current data with stored data. Based on the closest match or matches, logic within the invention determines if additional heart rhythm sources or additional characteristic should be studied, and whether they may lie based on stored information. This uses a 'goodness of fit' against various stored parameters. This functionality is included because in practice, the number of sensed locations is limited by time constraints, in practice, many sensor locations may provide suboptimal data, thus limiting the actual sensed resolution, and because the inventor has observed that many patients show similar source locations and characteristics.

Database updates will be available to the practitioner regularly from a centrally located, secured database that contains the above information. No information on patient name, geographical location, study date or other items prohibited by the Health Information Portability Act (HIPAA) will be included. This database will be maintained at a remote location but available electronically by means including wired and wireless communication, electronic media such as CDs, DVDs, and solid state storage devices.

Mode 4. Display of Sources of Biological Rhythm Disorder

The invention includes methods and apparatus to communicate the identification, location and above characteristics of sources for biological rhythm disorders to the practitioner. This includes a visual display means, typically in the form of a graphical display on a computer monitor, or a printout showing the source in relation to cardiac anatomy, or a basic textual line summary of the location and/or sensor site where the source lies.

An auditory display may also be used, that vocalizes the identification, location and above characteristics of sources for biological rhythm disorders to the practitioner. In one embodiment, this would include the conclusions or a summary of analysis rather than the analysis results themselves.

Mode 5. Therapy at Causes of Biological Rhythm Disorder

In addition to the processes and systems of the invention used to detect and diagnose the cause of the rhythm disorder, the invention also includes devices and methods to treat the source for the biological rhythm disorder, in order to modify, ameliorate, or eliminate said rhythm disorder.

Treatment of the source may employ any useful technique, including ablation with radiofrequency, freezing energy, microwaves or other sources. Modification may also include cell therapy (such as with stem cells), gene therapy, pharmaceutical delivery, ionizing or non-ionizing radiation delivered by devices inside or outside the heart, or other interventions.

Treatment is delivered to modify the cause. In a simple heart rhythm disorder such as atrial tachycardia or atrial flutter, energy is applied directly to eliminate the cause. In a complex rhythm disorder, such as AF, energy can be applied to ablate (destroy) the source, to isolate the source by destroying tissue between the source and the remainder of the viable heart chamber, or to modulate the interaction between different sources. This latter form of treatment is very novel and has been shown in experiments by the inventor to be extremely effective. Modulation may be performed in a stochastic fashion.

In a particularly desirable embodiment, therapy is targeted at the core region of an identified or localized cause for the rhythm disorder, with the intention of eliminating this cause to treat the heart rhythm disorder. This may be applied sequentially to identify, locate and treat more than one cause for said disorder.

Alternatively, therapy may be targeted at locations neighboring the core region for a source, with the intention of disconnecting the source from surrounding tissue.

Alternatively, therapy may be targeted at locations neighboring the core region for a source, with the intention of causing the source to migrate towards tissue where definitive treatment is more easily accomplished. For instance, if the source lies at a location where ablation is difficult due to anatomy, tissue thickness or other factors, ablation on one side of the source may cause it to migrate towards a location that is easier to ablate due to thinner tissue or anatomic factors.

Alternatively, therapy may be targeted at locations neighboring the core region for a source, with the intention of preventing movement of the source and thus compartmentalizing it.

Alternatively, therapy may be targeted at locations neighboring the core region for a source, with the intention of reducing the mass of tissue available for the source to sustain and thus causing it to terminate.

Treatment may take the form of ablation, delivered via a catheter in the heart (element 25 in FIG. 1), on the epicardial surface, or an electrode present on one of the multi-electrode catheter designs included herein, for example, see FIGS. 2-4.

When a dispersed activation trail is observed, locations where sources may lie that are difficult to identify are targeted first. In patients with AF, such sites include the pulmonary veins and other thoracic veins, and the atrial appendages. Thus, pulmonary vein isolation is performed first, followed by therapy at additional sites if clinically suspected. Signal sensing is then repeated to identify and locate a cause.

In preferred particularly desirable embodiment, the multi sensor catheter (FIGS. 2-4) includes an assembly that can deliver therapy in the form of ablation. In this embodiment, sensors at locations where the source lies are activated to deliver ablation energy to modify or eliminate the source.

The system may deliver therapy in a spatial locus, as well as at fixed locations. In this system, the location of the source core region is analyzed constantly throughout therapy. Therapy, such as ablation energy, is directed at varying locations and potentially multiple locations to constrain movement of the source. An analogy is to construct a 'fence' of ablated tissue around a moving source in order to keep it in one location. This may require therapy delivery (such as ablation) at multiple sensors of said poles of said assembly concurrently. This process is continued until the rhythm terminates or a remote source becomes dominant.

This invention is well suited to target therapy performed surgically in the operating room with direct exposure of the heart. This may be via a minimally invasive approach or traditional open chest heart exposure. The choice of recording electrode, sock, plaque or other equipment is up to the discretion of the surgeon and does not alter the principles of therapy.

Alternatively, said modulation can be applied by stimulating (pacing) the tissue. For pacing, the process controller 70 conditions the pacing module 50, to stimulate the heart using electrodes in the heart 20-25, electrodes on the body surface 30, or electrodes elsewhere such as from the esophagus 150. The electrode controller 40 receives signals from the electrodes before, during and after pacing. Pacing is used to increase heart rate and introduce extra beats.

In alternative embodiment, the invention can ablate or stimulate cardiac nerves to modify or eliminate the source. Thus, if sources lie at locations of heart ganglionic plexuses, ablation or pacing of such locations can be used to modify the source.

If the abnormal rhythm terminates after modifying or eliminating sources, attempts can be made to restart the rhythm. In the case of heart rhythm disorders, this may include very rapid pacing, the administration of isoproterenol or other interventions. The entire application of this invention is then repeated.

In the event that the abnormal rhythm can no longer be initiated, the physician may exercise the discretion to modify additional regions that may be potential sources. This information may be available directly from stored data in the database, matching patients with a similar classification to the current patient.

Mode 6. Non-Real-Time Review Mode

In an important mode of operation, the invention can be used in a non-real time, offline analysis fashion. This review mode can be applied to data from this individual at another time, such as a prior electrophysiologic study, data from a different device (such as an implanted pacemaker or defibrillator) or even a prior failed ablation. This can be used to review results from a prior procedure, to review data from a patient prior to planning the application of this invention, or to assess if the same patient now presents with the same or a different source for their rhythm disorder.

Signals are first uploaded from stored electrograms in a database 160 to the processor controller 70. This database can be the master database that stores data on multiple patients, or a patient-specific database. Data storage and retrieval can be implemented for any signal type. Stored signals can be derived from another source, a catalogued source, or computed or virtual signals such as from Ensite 3000 or NavX by St Jude Medical, or Carto by Biosense-Webster. Signals may also be derived from a different individual, querying the database for a patient with similar demographics and heart rhythm disorder.

In a separate non-real-time mode, data obtained when the patient is not in the heart rhythm disorder can be used by the invention to identify and locate sources for a rhythm disorder. This may be useful, for example, if the heart rhythm disorder is not observed at the time of a procedure, and cannot be started using conventional methods. This mode uses biological properties of the chamber to predict locations where sources/causes may lie when in the heart rhythm disorder. Such locations include sites where the maximum slope of action potential duration restitution is >1, sites where beat-to-beat oscillations in the repolarization signal shape or duration are observed, or where conduction velocity restitution is broad to indicate slowed conduction at critical rates.

In the preferred embodiment, to measure restitution it is necessary to sense signals for a wide range of rates at each location, as indicated in FIG. 1 element 90. This may be achieved using pacing. In this case, the process controller (FIG. 1, element 70) conditions the Pacing module 50, to stimulate the heart using electrodes in the heart 20-25, on the body surface 30, in the esophagus 150 or elsewhere. The wider the range of rates, particularly fast rates, the more comprehensive the data range for that signal for analysis of restitution. When pacing is not an option, the invention will prompt the user to increase heart rate using other options or to use stored information from a database.

In this embodiment, the rate-response ("restitution") curve is created at each rate for each component of signals shown in FIG. 5. For example, this step may compute how monophasic action potential duration (time from phase 0 to phase 3) varies with rate (APD rate restitution). Examples of atrial APD restitution are shown in FIGS. 7A-7G and 8A-8E. Using pacing to increase the range of sampled heart rates provides a comprehensive assessment of rate response of each biosignal.

FIGS. 7A, 7C and 7E illustrate a useful embodiment, whereby human action potentials recorded in the left atrium 420 provide high quality information including depolarization (phase 0), repolarization (phases 1-3), phase 2 amplitude and action potential duration (time interval from phase 0 to phase 3). Phase 4 indicates the interval between one beat and the next. The invention may determine rate response (restitution) of multiple components, focusing on rate-response of AP duration (time from phase 0-3), and AP phase II amplitude.

Reference 400 (FIG. 5) is an ECG. This includes intra-atrial components (the P wave and PR interval), and ventricular components including depolarization (the QRS complex) and repolarization (the T wave). For atrium, the invention records how P-wave duration varies with rate, using analyses shown later in FIGS. 7A-7F. For the ventricle, the invention records how QT interval varies with rate as a measure of ventricular APD rate-behavior (restitution). Individual QRS complexes are aligned using one of several columnar techniques, including methods that align electrograms about the point of largest positive or negative slope, their peak values or minimize their mean square differences, or metrics based on derived signals. T-waves are identified and aligned similarly. Atrial activity is considered to lie in the intervening intervals.

If the signal is a unipolar electrogram, it is also analyzed in analogous fashion. Each is analyzed for waveform shape as well as duration. FIG. 5, Items 430-440 indicate unipolar electrograms from the human left atrium 430 and left ventricle 440 respectively, with depolarization and repolarization measured collectively as the activation-recovery interval, a surrogate for the monophasic action potential duration. The invention determines adjustment of various components for rate.

Signals can also be bipolar electrograms (items 450, 460), and the invention determines rate response of each component.

In an alternative embodiment, ECG and electrogram data are uploaded from a database 160 for analysis in an analogous fashion to the described real-time mode of operation. Data from the database can be from the same or different patients, recorded at any time and using any acquisition system.

In AF, MAP restitution may differ from MAP when not in AF. FIG. 8 element 700 shows the initiation of AF after pacing. Element 710 shows MAP restitution during pacing in black. Immediately after AF onset (red points), APDs track previously derived MAP restitution. However, this may not be true for longer-lasting AF. Elements 720, 730 and 740 show patients with long-lasting AF, in whom APD restitution differs from that obtained in pacing prior to AF.

Thus, it may be advantageous to use APD restitution obtained from the patient in AF, at this time or a previous time, or from stored APDs in this or other patients, or filtered or computed data, for signal processing and analysis.

Locations where sources may arise during a subsequent heart rhythm disorder may now be predicted from these analyses. For monophasic action potentials, site where the maximum slope of MAPD rate-behavior (restitution)>1 may be immediately adjacent to causes for VF or AF. Other indexes of high likelihood for the initiation of heart rhythm disorders include broad rate-response (restitution) of conduction, since such sites of dynamic conduction slowing may indicate sites where heart rhythm causes lie.

The energy generator 60 may be activated to apply destructive energy (either radiofrequency, cryoablation or microwave radiation) via the ablation electrode 25. This electrode can be moved within the heart manually by an operator, which is the traditional approach, or remotely using robotic or computer assisted guidance.

The implementation of the system described herein may be based largely upon digital signal processing techniques. However, it should be appreciated that a person of ordinary skill in this technology area can easily adapt the digital techniques for analog signal processing.

EXAMPLES

Identification and Localization of Source for AF in 47-Year-Old Man.

Figure 11:
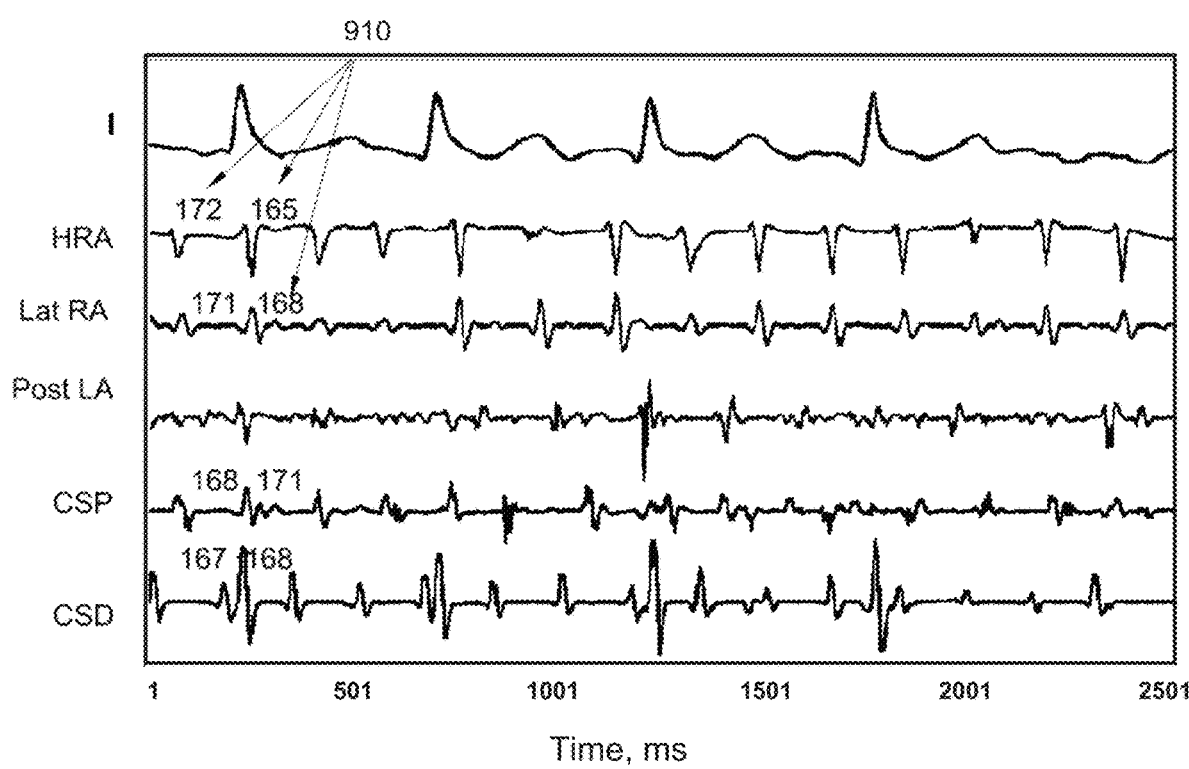
FIG. 11 is an example of use of the invention in a 47-year-old man. Shown is a selection of signals (electrograms) from within the left and right atria and coronary sinus of a patient with atrial fibrillation presenting for therapy.

FIG. 11 illustrates pre-ablation signals for a representative patient, a 47-year-old man with persistent atrial fibrillation (AF) for over five years. The patient continued to have symptomatic racing of the heart, which required him to visit hospital emergency rooms for treatment, despite various therapy with amiodarone and other appropriate therapy, and despite prior ablation procedures for AF. Given the severity of his symptoms, the patient therefore elected to return to the electrophysiology laboratory for further evaluation and ablation.

FIG. 11 shows signals from the right and left atria during AF at the commencement of electrophysiologic study. It can be seen that the AF cycle length (time between successive activation onset times) is quite short, shown as 172 ms and 165 ms for the first two cycles in the right atrium (arrows 910), and varies, as is typical for AF. Notably, signals were more fractionated and disorganized in shape in the left atrium ('post LA') and coronary sinus ('CSP' proximal coronary sinus; 'CSD' distal coronary sinus) than in the right atrium ('HRA' high right atrium; 'Lat RA' lateral right atrium; 'post RA' posterior right atrium), as is common.

These findings would normally guide ablation towards the left atrium. A typical procedure in this case would commence by ablating near the pulmonary veins and confirming isolation, followed by additional ablation selecting at sites including: (a) left atrial sites of fractionated electrograms, linear ablation at the roof, linear ablation at the mitral annulus, other linear ablation, then (b) right atrial ablation including sites of fractionation and the cavotricuspid isthmus. This proposed procedure would take approximately 2-3 hours with a <50% chance of terminating AF, meaning that electrical cardioversion would be required to restore normal rhythm at the conclusion of the procedure (Calkins, Brugada et al. 2007).

Rather than use this known approach, an embodiment of the method and treatment of the present invention was applied. A catheter assembly containing 64 sensors (electrodes) was inserted via the femoral veins into the right atrium, and across a trans-septal puncture into the left atrium of the patient. These were connected via wire cables to a recording system for collecting signals at each sensor during AF. These signals were converted to digital form, and input into a computer program. Activation onset times were recorded for 2 seconds of AF at each sensor. While two seconds was used with this patient, any greater or lesser periods of time may be useful. Desirably, one second or less may be used. In some embodiments, milliseconds may be used. Activation onset times at each sensor location were sequentially ordered in time. Stored action potential tracings were used to create an electrograph (voltage-time series), by inserting said tracings at the activation time onsets for each sensor. Finally, a direct phase assignment technique was used to identify a core region. An activation trail is directly indicated by the relationship of these activation sequences to a core region—if they revolve around a core, then an electrical rotor is detected and considered to be a cause, but if they emanate radially from a core region, then a focal beat is detected and considered a cause. Results were displayed as an animation on a computer monitor for physician review.

The activation trail 1030 in FIG. 12A revealed an electrical rotor as the cause for this man's AF. In FIG. 12A, activation onset times can be seen to revolve around a core region in the right atrium at times color-coded (and alphabetically coded) from 10 ms (blue ("B")) to 200 ms (red ("R")). No localized cause was found in the left atrium, shown in FIG. 12B. FIG. 12C displays this same rotor in a different form, as three snapshots in time of tissue that is depolarized (activated; red ("R")) and repolarized (not activated, light blue ("LB")). Viewed chronologically (0 ms, 100 ms and 170 ms, from left to right), these snapshots also trace activation sequences revolving around a core region (a rotor). This core region had a high likelihood of being a cause, since it was a solitary source that controlled electrical activation for almost all of the surrounding atrium (large space constant).

Clinically, it was surprising that this electrical rotor lay in the right atrium. The right atrial rotor site neither showed high spectral dominant frequency, nor low amplitude fractionated signals, and would not normally be identified or targeted for ablation.

Figure 12D:
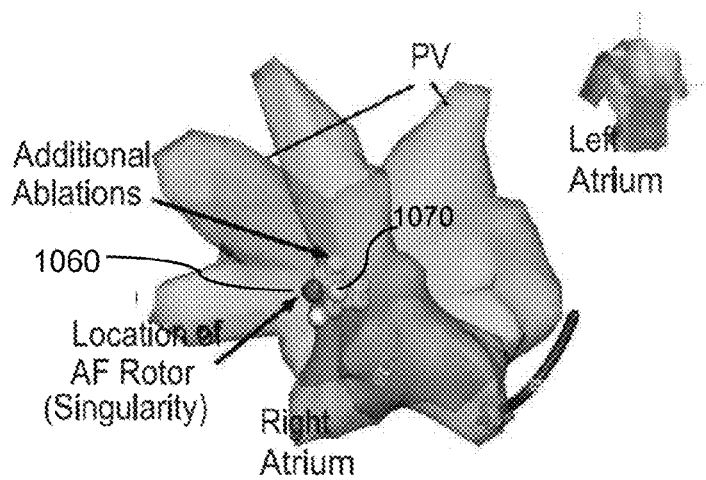
FIG. 12D shows the core region in the right atrium.
Figure 13:
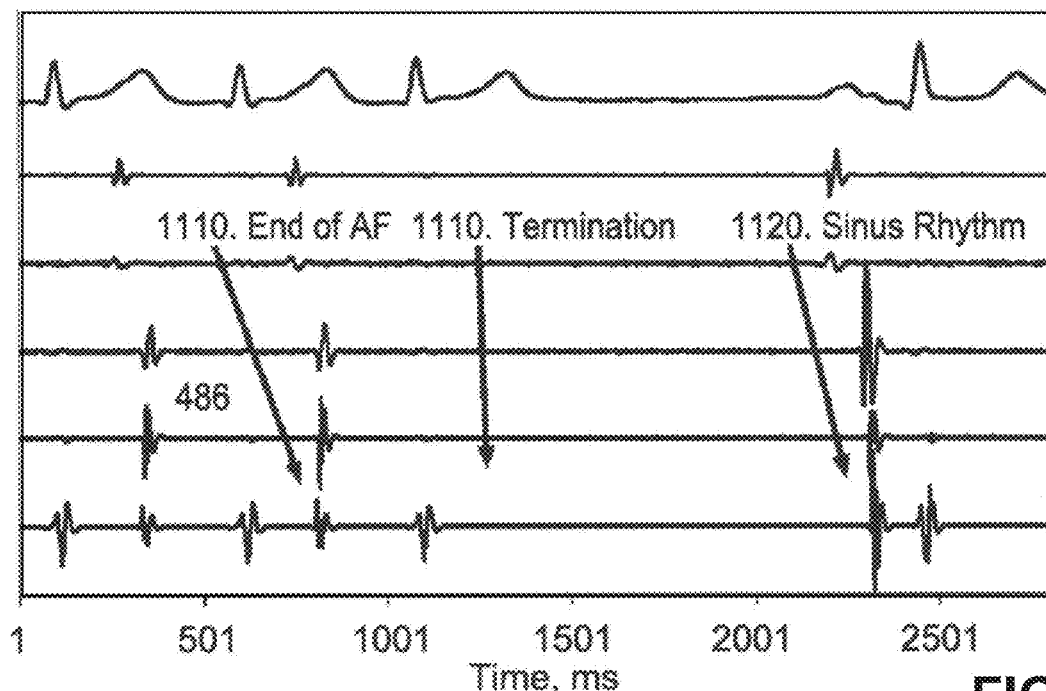
FIG. 13 shows that, during direct ablation at the core region identified in FIG. 12D for less than 6 minutes, the AF slowed and terminated to normal rhythm (sinus rhythm), thus demonstrating that the cause of the AF had in fact been located and successfully treated.
Figure 14:
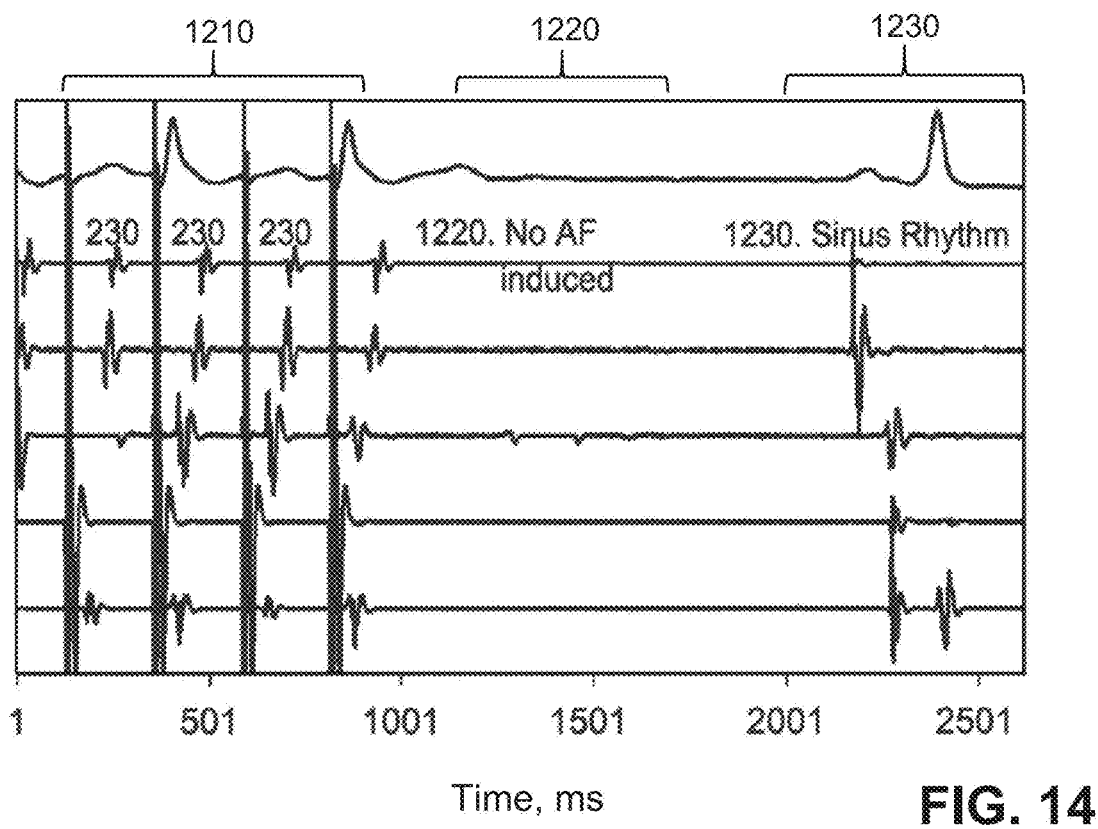
FIG. 14 shows that, after the AF had been terminated, it was not possible to re-start the AF even by pacing the atria very rapidly (cycle length 230 ms, equivalent to over 260 beats/min). Faster rate pacing was now blocked (did not stimulate the atrium).

Ablation commenced directly at the rotor core in the right atrium, at a site indicated by the red (dark) dot 1060 in FIG. 12D. Notably, AF slowed within 30 seconds of energy delivery to a cycle length of 227 ms. Subsequent ablation at immediately adjacent sites, indicated by white dots 1070 in FIG. 12D, further slowed AF until it terminated to sinus rhythm within 6 minutes after ablation, as shown in FIG. 13. In FIG. 13, panels 1100 to 1120, AF can be seen to stop (arrow 1110), followed by the restoration of normal sinus rhythm (arrow 1120). At this point, AF could not be restarted using the typical technique of rapid pacing as shown in FIG. 14, where segment 1210 shows rapid pacing with capture of the atrium, segment 1220 shows no induction of AF, and segment 1230 shows sinus rhythm after the end of pacing.

This result is paradigm-shifting compared to the current state-of-the-art, where slowing of AF typically occurs after lengthy ablation that is widely and empirically applied (to 30-40% of the atrium), yet termination of persistent AF is still uncommon. Conversely, we acutely slowed and acutely terminated AF with ablation of less than approximately 2-3% of the atrium. Ablating only at one site identified a priori in persistent AF, and seeing immediate slowing and termination of AF is not known to have been performed previously.

Other Examples of Identification and Localization of Sources for AF

A 77-year-old man presented for ablation of atrial fibrillation (AF). His history was notable for paroxysmal AF despite multiple antiarrhythmic medications, a slightly enlarged left atrium (diameter 45 mm) and normal left ventricular ejection fraction (58%). At invasive electrophysiology study, catheters were inserted into the atria as described. The invention was applied to multiple sensors. In FIG. 15A shows a localized source in the form of an electrical rotor near the left inferior pulmonary vein. Inspection of panels 901-904 from left to right (forwards in time) shows that the depolarized (activated) tissue in warmer colors (red ("R")) revolves clockwise around a core region on the medial lip of the left inferior pulmonary vein (see outline as black hourglass). Ablation at this site terminated AF acutely.

A 40-year-old patient with persistent AF presented for ablation. The AF was resistant to flecainide and other anti-arrhythmic medications, his left atrial diameter was 52 mm and left ventricular ejection fraction was 69%. At invasive electrophysiology study, catheters were inserted into the atria as described above. The invention was applied to multiple sensors. FIG. 15B, panels 911-914 show a localized source in the form of an electrical rotor in the posterior wall of the left atrium. Again, viewing panels 911-914 from left to right shows that activated (depolarized) tissue revolves counter-clockwise around a core region on the posterior wall of the left atrium between the pulmonary veins. After ablation at this site, the patient remains free of AF. To the best of the inventors' knowledge, these are the first actual demonstrations of the existence of electrical rotors in human AF.

Figure 16A:
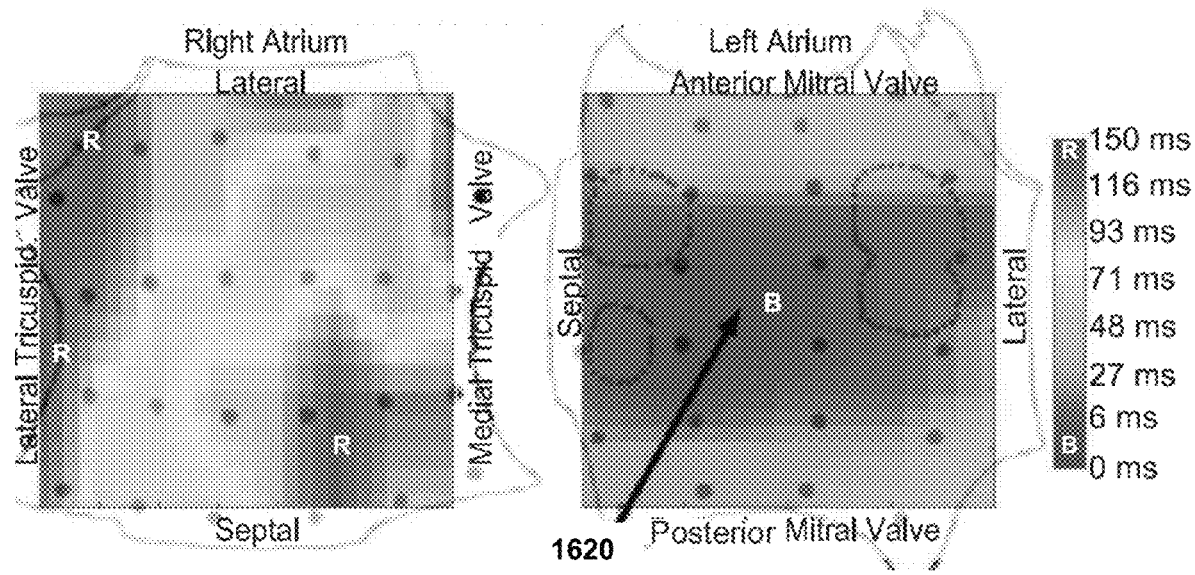
FIGS. 16A and 16B show an example of a localized focal beat cause of AF in a 56-year-old patient.
Figure 16B:
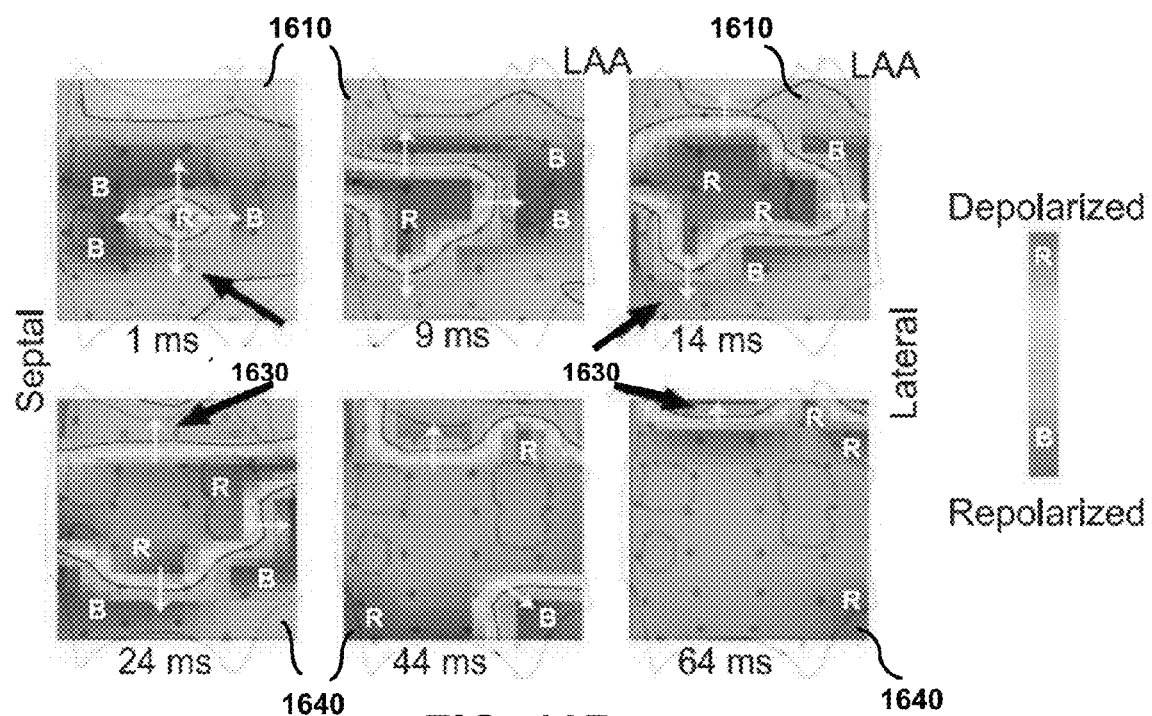

A 56-year-old patient with paroxysmal AF and significant symptoms presented for ablation. The AF continued despite several anti-arrhythmic medications. His left atrium was moderately enlarged. At invasive electrophysiology study, catheters were inserted into the atria as described above. The invention was applied to multiple sensors. Panels 1610 of FIG. 16B show the output of a localized source in the left atrium, between the pulmonary veins although not lying at these veins. The source was repetitive, as indicated by arrow 1620 in FIG. 16A. The activation trail (indicated by arrows 1630) shows activation emanating radially from this site. In panels 1640 of FIG. 16B, left atrial activation is seen to be fibrillatory (disorganized). Ablation was applied to this focal beat cause, and AF terminated acutely. At the time of filing, the patient has been completely free from AF for several months. This is a paradigm shifting because normal ablation lesions in this patient, that circle the pulmonary veins, would have missed this source. Thus, this patient would likely have been one who would have recurred after ablation, if the prior art known techniques of treating AF were used.

Figure 17A:
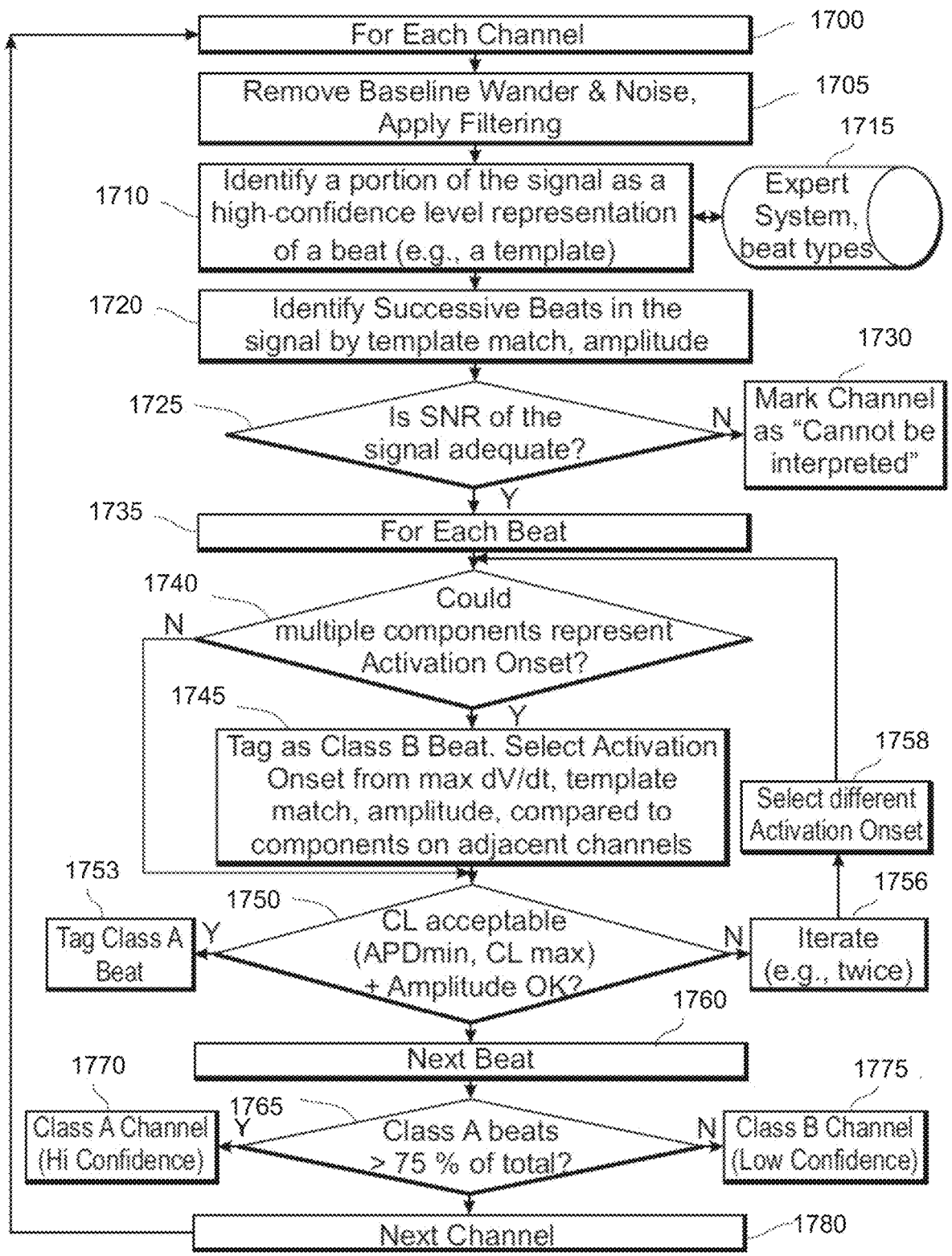
FIGS. 17A-17C show a method of reconstructing cardiac signals associated with a complex rhythm disorder received over a plurality of channels from a patient's heart.
Figure 17B:
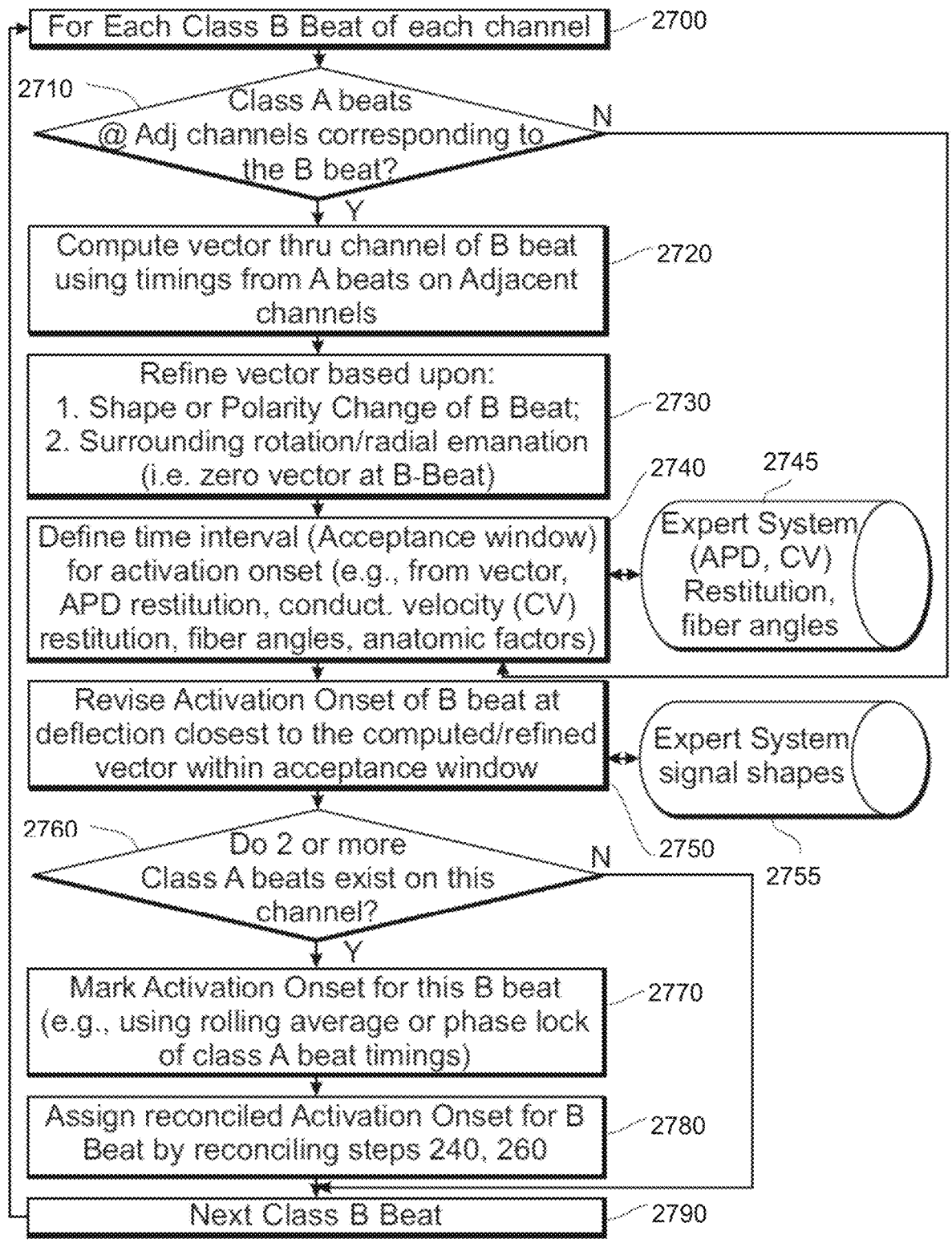
Figure 17C:
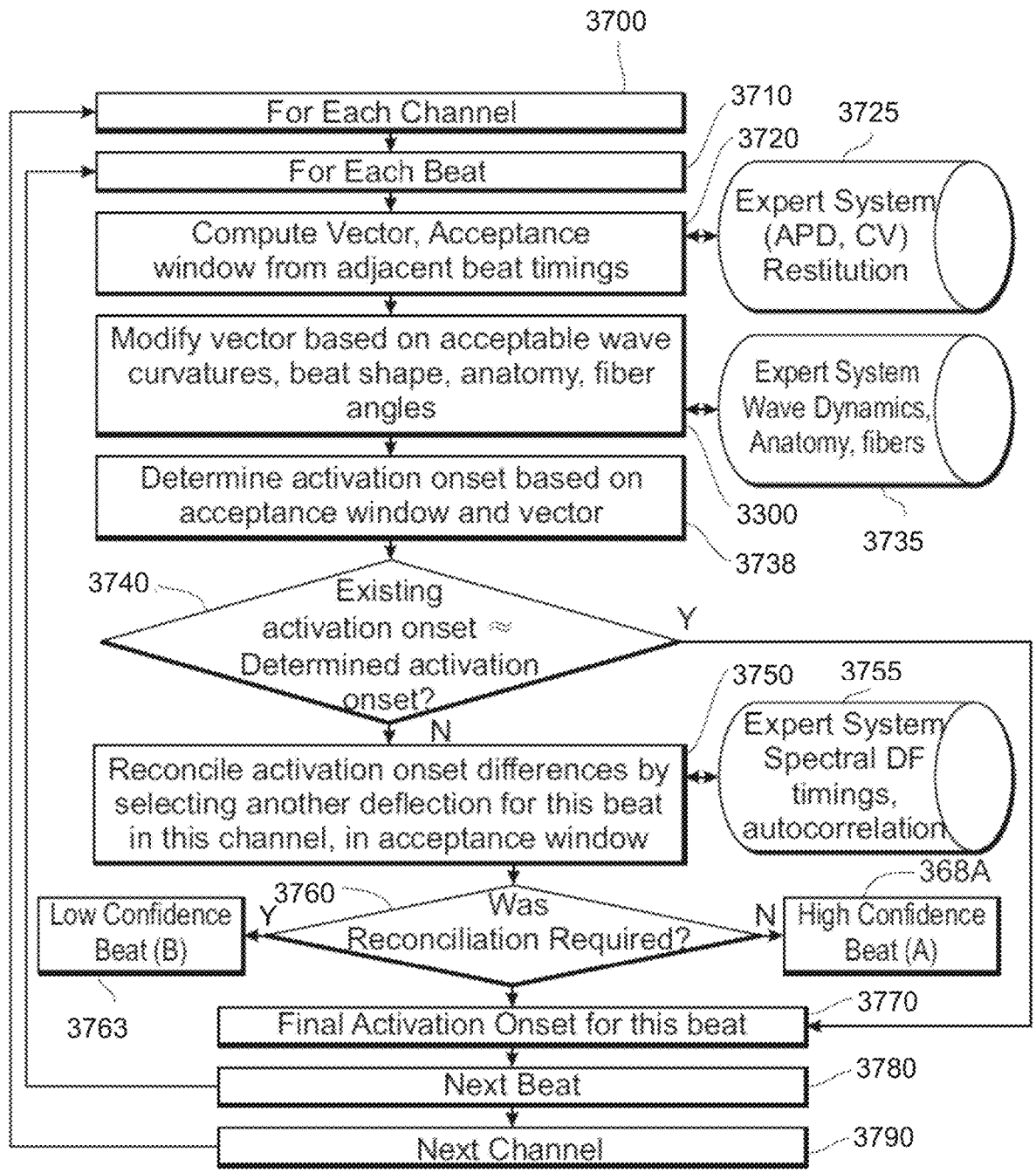

FIGS. 17A-17C illustrate a method of reconstructing cardiac signals associated with a complex rhythm disorder received over a plurality of channels from a patient's heart. The cardiac signals can be electrocardiogram (ECG) signals, signals from inside the heart (electrograms), representations of these signals, including magnetocardiogram signals or representations of mechanical activity (echo-cardiography, with or without Doppler), or generally any signals that represent the patient's biological rhythms. The cardiac signals can be received and recorded on a storage medium. The signals are captured by a plurality of sensors from the patient's heart and transmitted via the channels to at least one computing device. The at least one computing device is configured to reconstruct the cardiac signals in accordance with FIGS. 17A-17C. FIGS. 17A-17C also illustrate a constituent method of determining an activation time of a beat in the complex rhythm disorder. The at least one computing device is further configured to determine the activation time of the beat in accordance with FIGS. 17A-17C.

FIG. 17A illustrates a flowchart of an example method to classify the plurality of channels according to quality of beats in signals received over the channels. The method starts at operation 1700 in which a channel is selected from the plurality of the channels. A signal (or part thereof) received over the channel is retrieved. At operation 1705, one or more filters are applied to the remove baseline wander and noise from the signal. Additional filtering of the signal can be performed, such as, frequency domain filtering (e.g., bandpass, high-pass, low-pass, and/or other frequency domain filtering) and time-domain filtering (e.g., median-beat filtering, template-matching to produce correlation filtering, and/or other time-domain filtering). At operation 1710, a portion of the received signal is identified or selected as a high-confidence level representation of a beat (e.g., template beat). For example, the template beat can be selected (algorithmically, from a database, or via user interaction) with one or more attributes including but not limited to: an acceptable amplitude (signal to noise ratio >1), an acceptable cycle length (greater than the expected rate-related action potential duration), and absence of identifiable noise that may distort its signal shape. The selected template beat is used to identify other high-confidence beats in the signal. In one embodiment, the template beat can be selected using an expert system 1715 from a library of beat types according to one more criteria associated with the patient or the signal. These criteria include, but are not limited to age, gender, AF type (paroxysmal or persistent), length of AF history, AF cycle length, signal amplitude, recording location within the atria (e.g., left atrial, right atrial, coronary sinus), left ventricular ejection fraction.

At operation 1720, successive beats are identified in the signal, such as by performing template matching using the selected template beat. Alternate methods of identifying beats in the signal may also be used, including voltage above a threshold or maximum rate of change of voltage (first derivative, dV/dt) exceeding a threshold. At operation 1725, a determination is made as to whether the selected signal has an acceptable signal-to-noise ratio (SNR). The SNR is generally greater than one (1) (i.e., the signal is larger than the noise floor) but can vary depending upon sensor location and nature of the noise. For example, if the signal and noise are periodic but with different periods, then each may be separated by their different spectral characteristics. If it is determined at operation 1725 that the SNR of the signal is not acceptable, the channel is marked as a non-interpretable or non-usable channel at operation 1730. Alternatively, if it is determined at operation 1725 that the SNR of the signal is acceptable, the example method continues with operations 1735-1775 to classify the channel as a high-confidence channel or low-confidence channel according to the beats in the signal associated with this channel.

At operation 1735, an identified beat is selected from the plurality of identified beats in the signal of the selected channel. At operation 1740, a determination is made whether the selected beat includes multiple components that could represent an activation onset (e.g., deflections), one of which can be selected as the activation onset of the selected beat. If it is determined at operation 1740 that the selected beat has multiple components, then at operation 1745 the selected beat is tagged as a "Class-B" beat and an activation onset is selected in association with a component of the selected beat. A Class-B beat is one in which the activation onset cannot be determined with a high-degree of confidence, as opposed to a "Class-A" beat, which is typically monophasic (i.e., a non-complex beat in which the activation onset is not in question) in a setting of low noise and thus considered a beat having a high-degree of confidence.

Activation onset is selected based on at least one of the following: maximum dV/dt of the selected beat; template match of the beat to a template (selected automatically, or from a database based on patient type and location within the heart, or interactively by the user); amplitude of the selected beat; a comparison of the components in the selected beat to components of corresponding beats on adjacent channels; and/or another one or more selection criteria. Thereafter, the method continues at operation 1750 described hereinbelow. Alternatively, if it is determined at operation 1740 that the selected beat does not have multiple components that could represent activation onset (e.g., Class-A beat, as defined above (typically, a monophasic beat in an area of low noise), an activation onset is then selected and the method also continues at operation 1750 as described hereinbelow.

At operation 1750, a determination is made as to whether the cycle length of the selected beat based upon the selected activation onset is acceptable. An acceptable cycle length extending from the selected activation onset is defined as ranging from the minimum (rate-related action potential duration, APD) to the maximum (defined cycle length, CL). For example, in FIG. 19C, the deflections 608 are not acceptable since they fall within the minimum rate-related APD starting from that activation onset (depicted by 606). The maximum CL is a measurement of time from the selected activation onset to the next beat. From the observations of the inventor, the minimum rate-related APD can range from 90 to 400 ms. The maximum CL can also range from about 90 ms to 400 ms. If at operation 1750 it is determined that the cycle length is acceptable the selected beat is tagged as a "Class-A" beat at operation 1753.

However, if at operation 1750 the determined cycle length is not acceptable, then at operations 1756, 1758, the components (deflections) of the selected beat are iterated for a predetermined number of iterations (e.g., 2 iterations) until the cycle length extending from the activation onset of a selected component is determined to be acceptable at operation 1750. Beats that are considered to be "Class-A" (from operation 1740) are not typically modified, that is, their activation onset is not altered by these operations. Thereafter, at operation 1760 a next beat is selected from the selected signal and the operations 1735-1760 are repeated for the selected beat, until no beats remain on the selected signal (or for a predetermined number of examined beats).

At operation 1765, a determination is made as to whether "Class-A" beats make up a predetermined percentage of a total number of beats or number of beats examined in the signal of the selected channel. The predetermined percentage can be selected to be 75% of the total beats or examined beats. It is noted that other predetermined percentages can be used. If it is determined that there is a sufficient number of Class-A beats at operation 1765, then at operation 1770, the selected channel is classified as high-confidence channel. Alternatively, if it is determined that there is not a sufficient number of Class-A beats at operation 1765, then at operation 1775, the selected channel is classified as low-confidence channel. The method continues at operation 1780, where the next channel from the plurality of channels is selected and the operations 1700-1775 are repeated for this selected channel until the plurality of channels have been classified in accordance with the example method illustrated in FIG. 17A.

FIG. 17B illustrates a flowchart of an example method to revise or update selected activation onsets of certain quality beats in signals received over the channels. Specifically, the method of FIG. 17B iterates over Class-B beats of the plurality of channels to potentially revise or update selected activation onsets. Accordingly, the method starts at operation 2700 in which a channel is selected and a Class-B beat is selected in the selected channel. Once Class-B beats are processed on the selected channel, the next channel having class-B beats is selected until Class-B beats of the plurality of channels are processed (excluding channels marked as non-interpretable in operation 1730 of FIG. 17A).

At operations 2710, a determination is made as to whether there are Class-A beats that correspond to the selected Class-B beat (e.g., are within a predetermined time of the Class-B beat) in channels that are adjacent to the selected channel. If at operation 2710 it is determined that there are corresponding Class-A beats in the signals of adjacent channels, the method continues with operations 2720-2740. Alternatively, if at operation 2710 it is determined that there is no corresponding Class-A beat in the signals of adjacent channels, the method continues at operation 2750, as described below.

At operation 2720, a vector is computed using activation onsets of the corresponding (nearby) Class-A beats to guide selection of activation onset at the selected Class-B beat. At operation 2730, the computed vector is refined based on at least one property. The computed vector is defined by channel locations surrounding the channel of interest. As shown in FIG. 19B, activation onsets are defined for the beat under consideration in each of these channels. These activation onsets are used to define a set of plausible vectors as shown in FIG. 19D (knowing the spatial location of each channel). The vector based upon these surrounding channel locations will allow the best activation onset time to be determined for the channel of interest for that beat (e.g., FIGS. 19D, 21A, 22A-22C). The vector can also be refined based on the shape or polarity change of the selected beat, or whether activation from this site is rotational (i.e., a rotor) or radial (i.e., a focal beat) which both give zero vectors at the selected Class-B beat), and/or one or more other properties. Clearly, this vector may vary from beat-to-beat (cycle-to-cycle).

At operation 2740, a time interval (i.e., acceptance window) is defined for the selected Class-B beat. The time interval indicates the earliest permissible onset of the selected Class-B beat (relative to a prior beat) and the latest permissible onset the selected Class-B beat (based upon at least one property). The properties considered or used include the vector, APD restitution, conduction velocity (CV) restitution, diastolic interval (DI), fiber angles, one or more anatomical factors, as well as one or more additional properties. Specifically, the inventor has recorded conduction velocity measurements at various atrial regions at various rates in different patient types; these conduction velocity dynamics can be used to determine if a proposed signal deflection occurs too early or too late to be conducted along the computed vector. Similarly, the inventor has recorded measurements of action potential duration rate-dynamics, based upon fiber angle orientations at multiple atrial locations, as well as anatomic factors (such as the known propensity for regions such as the crista terminalis to show conduction block).

In one embodiment, the properties can be provided via an expert system 2745 from a library of properties according to one more criteria associated with the patient (e.g., whether the patient has advanced age or a very large atrium, both of which predict slower conduction) or the signal (e.g., if the signals are relatively simple or more complex). Parameters that are considered in the expert system 2745 include age, gender, whether AF is paroxysmal or persistent, blood pressure, atrial volume, left ventricular ejection fraction, presence of diabetes mellitus, and one or more other criteria. The use of DI to define an acceptance window is described in greater detail hereinbelow.

At operation 2750, the previously selected activation onset of the selected Class-B beat is revised or updated by comparison against activation onsets of selected components (deflections) of the signal of the Class-B beat that are within the acceptance window. In one embodiment, a component that is closest to the computed vector through the selected Class-B beat can be selected. In another embodiment, an expert system 2755, which stores a library of signal shapes according to one more criteria associated with the patient or the signal, can be used to select a component of the selected Class-B beat within the acceptance window. For example, age, gender and one or more other criteria can be used to classify the signal shapes in the expert system 2755. Thus, the acceptance window can be defined per beat, based on rate, location, patient demographics and/or one or more other factors.

At operation 2760, a determination is made as to whether at least two Class-A beats exist on the selected channel. If it is determined at operation 2760 that at least two Class-A beats exist on the selected channel, then the method continues at operation 2770 to determine a cycle length time interval between the Class-A beats (e.g., by subtracting the activation onset time of the Class-A beats). The determined time interval is successively advanced along the signal of the selected channel to determine whether a deflection of the signal lies at or close to this time interval within the acceptance window. In one embodiment, the time interval can be averaged (or median used) based on successive Class-A beats, if available in the signal of the selected channel. However, if it is determined at operation 2760 that no Class-A beat exists on the selected channel, then the method continues at operation 2790.

At operation 2780, the revised or updated activation onset of the selected Class-B beat is reconciled with the second activation onset of the determined time interval and assigned a reconciled activation onset. In one embodiment, a deflection (within the acceptance window) that is closest to the average of these onsets can be selected as the reconciled activation onset. Other embodiments can use the deflection closest to one of these activation times (weighted in order of importance), or other outputs from operations 1745, 2750 or 2770.

At operation 2790, a next Class-B beat is selected from the signal of the selected channel and the method iterates through operations 2700-2790 for the next Class-B beat. Once Class-B beats are processed on the selected channel, the next channel having class-B beats is selected until Class-B beats of the plurality of channels are processed in accordance with FIG. 17B, excluding non-interpretable channels marked in FIG. 17A.

FIG. 17C illustrates a flowchart of an example method to select final activation onsets of all beats in signals received over the plurality of channels. Specifically, the method of FIG. 17C iterates over Class-A and Class-B beats over the plurality of channels (high-confidence and low-confidence channels, excluding non-interpretable channels marked of FIG. 17A) to finalize activation onsets associated with the beats. Accordingly, the method starts at operation 3700 in which a channel is selected. At operation 3710, a beat is selected in the selected channel.

At operation 3720, a vector is computed through the selected beat and an acceptance window is defined for the selected beat, as described in operations 2720 and 2740 of FIG. 17B, respectively. The operations of FIG. 17C differ from the previous operations in that vectors can now be computed from Class-A beats and Class-B beats (as revised in FIG. 17B). The purpose of is to ensure that activation onsets are consistent between all Class-A beats and Class-B beats. Final adjustment of activation onsets can be made to minimize inconsistencies that now arise. In one embodiment, an expert system 3725 can be used to provide one or more properties to define the acceptance window, such as APD and CV restitution, DI, and/or other properties. At operation 3730, the computed vector is refined based on at least one property. For example, the computed vector can be refined based on wavefront curvature when mapped onto the atrium, beat signal shape, known anatomic factors such as conduction block at the *crista* terminalis, presumed fiber angles and/or one or more other properties. In one embodiment, these factors are quantified and coded in an expert system 3735, based upon patient age, gender, whether AF is paroxysmal or persistent, blood pressure, atrial volume, left ventricular ejection fraction, presence of diabetes mellitus, and one or more other criteria. At operation 3738, activation onset is determined for the selected beat within the acceptance window where the vector crosses the selected beat.

At operation 3740 a determination is made as to whether the previous activation onset of the selected beat (from FIG. 17B) is approximately equivalent (e.g., within a predetermined threshold) to the currently determined activation onset of the selected beat. If it is determined at operation 3740 that the previous activation onset of the selected beat is approximately equivalent, then the method continues at operation 3770 below. Alternatively, if it is determined at operation 3740 that the previous activation onset of the selected beat is not approximately equivalent, the method continues at operation 3750.

At operation 3750, the previous activation onset is reconciled with the current activation onset to obtain a reconciled activation onset. In one embodiment, a deflection (within the acceptance window) that is closest to the average of these activation onsets can be selected as the reconciled activation onset. An expert system 3755 can be used to provide cycle length estimates, which can be used to estimate the position of each activation onset following a specific beat, with the assumption in this case that signals demonstrate regularity at this channel. At operation 3760, a determination is made as to whether reconciliation of activation onsets was required. If at operation 3760 the reconciliation was required, then at operation 3763, the tagging of the selected beat is updated to a Class-B beat. However, if at operation 3760 the reconciliation was not required, then at operation 3768, the tagging of the selected beat is updated to a Class-A beat.

After operations 3763 and 3768, the method continues at operation 3770 in which the reconciled activation onset, determined activation onset (from operation 3738), or existing activation onset (from operation 2780 or as described with reference to operations 1740 and 1753 for class A beats) is selected as the final activation onset for the selected beat. At operation 3780, a next beat is selected on the selected channel and operations 3720-3770 are iterated for the selected beat until all beats are processed on the selected channel. Once all beats are processed on the selected channel, a next channel is selected at operation 3790 and operations 3710-3780 are iterated for the selected channel until all channels are processed in accordance with FIG. 17C, excluding non-interpretable channels marked in FIG. 17A.

The diastolic interval (DI) and action potential duration (APD) relationship can be used to identify activation onsets in a beat of a signal. In complex rhythm disorders (e.g., cardiac fibrillation), when a signal quality is insufficient to accurately determine an activation onset of a Class-B beat in a signal received over a channel, activation onset of a Class-A beat in the signal can be used along with the APD dependence on a previous DI to estimate an acceptance window for the Class-B beat. More specifically, an APD can be defined for each activation cycle based on a previous DI to reconstruct an action potential (AP) trace from the signal.

Figure 18:
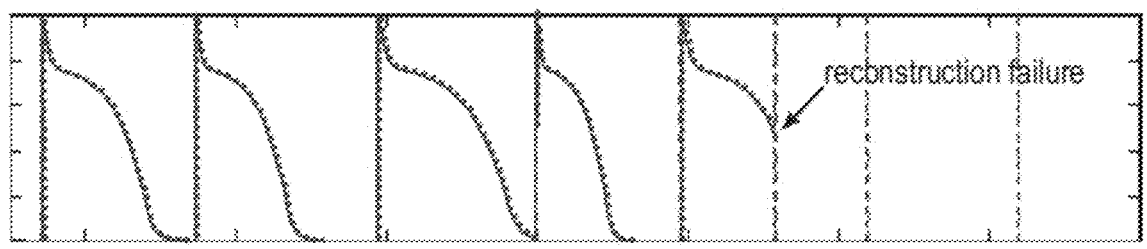
FIG. 18 shows a series of reconstructed action potentials and a failure of the reconstructed action potentials to conform to a detected activation onset.

An AP reconstruction attempt is deemed to have failed when any defined APD is less than a predefined minimum (e.g., 90 ms) or exceeds the available cycle length (CL) within which the APD must fit. The AP trace shown in FIG. 18 illustrates such a failure.

For example, considering the dashed lines to be selected activation onsets and the curved vertical lines to be an APDs in the AP reconstruction, the fifth APD has not fallen to an acceptable level for reactivation before the next activation onset is reached. This is deemed a reconstruction failure and implies that the APD-DI relationship used, paired with the initial DI used to calculate the first APD (DI seed) is not valid for representing the real APDs. It could be that the APD-DI relationship was incorrect, the DI seed was incorrect, or both.

If the relationship between DIs and the following APDs is known, then a patient-specific restitution curve can be used to check a series of selected activation onsets without performing a number of calculations through a range of values for the constants in the DI-APD relationship. In accordance with patient specific restitution curve, a series of activation onsets is considered incorrect if there are no DI seeds that result in a correctly reconstructed AP trace. When reconstructing the AP trace, if a disproportionately high number of reconstruction attempts (for each DI seed) fails for any low confidence activation onset (after the first four activation onsets), that activation onset is deemed incorrect and should be re-evaluated.

A linear or logarithmic function (algorithm) can be used to relate DI and APD. For example, the linear function can be APD=C1*DI+C2. The logarithmic function can be APD=$C_1$*ln(DI)+$C_2$. If the constants in the relation between DI and APD are unknown, the linear function APD=C1*DI+C2 can be assumed. AP reconstructions can be performed for plausible DI seeds and for plausible constants C1 and C2. The total number of AP reconstruction failures can be tracked for each activation onset that is marked. A largest number of failures in AP reconstruction are expected to occur in the first few activation onsets, as the incorrect DI seeds and constants will usually fail to fit the sequence within the first few activation onsets. If a disproportionately large number of failures occur later in the AP reconstruction, then the activation onset is considered "implausible" and marked for review and/or further analysis.

If an assumption is made that the relation between DI an APD is invariant for all locations in the heart, then the accuracy of the calculation can be improved by excluding constants C1 and C2 that lead to failed trace reconstructions in signals that have high confidence activation onsets. In this way, the foregoing algorithm will exclude all mathematical DI-APD relationships that are not likely to apply to the specific patient being analyzed.

Figure 19A:
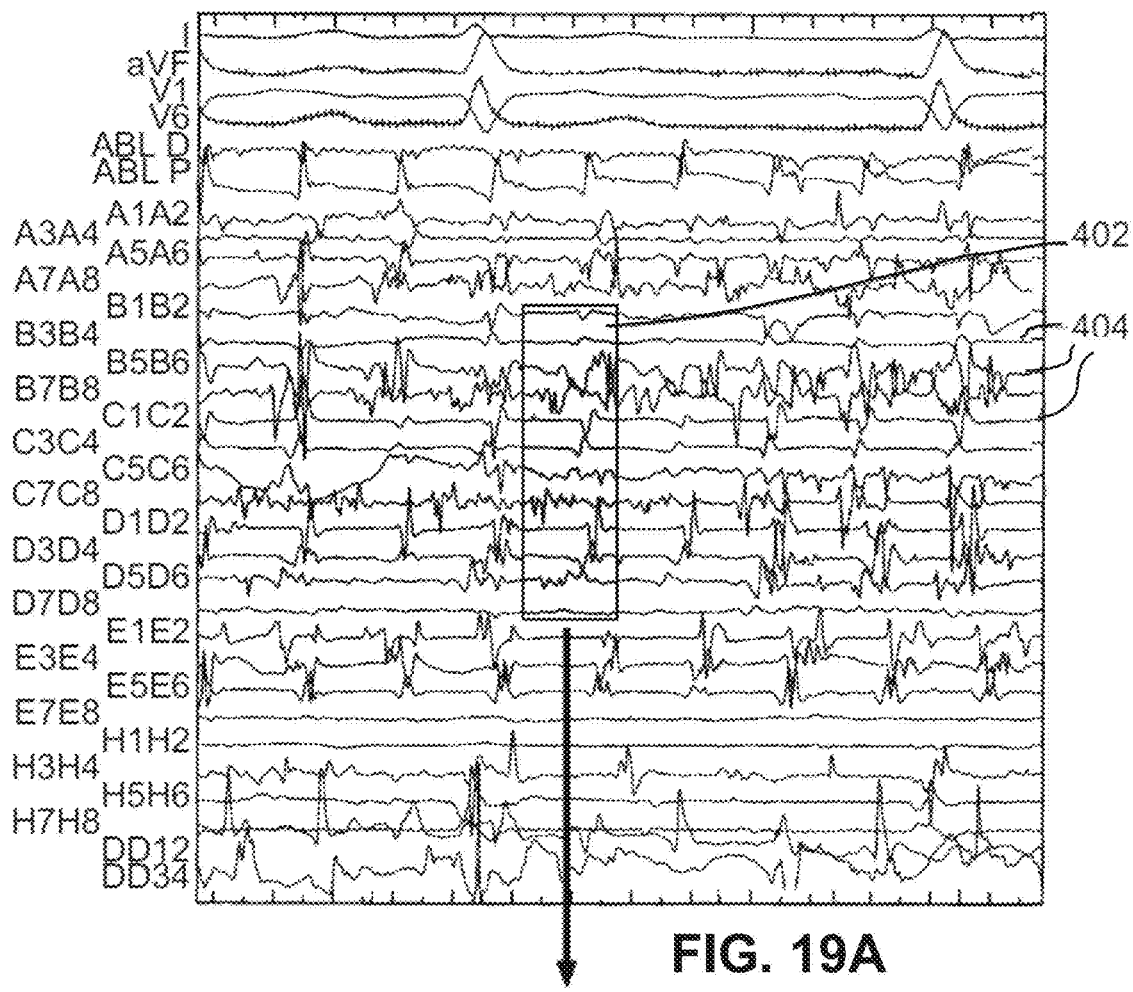
FIG. 19A shows a plurality of time-varying signals obtained from sensors receiving cardiac (electrical) activity from a patient's heart during a complex rhythm disorder (atrial fibrillation). The multiple deflections present in many signals, and the varying signal characteristics even at the same sensor location are noted, and make determination of each signal onset challenging.
Figures 19B, 19C, 19D:
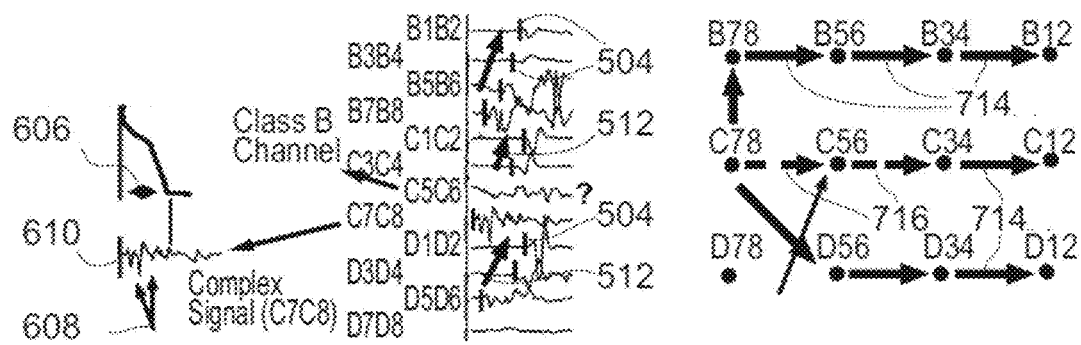
FIG. 19B shows just that portion of electrical activity within a window shown in FIG. 19A.
FIG. 19C shows an expanded view of a signal, for which a signal detection is excluded because it falls within the rate-adjusted activation potential duration (APD) and thus is taken as an artifact.
FIG. 19D is a two-dimensional representation of cardiac sensor positions or electrodes, which provides a grid on the patient's atrium.

FIG. 19A shows a plurality of time-varying signals 404 obtained from sensors receiving cardiac (electrical) activity from a patient's heart during a complex rhythm disorder. The sensors can be included in a cardiac catheter that is introduced inside the patient or the sensors can be disposed outside the patient. Each of the signals is represented by a signal identifier, such as "A1A2", "B3B4", and "B5B6". An example snapshot or window 402 represents example activity on each of twelve (12) of the cardiac signals 404 within a specified time period (e.g., 2 ms). The cardiac signals 402 represent electrical cardiac activity, during a complex rhythm disorder such as atrial fibrillation (AF), of various locations in the atrium, at which a corresponding sensor is located. It is to be noted that the detection of the "earliest" activation onset is impossible through mere visual inspection of the cardiac signals 404 shown in FIG. 19A, as there is no discernible quiescent period in the cardiac signals 404 to enable detection of the earliest activation onset from the signals 404.

FIG. 19B shows just that portion of electrical activity within the window 402 shown in FIG. 19A. The vertical lines 504 represent activation onsets for each of the time-varying cardiac signals. As can readily be seen from the cardiac signals shown in FIG. 19B, the activation onsets 504 for at least the signals identified by C5C6, C7C8, and D7D8 are not well-defined. Arrows 512 define a vector that connects corresponding points in adjacent time-varying cardiac signals. As can be seen there is no discernible earliest activation onset in the signals shown in FIG. 19B. In other words, it is not possible to simply trace activation back to the earliest channel (that, in this example, is channel C7C8). This is because multiple co-existing waves may exist in AF (unlike rhythms such as supraventricular tachycardia). FIG.

19D shows some of these potential wave directions, indicating multiple potential wavepaths. Considerations of maximum and minimum potential conduction velocity, and other physiological properties above, will determine the wave paths that are more or less likely to explain the observed continuous, varying, and complex signals at each electrode.

FIG. 19C shows an expanded view of the signal identified by C7C8 for which an activation onset cannot be determined due to multiple deflections, and an indication of the corresponding rate-adjusted activation potential duration (APD) item 606. The rate-adjusted APD 606 indicates that signals at this particular channel C7C8 cannot occur until near the end of the rate-adjusted APD 606. This fact is used to eliminate deflections of signal C7C8 that occur within the APD 606, as shown by arrows 608, and avoid counting the defections as activation onsets. This is because the cardiac tissue is unable to physically reactivate for the duration of the APD ("repolarization") 606. Naturally, the actual position of the APD 606 depends on the timing of the prior activation onset time 610.

FIG. 19D is a two-dimensional representation of the positions of the cardiac sensors or electrodes, which provides a grid on the patient's atrium. The representation of points on the grid, such as "B78", "C56", and "D12", correspond to the electrodes or sensors that are used to provide the corresponding time-varying cardiac signals, such as "B7B8", "C5C6", and "D1D2", respectively, as shown in FIGS. 19A and 19B. Thus, sensor "B78" corresponds to time-varying cardiac signal "B7B8", and sensor "C56" corresponds to cardiac signal "C5C6". Arrows 714 connecting specified sensors in FIG. 19D represent the vector directed between the corresponding locations of the patient's atrium. Thus, using only information in the cardiac signal C5C6, the activation onset associated with signal C5C6 can be determined using non-linear interpolation of the vector from sensors C78 to C34, the activations for which are both known. Alternative vectors, such as that from sensors B34 to C34 are unlikely, since they require a conduction velocity that is too rapid to be exhibited by the cardiac tissue. Cardiac signal D7D8 is typically discarded as an un-interpretable channel or signal.

Figure 20A:
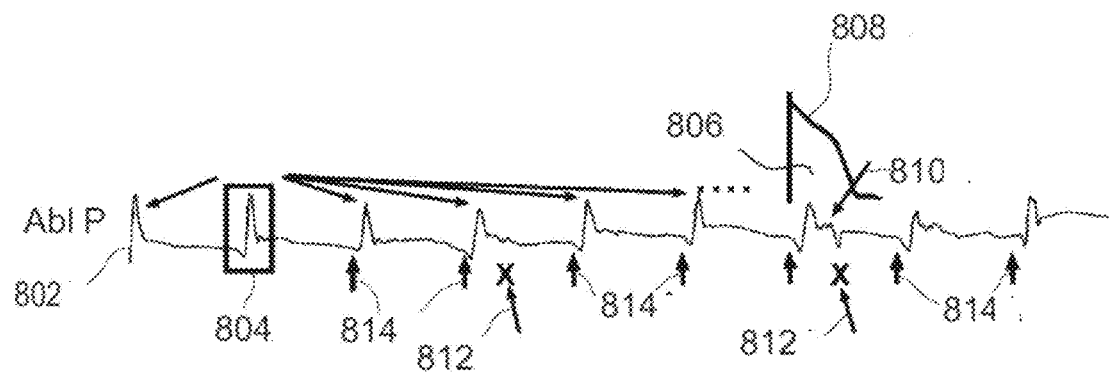
FIG. 20A shows examples of various methods for detecting beats, determining activation onsets, and disregarding noise in the time-varying cardiac signals shown in FIGS. 19A and 19C.

FIG. 20A shows examples of various methods for detecting beats, determining activation onsets, and disregarding noise on the time-varying cardiac signals shown in FIG. 19A. A time-varying cardiac signal from a high-confidence channel is shown as signal 802. In order to mark or tag the activation onsets in signal 802, a template 804 can be derived from one of the more discernible deflections (or beats) in a given time period of the signal 802. This template 804 can then used to detect subsequent and prior beats in signal 802 by using correlation functions, or other methods. Another method that can be used to tag activation onsets in signal 802 is shown using a rate-adapted APD 806, which was essentially described above with reference to FIG. 19C. That is, any deflections that occur in signal 802 before the end 808 of the APD 806, are eliminated or classified as noise since the heart tissue is physically unable to reactivate during this time. Accordingly, the deflections pointed to by arrow 810 are eliminated from being considered activation onsets. Yet another method of accurately determining activation onsets is by filtering out noise within a specified frequency range or bandwidth, as shown by arrows 812 in FIG. 20A, which is then also eliminated from consideration as activation onsets. Activation onset times are determined using a combination of template match, crossing a predetermined voltage threshold, and a maximum dV/dt, which is defined as the maximum rate of change of the voltage with respect to time or slope of the time-varying cardiac signal.

Figure 20B:
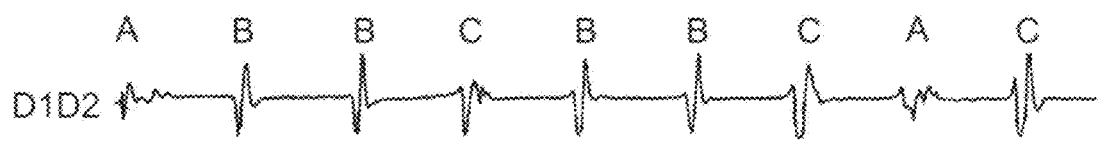
FIG. 20B shows signals from a low-confidence channel.

FIG. 20B shows a signal from a low-confidence channel. For low-confidence channels, different templates may be used to detect various shapes of signal components or deflections. Thus, a different template could be defined and used to detect activation onsets associated with each of a plurality of different shapes identified by "A", "B", and "C" in FIG. 20B.

Figure 20C:
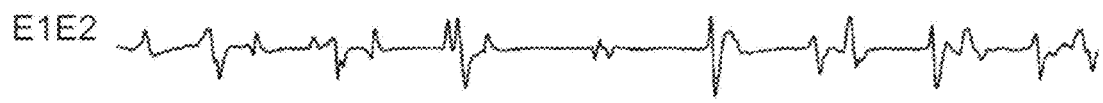
FIG. 20C shows signals from complex and low-confidence channels, in which the shapes of individual beat signals vary widely from beat to beat and thus the activation onset is very difficult to determine.

FIG. 20C shows a signal from a complex channel, in which the shapes of the individual beat representations vary widely from beat to beat. The vector and APD restitution methods, are among the methods described above, which may be used to determine activation onsets for this type of signal.

Figures 21A, 21B:
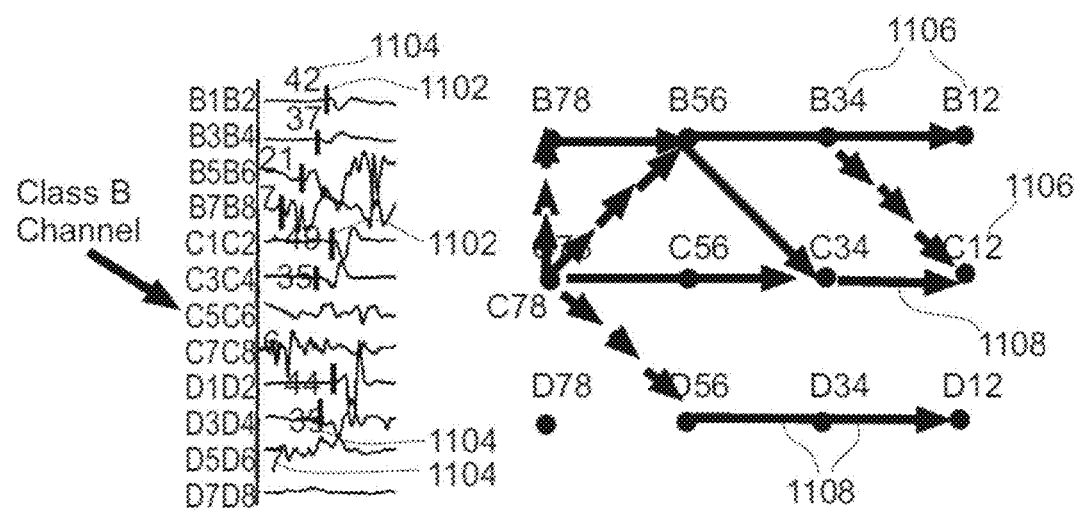
FIGS. 21A and 21B provide additional details to those shown in FIGS. 19B and 19D, respectively, to define a method of determining activation onsets for class B-beats using vectors.

FIGS. 21A and 21B provide additional details to those shown in FIGS. 19B and 19D, respectively, to define a method of determining activation onsets for class B-beats using vectors. As in FIG. 19B, the short vertical lines 1102 shown in FIG. 21A represent example activation onsets determined with respect to the time-varying cardiac signals. The numbers 1104 noted in proximity to each of the vertical lines represent the time of the activation onsets for the corresponding time-varying cardiac signal relative to a given starting time. For example, the activation onset time for cardiac signal B3B4, which is provided as "37", occurs before the activation onset time for cardiac signal B1B2, which is provided as "42". FIG. 21B shows the matrix or grid of sensors denoted by identifications 1106, such as "B34", "B12", "C12", and "D12". Likely vectors are shown in FIG. 21B as arrows or lines 1108 that connect specific sensors 1106. For example, assume that the activation onset at cardiac signal C5C6, which is denoted as a B-channel, is to be determined using vectors from surrounding channels having determinate activation onsets. From FIG. 21B, the most likely vector paths through cardiac signal C5C6 (with the unknown activation onset) is from sensor C78 to C34 since alternate paths through, such as through sensor C56, would exhibit a conduction velocity that is either too fast (such as from sensor B56 to C56), or less probable (such as a zigzag progression through sensors B78, B56, C78, and C56) than that from sensors C78 to C34. Accordingly, the outcome of the analysis indicates that the activation onset for the cardiac signal C5C6 is derived using a vector, which is not necessarily linear, between the activation onsets associated with sensors C78 and C34, and thus cardiac signals C7C8 and C3C4, respectively.

Figure 22A:
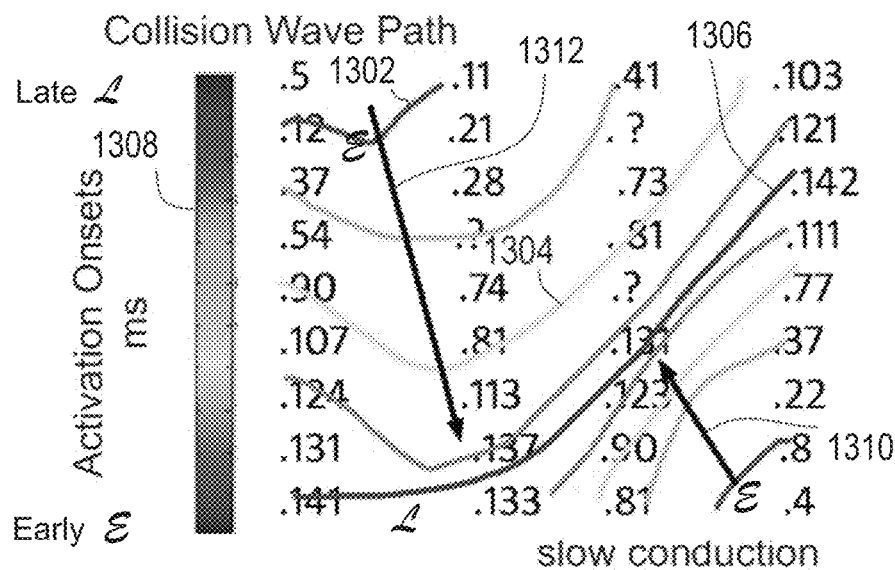
FIGS. 22A-22C show displays of the reconstructed wave paths in fibrillation from selected activation onsets according to the methods and systems described herein.
Figure 22B:
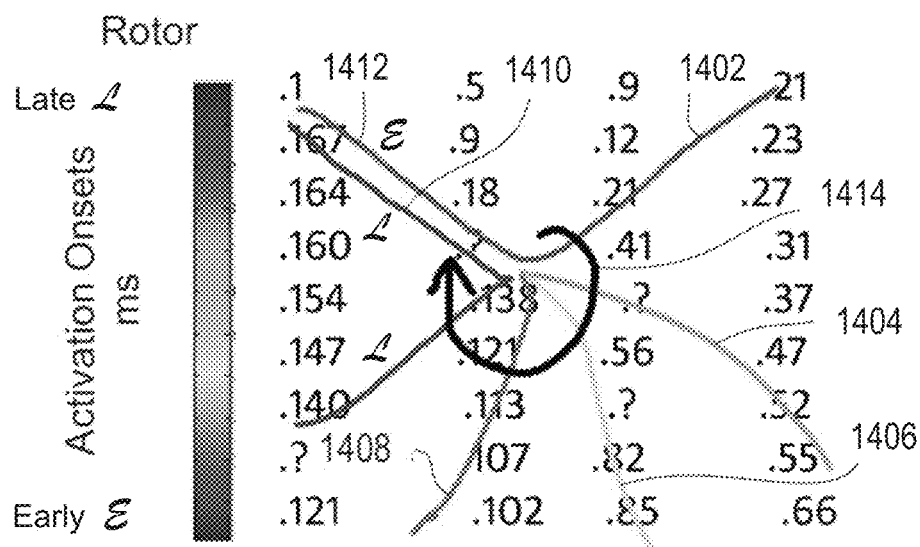
Figure 22C:
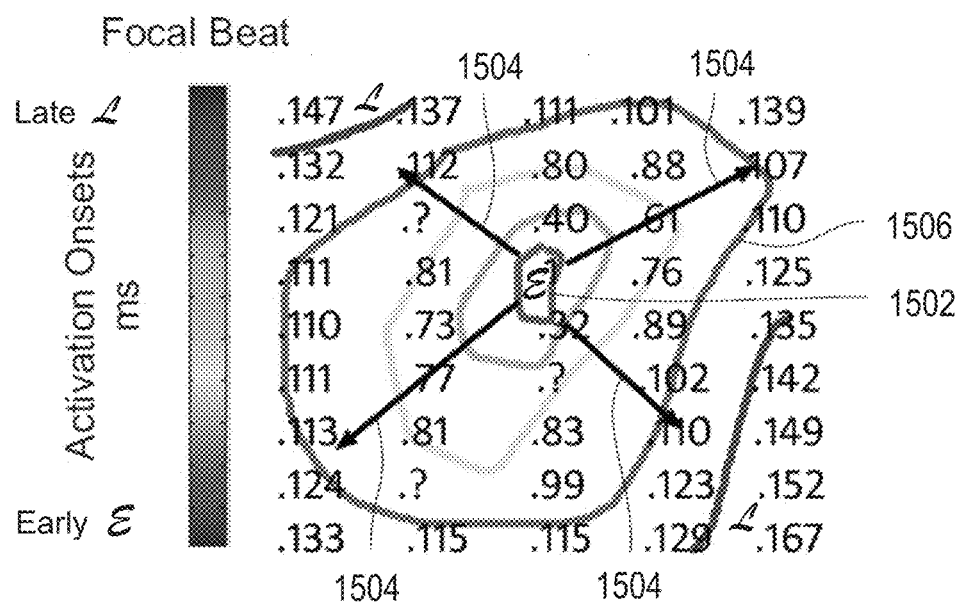

FIGS. 22A-22C provide displays of the reconstructed wave paths in fibrillation from selected activation onsets according to the method and systems described in this application. The activation onsets are provided as numbers (in units of milliseconds) arranged in a two-dimensional array or grid. The grid of numbers shown in each of FIGS. 22A-22C corresponds to the grid of cardiac sensors shown in FIGS. 19B, 19D, and 21B, and thus represents activation onset times determined by corresponding cardiac sensors at the same location. For each channel, the beat under consideration is provided with a number representing its activation onset time in milliseconds, and hence the resulting activation vector over this two-dimensional space. It is to be noted that these activation times may indicate class-A beats, or also class-B beats after initial assignment from FIG. 17B. Low-confidence channels are indicated by a question mark. The wave paths are reconstructed as spatial contours of the same or similar activation onsets. For example, in FIG. 22A, a red contour line 1302 is drawn connecting two sensors with very similar activation onsets (12 ms and 11 ms) to represent a location of the wavefront at approximately 11 ms to 12 ms. Similarly, yellow contour line 1304 is drawn to connect sensors associated with similar activation onset times (90 ms, 81 ms, and 81 ms) to represent a location of the wavefront at approximately 81 ms to 90 ms. The color of each of the contour lines as marked indicates the relative time of each contour line with respect to the remaining contour lines. Accordingly, the earliest contour line will be indicated in red (also be "ε"), and the latest contour line, identified as violet contour line 1306, will be indicated as "L". Arrows 1310, 1312 indicate the direction of the vector as the wave propagates across the contour lines. Thus, FIG. 22A shows a collision of two separate vectors 1310, 1312. The contour lines and vectors are used to define activation onsets at the low confidence signals marked with a question mark.

In addition, activation onsets are determined using APD restitution and repolarization times as well as fiber angles (anatomic paths). For instance, if fiber angles are perpendicular to the vector of propagation at the indicated collision, this adds confidence to the results. Otherwise, another iteration may be required to ensure that activation onset times were not skewed by particular deflections in class-B channels that gave this appearance of slowing. In general, it is expected that wave propagation perpendicular to fiber angles is slower than propagation parallel to fiber angles. Fiber angles are provided from experimentation, and from known angles and anisotropy at certain locations in the atrium, such as the posterior left atrial wall and the septopulmonary bundle of Papez.

Beat shape changes or path discontinuities are shown as blue lines. In general, it is considered that inversion of the beat signal polarity indicates that the wave is passing the bipolar recording electrode in the opposite direction. This information can be used as an additional verification step to determine if wave contours did indeed alter at times of substantial beat polarity change.

Similarly, FIG. 22B shows another example display, except that the wavefront defined thereby is a rotor or rotational pattern, as indicated by the progression of contour line 1402-1412 from "ε" to "L", and an arrow 1414.

Similarly, FIG. 22C shows an example display that represents a focal beat emanating from a central location defined by a contour line 1502, which proceeds outward along the arrows 1504 towards a contour line 1506.

FIG. 23A shows a two-dimensional representation of a matrix of sensors 1602, which are shown as points or electrode positions superimposed on a cardiac atrial surface, indicated by the hand-drawn shape. This shape indicates the left atrium, cut horizontally through the plane of the mitral valve with the two halves folded up and down. Thus, the top portion indicates the superior mitral valve and the bottom portion indicates the inferior mitral valve.

FIG. 23B shows time-varying cardiac signals obtained from nine (9) of the cardiac electrodes or sensors 1602 shown in FIG. 23A. The cardiac signals are denoted as raw signals 1702, since they are obtained directly, or with a minimal amount of processing or filtering, from the cardiac sensors.

FIG. 23C shows an example display obtained from the raw signals 1702 shown in FIG. 23B using conventional methods known in the art. Since the display is obtained directly from the raw signals the result is a confusing map with a plurality of transient patterns that do not indicate any pattern indicative of the origin or earliest activation onset associated with the complex rhythm disorder (i.e., it does not indicate an activation trail). The display of FIG. 24A corresponds to the grid shown in FIG. 23A, in that locations in the grid correspond to the position of the sensors as they relate to locations in a cardiac volume. The shaded areas shown in the display represent activation onsets relative to a given start time in accordance with the scale 1802 on the right side of the display. The color scale 1802 indicates the shading associated with activation onsets (e.g., in milliseconds). Thus, for example, those portions of the display that are shown in area 1804 have an earlier activation onset time than those portions shown in area 1806, which are earlier than those portions shown in area 1808.

FIG. 23C shows the result of tagging activation onsets for beats in each of the nine raw signals in accordance with the systems and method described herein. The activation onsets are shown as dotted lines 1902. Processes outlined in FIGS. 17A-17C are used to generate the activation times for each beat in each channel indicated by vertical lines in FIG. 23C.

FIG. 24B shows an example display derived from the tagging of activation onset times in FIG. 23C, in which a rotor is shown as where the red area 2004 meets the blue area 2006 via the different colors of the color scale between these colors, as shown by arrow 2002 around a core. This core is the fulcrum around which activation rotates to create a rotor. It is to be noted that the display in FIG. 24B clearly indicates the rotor that was undetectable from the display shown in FIG. 24A. It is also to be noted that the precise location of the rotor core may move in space (migrate) over time, but typically remains within a small location in space ("locus").

FIG. 23D shows a reconstruction of the activation potential duration (APD) 2102, which starts at the activation onsets determined in FIG. 23C and extends for a specified time or decay thereafter. Accordingly, the APD 2102 begins with the activation onsets 2104 and extends until the end 2106 of the APD.

FIG. 24C shows a display in which the tagged activation times determined in FIG. 23C and the reconstructed APD determined in FIG. 23D, are used to define the intersection between a depolarization line, which is indicated by a green contour line 2202, and a repolarization line, which is indicated by a blue contour line 2204. Specifically, each reconstructed APD time series is used as an input to the Hilbert transform. A detrending algorithm is applied to set voltages at the activation times to zero. The Hilbert transform is used to construct the phase plane of detrended signals. Then, the Hilbert transform at all electrodes is interpolated across the fine regular grid. The spatial distributions of phase are analyzed with a topological charge technique to locate phase singularities associated with the ends of wavefronts such as at the tip of a reentrant wave. Activation wavefronts are then constructed by tracking isolines of zero phase using an active-edge technique. In summary, for a snapshot in time, green line 2202 indicates the leading edge of depolarization across the tissue, and blue line 2204 indicates the trailing edge of repolarization. The intersection of these lines indicates the rotor core 2200. It has been shown by clinical reduction to practice that this rotor core is the location where targeted ablation energy may terminate and eliminate AF. Other treatments, such as delivery of a depolarizing or repolarizing current, and delivery of gene therapy or other active agents can also be applied to the locus of tissue (spatial region) where the rotor lies.

It is to be noted that these exact techniques can also reveal a focal beat, for which the activation time contours and Hilbert transform would reveal activations emanating from a focal beat origin, with subsequent disorganization if the rhythm resulting in atrial fibrillation or ventricular fibrillation (for which a treatment example is described above).

Figure 25:
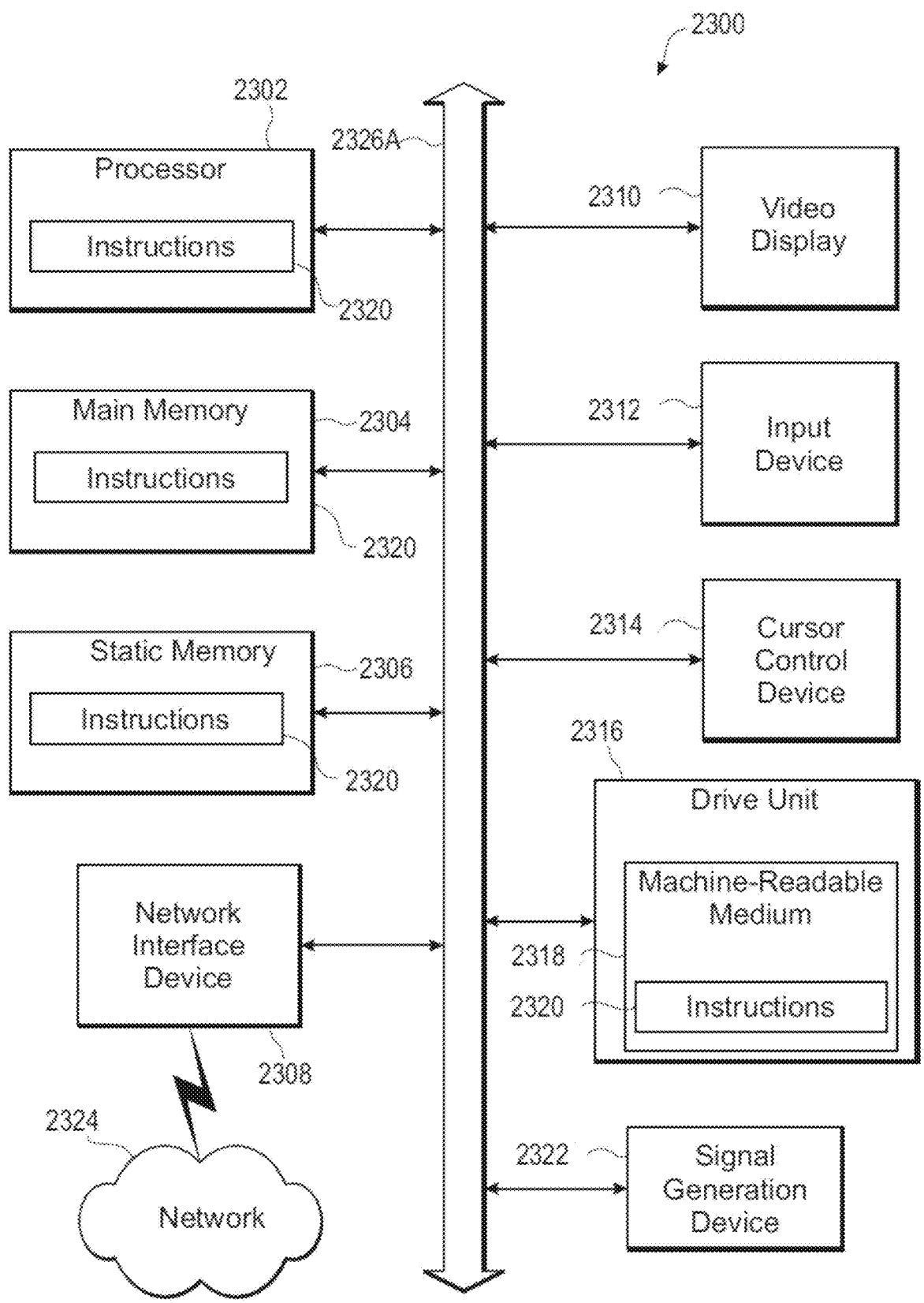
FIG. 25 is a block diagram of a computer system in accordance with the disclosed embodiments.

FIG. 25 is a block diagram of a computer system 2300. The computer system 2300 can include a set of instructions that can be executed to cause the computer system 2300 to perform any one or more of the methods or computer-based functions disclosed herein with respect to FIGS. 17A-24C. The computer system 2300 or any portion thereof, may operate as a standalone device or may be connected (e.g., using a network 2324) to other computer systems or devices disclosed herein with respect to FIGS. 17A-24C. For example, the computer system 2300 can include or be included within any one or more of the catheter, computing device, server, biological sensor, and/or any other devices or systems disclosed herein with respect to FIGS. 1-24C.

In a networked deployment, the computer system 2300 may operate in the capacity of a server or a client machine in a server-client network environment, or a peer machine in a peer-to-peer (or distributed) network environment. The computer system 2300 can also be implemented as or incorporated into various devices, such as a personal computer (PC), a tablet PC, a personal digital assistant (PDA), a web appliance, a communications device, a mobile device, a server, client or any other machine capable of executing a set of instructions (sequential or otherwise) that specify actions to be taken by that machine. Further, while a single computer system 2300 is illustrated, the term "system" shall also be taken to include any collection of systems or sub-systems that individually or jointly execute a set, or multiple sets, of instructions to perform one or more computer functions.

As illustrated in FIG. 25, the computer system 2300 can include a processor 2302, e.g., a central processing unit (CPU), a graphics-processing unit (GPU), or both. Moreover, the computer system 2300 can include a main memory 2304 and a static memory 2306 that can communicate with each other via a bus 2326. As shown, the computer system 2300 may further include a video display unit 2310, such as a liquid crystal display (LCD), an organic light emitting diode (OLED), a flat panel display, a solid state display, or a cathode ray tube (CRT). Additionally, the computer system 2300 may include an input device 2312, such as a keyboard, and a cursor control device 2314, such as a mouse. The computer system 2300 can also include a disk drive unit 2316, a signal generation device 2322, such as a speaker or remote control, and a network interface device 2308.

In a particular embodiment, as depicted in FIG. 25, the disk drive unit 2316 may include a machine or computer-readable medium 2318 in which one or more sets of instructions 2320 (e.g., software) can be embedded. Further, the instructions 2320 may embody one or more of the methods, functions or logic as described herein with reference to FIGS. 1-24C. In some embodiments, the instructions 2320 may reside completely, or at least partially, within the main memory 2304, the static memory 2306, and/or within the processor 2302 during execution by the computer system 2300. The main memory 2304 and the processor 2302 also may include computer-readable media.

In an alternative embodiment, dedicated hardware implementations, such as application specific integrated circuits, programmable logic arrays and other hardware devices, can be constructed to implement one or more of the methods, functions or logic described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with the various embodiments, the methods, functions or logic described herein may be implemented by software programs that are tangibly embodied in a processor-readable medium and that may be executed by a processor. Further, in an example, non-limited embodiment, implementations can include distributed processing, component/object distributed processing, as well as parallel processing. Alternatively, virtual computer system processing can be constructed to implement one or more of the methods, functionality or logic as described herein.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods, functions, logic or operations disclosed herein.

In a particular non-limiting, example embodiment, the computer-readable medium can include a solid-state memory such as a memory card or other package that houses one or more non-volatile read-only memories. Further, the computer-readable medium can be a random-access memory or other volatile re-writable memory.

Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

In accordance with various embodiments, the methods, functions or logic described herein may be implemented as one or more software programs running on a computer processor. Dedicated hardware implementations including, but not limited to, application specific integrated circuits, programmable logic arrays and other hardware devices can likewise be constructed to implement the methods described herein. Furthermore, alternative software implementations including, but not limited to, distributed processing or component/object distributed processing, parallel processing, or virtual machine processing can also be constructed to implement the methods, functions or logic described herein.

It should also be noted that software which implements the disclosed methods, functions or logic may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein, and other equivalents and successor media, in which the software implementations herein may be stored.

In the foregoing sections, methods and systems for detection, diagnosis and/or treatment of biological (complex) rhythm disorders have been described. Although specific example embodiments have been described, it will be evident that various modifications and changes may be made to these embodiments without departing from the broader scope of the inventive subject matter described (invention) herein. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

REFERENCES

Abreu Filho, C. A. C., L. A. F. Lisboa, et al. (2005). "Effectiveness of the Maze Procedure Using Cooled-Tip Radiofrequency Ablation in Patients with Permanent Atrial Fibrillation and Rheumatic Mitral Valve Disease." *Circulation* 112(9 suppl): I-20-25.

Allessie, M. A., J. Ausma, et al. (2002). "Electrical, Contractile and Structural Remodeling during Atrial Fibrillation." *Cardiovasc Res* 54(2): 230-246.

Bardy, G. H., K. L. Lee, et al. (2005). "Amiodarone or an Implantable Cardioverter-Defibrillator for Congestive Heart Failure." *N Engl J Med* 352(3): 225-237.

Calkins, H., J. Brugada, et al. (2007). "HRS/EHRA/ECAS expert Consensus Statement on catheter and surgical ablation of atrial fibrillation: recommendations for personnel, policy, procedures and follow-up. A report of the Heart Rhythm Society (HRS) Task Force on catheter and surgical ablation of atrial fibrillation. European Heart Rhythm Association (EHRA); European Cardiac Arrhythmia Society (ECAS); American College of Cardiology (ACC); American Heart Association (AHA); Society of Thoracic Surgeons (STS)." *Heart Rhythm* 4(6): 816-61.

Cappato, R., H. Calkins, et al. (2005). "Worldwide Survey on the Methods, Efficacy, and Safety of Catheter Ablation for Human Atrial Fibrillation." *Circulation* 111(9): 1100-1105.

Cappato, R., H. Calkins, et al. (2009). "Prevalence and causes of fatal outcome in catheter ablation of atrial fibrillation." *J Am Coll Cardiol* 53(19): 1798-803.

Cheema, A., C. R. Vasamreddy, et al. (2006). "Long-term single procedure efficacy of catheter ablation of atrial fibrillation" *J Intery Card Electrophysiol* 15(3): 145-155.

Cox, J. L. (2004). "Cardiac Surgery for Arrhythmias." *J. Cardiovasc Electrophysiol.* 15: 250-262.

Cox, J. L. (2005). "The central controversy surrounding the interventional-surgical treatment of atrial fibrillation." *J. Thorac. Cardiovasc. Surg.* 129(1): I-4.

Ellis, E. R., S. D. Culler, et al. (2009). "Trends in utilization and complications of catheter ablation for atrial fibrillation in Medicare beneficiaries." *Heart Rhythm* 6(9): 1267-73.

Gaspo, R., R. F. Bosch, et al. (1997). "Functional Mechanisms Underlying Tachycardia-Induced Sustained Atrial Fibrillation in a Chronic Dog Model." *Circulation* 96(11): 4027-4035.

Kalifa, J., K. Tanaka, et al. (2006). "Mechanisms of Wave Fractionation at Boundaries of High-Frequency Excitation in the Posterior Left Atrium of the Isolated Sheep Heart During Atrial Fibrillation." *Circulation* 113(5): 626-633.

Knecht, S., F. Sacher, et al. (2009). "Long Term Follow-Up of Idiopathic Ventricular Fibrillation Ablation: A Multicenter Study." *J Am Coll Cardiol* 54(6): 552-528.

Masse, S., E. Downar, et al. (2007). "Ventricular fibrillation in myopathic human hearts: mechanistic insights from in vivo global endocardial and epicardial mapping." *Am J Physiol Heart Circ Physiol* 292(6): H2589-97.

Myerburg, R. J. and A. Castellanos (2006). "Emerging paradigms of the epidemiology and demographics of sudden cardiac arrest." *Heart Rhythm* 3(2): 235-239.

Nademanee, K., J. McKenzie, et al. (2004a). "A new approach for catheter ablation of atrial fibrillation: mapping of the electrophysiologic substrate." *J. Am. Coll. Cardiol.* 43(11): 2044-2053.

Narayan, S. M., D. E. Krummen, et al. (2006d). "Evaluating Fluctuations in Human Atrial Fibrillatory Cycle Length Using Monophasic Action Potentials." *Pacing Clin Electrophysiol* 29(11): 1209-1218.

Nash, M. P., A. Mourad, et al. (2006). "Evidence for Multiple Mechanisms in Human Ventricular Fibrillation" *Circulation* 114: 536-542.

Ng, J., A. H. Kadish, et al. (2006). "Effect of electrogram characteristics on the relationship of dominant frequency to atrial activation rate in atrial fibrillation." *Heart Rhythm* 3(11): 1295-1305.

Ng, J., A. H. Kadish, et al. (2007). "Technical considerations for dominant frequency analysis." *J Cardiovasc Electrophysiol* 18(7): 757-64.

Oral, H., A. Chugh, et al. (2007). "Radiofrequency catheter ablation of chronic atrial fibrillation guided by complex electrograms." *Circulation* 115(20): 2606-12.

Oral, H., A. Chugh, et al. (2009). "A randomized assessment of the incremental role of ablation of complex fractionated atrial electrograms after antral pulmonary vein isolation for long-lasting persistent atrial fibrillation." *J Am Coll Cardiol* 53(9): 782-9.

Reddy, V. Y., M. R. Reynolds, et al. (2007). "Prophylactic catheter ablation for the prevention of defibrillator therapy." *N Engl J Med* 357(26): 2657-65.

Ryu, K., S. C. Shroff, et al. (2005). "Mapping of Atrial Activation During Sustained Atrial Fibrillation in Dogs with Rapid Ventricular Pacing Induced Heart Failure: Evidence for a Role of Driver Regions." *Journal of Cardiovascular Electrophysiology* 16(12): 1348-1358.

Sahadevan, J., K. Ryu, et al. (2004). "Epicardial Mapping of Chronic Atrial Fibrillation in Patients: Preliminary Observations." *Circulation* 110(21): 3293-3299.

Sanders, P., O. Berenfeld, et al. (2005a). "Spectral Analysis Identifies Sites of High-Frequency Activity Maintaining Atrial Fibrillation in Humans." *Circulation* 112(6): 789-797.

Singh, B. N., S. N. Singh, et al. (2005). "Amiodarone versus Sotalol for Atrial Fibrillation." *N Engl J Med* 352(18): 1861-1872.

Skanes, A. C., R. Mandapati, et al. (1998). "Spatiotemporal Periodicity During Atrial Fibrillation in the Isolated Sheep Heart." *Circulation* 98(12): 1236-1248.

Tabereaux, P. B., G. P. Walcott, et al. (2007). "Activation patterns of Purkinje fibers during long-duration ventricular fibrillation in an isolated canine heart model." *Circulation* 116(10): 1113-9.

Vaquero, M., D. Calvo, et al. (2008). "Cardiac fibrillation: From ion channels to rotors in the human heart." *Heart Rhythm*.

Waldo, A. L. and G. K. Feld (2008). "Inter-relationships of atrial fibrillation and atrial flutter mechanisms and clinical implications." *J Am Coll Cardiol* 51(8): 779-86.

Warren, M., P. K. Guha, et al. (2003). "Blockade of the inward rectifying potassium current terminates ventricular fibrillation in the guinea pig heart." *J Cardiovasc Electrophysiol* 14(6): 621-31.

Wijffels, M. C., C. J. Kirchhof, et al. (1995). "Atrial fibrillation begets atrial fibrillation: a study in awake chronically instrumented goats." *Circulation* 92: 1954-1968.

The invention claimed is:

1. A system to process cardiac activation information associated with a complex heart rhythm disorder, the system comprises a computing device:
   obtaining cardiac information signals from sensors associated with a patient;
   accessing the cardiac information signals from the sensors associated with a plurality of locations of a patient's heart, the signals including at least a first signal and a second signal, each signal comprising a plurality of beats;
   determining whether one or more beats within the plurality of beats in the first signal are non-discernible according to predetermined criteria;
   determining activations in the cardiac information signals, wherein at least one activation associated with a non-discernible beat in the first signal at a first location is determined at least with reference to an activation associated with a discernible beat in the second signal at a second location, the first location and second location being proximate neighbors; and
   identifying a location of the complex heart rhythm disorder based upon the determined activations wherein said location is a physical location within the heart.

2. The system of claim 1, wherein identifying the location comprises processing the activations by phase analysis, Hilbert transform, time domain analysis, or dominant frequency analysis.

3. The system of claim 1, wherein identifying the location comprises ordering the activations to generate an activation trail and further comprising constructing a clinical representation of the activation trail.

4. The system of claim 3, wherein the activation trail comprises a rotational pattern or a radially emanating pattern.

5. The system of claim 4, further comprising identifying an approximate core of the source of the complex heart rhythm disorder based on the activation trail.

6. The system of claim 5, wherein the approximate core is a rotor or focal source that radially emanates outwardly from the approximate core.

7. A system to identify a source of a heart rhythm disorder, the system comprising a computing device:
   obtaining cardiac information signals associated with sensors from a patient;
   accessing the cardiac information signals obtained from the sensors associated with a plurality of locations of a patient's heart, the signals including at least a first signal and a second signal, each signal comprising a plurality of beats;
   determining whether one or more beats within the plurality of beats in the first signal are non-discernible according to predetermined criteria;
   determining activations in the cardiac information signals, wherein at least one activation associated with a non-discernible beat in the first signal at a first location is determined at least with reference to an activation associated with discernible beats in the second signals at second locations, the first location and second locations being proximate neighbors; and
   identifying a location of the complex heart rhythm disorder based upon the determined activations wherein said location is a physical location within the heart.

8. The system of claim 7, wherein identifying the location comprises processing the determined activations by phase analysis, Hilbert transform, time domain analysis, or dominant frequency analysis.

9. The system of claim 7, wherein identifying the location comprises ordering the activations to generate an activation trail and further comprising constructing a clinical representation of the activation trail.

10. The system of claim 9, wherein the activation trail comprises a rotational pattern or a radially emanating pattern.

11. The system of claim 10, further comprising identifying an approximate core of the source of the complex heart rhythm disorder based on the activation trail.

12. The system of claim 11, wherein the approximate core is a rotor or focal source that radially emanates outwardly from the approximate core.

13. The system of claim 7, further comprising the computing device analyzing the activations as determined in the first signal with reference to the second signal in order to determine a set of activations attributable to discernible beats of the proximate neighbors.

14. The system of claim 13, further comprising the computing device using the set of activations to determine discernible beats in the first signal.

15. The system of claim 7, further comprising the computing device determining activations in the signals using at least one activation in a signal of a first location that is calculated with reference to signals of at least two locations that are neighbors to the first location.

16. The system of claim 7, further comprising the computing device selecting a reconciled activation based on the activation located closest to at least one of the calculated activations or the average of the activations.

17. The system of claim 7, further comprising the computing device classifying the cardiac information signals into high and low confidence signals, wherein the high and low confidence signals are separated by a confidence threshold.

18. The system of claim 17, wherein the confidence threshold is associated with a predetermined percentage of discernible beats out of total beats associated with each of the high and low confidence signals.

19. The system of claim 17, further comprising the computing device determining an activation associated with at least one low confidence signal within an acceptance time window, the acceptance time window associated with the low confidence signal indicating an earliest activation and a latest termination for a beat in the low confidence signal.

20. The system of claim 19, wherein determining further comprises determining activations associated with the low confidence signals within associated acceptance time windows, each of the acceptance time windows associated with a low confidence signal indicating an earliest activation and a latest termination for a beat in the low confidence signal.

21. The system of claim 20, further comprising ordering the activations associated with the high and low confidence signals.

22. The system of claim 19, wherein the acceptance time window is determined using at least one of action potential duration (APD), conduction velocity (CV), fiber angle, time vector connecting at least two discernible activation onsets of the high confidence signals associated with spatially adjacent sensors, and anatomic factors.

23. The system of claim 17, further comprising the computing device identifying a plurality of discernible beats on high confidence signals of sensors that are spatially adjacent to a sensor associated with a low confidence signal, the discernible beats on the high-confidence signals corresponding to a non-discernible beat on the low-confidence signal.

24. The system of claim 23, further comprising the computing device computing a time vector between at least two activations associated with the identified discernible beats on the high-confidence signals through the non-discernible beat on the low-confidence signal.

25. The system of claim 24, further comprising the computing device defining a time interval associated with the non-discernible beat about a region of the low-confidence signal where the computed time vector crosses the non-discernible beat, the time interval indicating how early the non-discernible beat is able to activate based on a previous beat on the low-confidence signal that has a selected or determined activation and how late the non-discernible beat is able to terminate based on at least one predetermined property.

26. The system of claim 25, further comprising selecting a possible activation during the defined time interval that is closest to the computed time vector for the non-discernible beat.

27. The system of claim 17, wherein classifying further comprises using at least one of activation onset, cycle length (CL), action potential duration (APD), and amplitude to classify the cardiac information signals into the high and low confidence signals, wherein the activation onsets are determined by using at least one of maximum dV/dt, template matching, frequency and amplitude.

\* \* \* \* \*